United States Patent
Kerkkamp et al.

(10) Patent No.: US 11,680,088 B2
(45) Date of Patent: Jun. 20, 2023

(54) BIOACTIVE PEPTIDES DERIVED FROM SNAKES

(71) Applicants: Universiteit Leiden, Leiden (NL); Academisch Ziekenhuis Leiden h.o.d.n. LUMC, Leiden (NL)

(72) Inventors: Harald Martijn Ijsbrand Kerkkamp, The Hague (NL); Michael Keith Richardson, Leiderdorp (NL); Gilles Philippus van Wezel, Heemstede (NL); Jan Wouter Drijfhout, Leiden (NL); Robert Alexander Cordfunke, Delft (NL); Michella Manon Voet, Haarlem (NL); Petrus Hendricus Nibbering, Voorhout (NL)

(73) Assignees: Universiteit Leiden, Leiden (NL); Academisch Ziekenhuis Leiden h.o.d.n. LUMC, Leiden (NL)

( * ) Notice: Subject to any disclaimer, the term of this patent is extended or adjusted under 35 U.S.C. 154(b) by 0 days.

(21) Appl. No.: 17/276,452

(22) PCT Filed: Sep. 17, 2019

(86) PCT No.: PCT/NL2019/050612
§ 371 (c)(1),
(2) Date: Mar. 15, 2021

(87) PCT Pub. No.: WO2020/060401
PCT Pub. Date: Mar. 26, 2020

(65) Prior Publication Data
US 2022/0064231 A1 Mar. 3, 2022

(30) Foreign Application Priority Data
Sep. 17, 2018 (EP) ..................... 18194912

(51) Int. Cl.
*A61K 38/17* (2006.01)
*C07K 14/46* (2006.01)
*A61K 38/00* (2006.01)

(52) U.S. Cl.
CPC ............ *C07K 14/46* (2013.01); *A61K 38/00* (2013.01)

(58) Field of Classification Search
None
See application file for complete search history.

(56) References Cited

U.S. PATENT DOCUMENTS

2020/0165309 A1* 5/2020 Yount .................. G16B 15/20

FOREIGN PATENT DOCUMENTS

| CN | 102311492 A | 1/2012 |
|---|---|---|
| WO | 2010148079 A1 | 12/2010 |
| WO | 2014060610 A2 | 4/2014 |
| WO | 2017176041 A1 | 10/2017 |

OTHER PUBLICATIONS

Bahar et al. "Antimicrobial Peptides" Pharmaceuticals, vol. 6 (Nov. 28, 2013) pp. 1543-1575.
Boucher et al. "Bad Bugs, No Drugs: No. ESKAPE! An Update from the Infectious Diseases Society of America" Clin. Infect Dis; 48 (Jan. 2009) 12 pages.
Brauner et al. "Distinguishing between resistance, tolerance and persistence to antibiotic treatment" Nat Rev Microbiol; vol. 14 (5) (Apr. 2016) pp. 321-330, abstract only.
Cho et al. "Enhanced IL-12p40 production in LPS-stimulated macrophages by inhibiting JNK activation by artemisinin." Arch Pharm. Res; vol. 35 (Nov. 2012) pp. 1951-1968.
De Kraker et al. "Will 10 Million People Die a Year due to Antimicrobial Resistance by 2050?" PLoS Med; vol. 13:11 (Nov. 2016) e1002184.
De Latour et al. "Antimicrobial activity of the Naja atra cathelicidin and related small peptides" Biochemical and Biophysical Research Communications; vol. 396 (May 10, 2010) pp. 825-830.
Dean et al. "Natural and synthetic cathelicidin peptides with antimicrobial and anti-biofilm activity against *Staphylococcus aureus*" BMC Microbiology 11 Article 114 ( May 23, 2011) https://doi.org/10.1186/1471-2180-11-114.
Falcao et al. "Vipericidins; a novel family of cathelicidin-related peptides from the venom gland of South American pitvipers" Amino Acids; vol. 46 (Jun. 2014) pp. 2561-2571.
O'Neil "Tackling drug-resistant infections globally: Final report and recommendations" 2016; on the world-wide web at amr-review.org/sites/default/files/160518_Final%20paper_with%20cover.pdf (accessed Jul. 26, 2022).
Olsen "Biofilms-specific antibiotic tolerance and resistance" Eur. J. Clin. Microbiol. Infect. Dis; vol. 34 (May 2015) pp. 877-886, abstract only.
Scott et al. "The Human Antimicrobial Peptide LL-37 is a Multifunctional Modulator of Innate Immune Responses" The Journal of Immunology, 2002; vol. 169, pp. 3883-3891 (Downloaded from http://www.jimmunol.org/ on Mar. 17, 2022).
Shek et al. "Oral bacterial flora of the Chinese cobra (*Naja atra*) and bamboo pit viper (*Trimeresurus albolabris*) in Hong Kong SAR, China" Hong Kong Med. J ; vol. 15 (Jun. 2009) pp. 183-190.
Van Der Does et al. "LL-37 directs macrophage differentiation toward macrophages with a pro-inflammatory signature" J. Immunol; vol. 185 (Aug. 2010) pp. 1442-1449.
Von Rosenvinge et al. "Microbial biofilms and gastrointestinal diseases" Pathogens and Disease, vol. 67, Issue 1 (Feb. 2013) pp. 25-38.

(Continued)

*Primary Examiner* — Fred H Reynolds
(74) *Attorney, Agent, or Firm* — TraskBritt

(57) ABSTRACT

The disclosure concerns snake-derived peptides and the useful application of such peptides to inhibit bacterial, fungal, viral and parasitic infections. The disclosed peptides are also useful for the treatment of an inflammatory condition or cancers.

9 Claims, 11 Drawing Sheets

Specification includes a Sequence Listing.

(56) References Cited

OTHER PUBLICATIONS

Wang et al. "BF-30 selectively inhibits melanoma cell proliferation via cytoplasmic membrane permeabilization and DNA-binding in vitro and in B16F10-bearing mice" Eur. J. Pharmacol; vol. 707 (Mar. 2013) 10 pages.
Zhao et al. "King cobra peptide OH-CATH30 as a potential candidate drug through clinic drug-resistant isolates" Zoological research; vol. 39 (Feb. 2018) pp. 87-96.
International Search Report for International Application No. PCT/NL2019/050612, dated Jun. 29, 2021, 7 pages.
International Written Opinion for International Application No. PCT/NL2019/050612, dated Jun. 29, 2021, 10 pages.
Hoiby et al. "Antibiotic resistance of bacterial biofilms" Int J Antimicrob Agents, (Apr. 2010) 35(4):322-32.
Kosciuczuk et al. "Cathelicidins: family of antimicrobial peptides. A review" Mol Biol Rep (Oct. 2012) 39:10957-10970 https://doi.org/10.1007/s11033-012-1997-x.
Overhage et al. "Human Host Defense Peptide LI-37 Prevents Bacterial Biofilm Formation" Infection and Mmunity, p. 4176-4182 vol. 76, No. 9 (Sep. 2008).
Cai et al. "Python Cathelicidin CATHPb1 Protects against Multidrug-Resistant Staphylococcal Infections by Antimicrobial-Immunomodulatory Duality" Journal of Medicinal Chemistry, vol. 61 (Feb. 21, 2018) pp. 2075-2086.

\* cited by examiner

Figure 3.

| Species | Strain | Antibiotic resistance | LC99.9 SP4 (µM) 50% plasma | LC99.9 SP94 (µM) 50% plasma |
|---|---|---|---|---|
| E. faecium | LUH15122 | | 1.6 | 3.2 |
| S. aureus | LUH14616 | | 3.2 (3.2 - 12.8) | 6.4 (3.2 - 6.4) |
| K. pneumoniae | LUH15104 | | 0.2 | 0.2 |
| A. baumannii | RUH875 | | 0.4 (0.4 - 1.6) | 0.8 |
| P. aeruginosa | LUH15103 | | 0.4 (0.2 - 1.6) | 0.8 (0.2 - 1.6) |
| E. cloacae | LUH15114 | | 0.2 (0.1 - 0.4) | 0.1 (0.05 - 0.2) |
| E. coli | LUH15117 | | 0.1 (0.1 - 0.2) | 0.1 (0.1 - 0.2) |

SEQUENCE LISTING

<160> NUMBER OF SEQ ID NOS: 147

<210> SEQ ID NO 1
<211> LENGTH: 40
<212> TYPE: PRT
<213> ORGANISM: Artificial Sequence
<220> FEATURE:
<223> OTHER INFORMATION: recombinant peptide SP1

<400> SEQUENCE: 1

Arg Lys Phe Lys Lys Ser Phe Lys Lys Ile Arg Lys Trp Val Lys Lys
1               5                   10                  15

Ala Thr Lys Ile Ala Gly Glu Val Ala Val Glu Ile Leu Ile Thr Lys
            20                  25                  30

Val Ile Leu Gly Ser Val Gly Leu
        35                  40

<210> SEQ ID NO 2
<211> LENGTH: 37
<212> TYPE: PRT
<213> ORGANISM: Artificial Sequence
<220> FEATURE:
<223> OTHER INFORMATION: recombinant peptide SP2

<400> SEQUENCE: 2

Lys Arg Val Lys Arg Phe Lys Lys Phe Phe Lys Lys Val Lys Lys Ser
1               5                   10                  15

Val Lys Lys Arg Leu Lys Lys Ile Phe Lys Lys Pro Met Val Ile Gly
            20                  25                  30

Val Thr Ile Pro Phe
        35

<210> SEQ ID NO 3
<211> LENGTH: 34
<212> TYPE: PRT
<213> ORGANISM: Artificial Sequence
<220> FEATURE:
<223> OTHER INFORMATION: recombinant peptide SP3

<400> SEQUENCE: 3

Lys Arg Phe Lys Lys Phe Phe Lys Lys Leu Lys Asn Ser Val Lys Lys
1               5                   10                  15

Arg Val Lys Lys Phe Phe Arg Lys Pro Arg Val Ile Gly Val Thr Phe
            20                  25                  30

Pro Phe

<210> SEQ ID NO 4
<211> LENGTH: 34
<212> TYPE: PRT
<213> ORGANISM: Artificial Sequence
<220> FEATURE:
<223> OTHER INFORMATION: recombinant peptide SP4

<400> SEQUENCE: 4

Lys Arg Phe Lys Lys Phe Phe Lys Lys Leu Lys Asn Asn Val Lys Lys
1               5                   10                  15

Arg Val Lys Lys Phe Phe Arg Lys Pro Arg Val Ile Gly Val Thr Ile
            20                  25                  30

Pro Phe

<210> SEQ ID NO 5
<211> LENGTH: 34

-continued

<212> TYPE: PRT
<213> ORGANISM: Artificial Sequence
<220> FEATURE:
<223> OTHER INFORMATION: recombinant peptide SP5

<400> SEQUENCE: 5

Lys Arg Phe Lys Lys Phe Phe Arg Lys Leu Lys Ser Val Lys Lys
1               5                   10                  15

Arg Ala Lys Glu Phe Phe Lys Lys Pro Arg Val Ile Gly Val Ser Ile
            20                  25                  30

Pro Phe

<210> SEQ ID NO 6
<211> LENGTH: 34
<212> TYPE: PRT
<213> ORGANISM: Artificial Sequence
<220> FEATURE:
<223> OTHER INFORMATION: recombinant peptide SP6

<400> SEQUENCE: 6

Lys Arg Phe Lys Lys Phe Phe Lys Lys Val Lys Lys Ser Val Lys Lys
1               5                   10                  15

Arg Leu Lys Lys Ile Phe Lys Lys Pro Met Val Ile Gly Val Thr Ile
            20                  25                  30

Pro Phe

<210> SEQ ID NO 7
<211> LENGTH: 34
<212> TYPE: PRT
<213> ORGANISM: Artificial Sequence
<220> FEATURE:
<223> OTHER INFORMATION: recombinant peptide SP7

<400> SEQUENCE: 7

Lys Arg Phe Lys Lys Phe Phe Lys Lys Val Lys Lys Ser Val Lys Lys
1               5                   10                  15

Arg Leu Lys Lys Ile Phe Lys Lys Pro Met Val Ile Gly Val Ser Ile
            20                  25                  30

Pro Phe

<210> SEQ ID NO 8
<211> LENGTH: 34
<212> TYPE: PRT
<213> ORGANISM: Artificial Sequence
<220> FEATURE:
<223> OTHER INFORMATION: recombinant peptide SP8

<400> SEQUENCE: 8

Lys Arg Phe Arg Lys Phe Phe Lys Lys Arg Leu Leu Lys Ser Val Arg Arg
1               5                   10                  15

Ala Val Lys Lys Phe Arg Lys Lys Pro Arg Leu Ile Gly Leu Ser Thr
            20                  25                  30

Leu Leu

<210> SEQ ID NO 9
<211> LENGTH: 34
<212> TYPE: PRT
<213> ORGANISM: Artificial Sequence
<220> FEATURE:
<223> OTHER INFORMATION: recombinant peptide SP9

<400> SEQUENCE: 9

```
Lys Arg Phe Lys Lys Phe Phe Lys Lys Val Lys Ser Val Lys Lys
1               5                   10                  15

Arg Leu Lys Lys Ile Phe Lys Lys Pro Met Val Ile Gly Val Thr Phe
            20                  25                  30

Pro Phe
```

<210> SEQ ID NO 10
<211> LENGTH: 34
<212> TYPE: PRT
<213> ORGANISM: Artificial Sequence
<220> FEATURE:
<223> OTHER INFORMATION: recombinant peptide SP11

<400> SEQUENCE: 10

```
Lys Arg Phe Lys Lys Phe Phe Arg Lys Leu Lys Lys Ser Val Lys Lys
1               5                   10                  15

Arg Val Lys Lys Phe Phe Lys Lys Pro Arg Val Ile Gly Val Thr Ile
            20                  25                  30

Pro Phe
```

<210> SEQ ID NO 11
<211> LENGTH: 34
<212> TYPE: PRT
<213> ORGANISM: Artificial Sequence
<220> FEATURE:
<223> OTHER INFORMATION: recombinant peptide SP12

<400> SEQUENCE: 11

```
Lys Arg Phe Lys Lys Phe Phe Met Lys Leu Lys Lys Ser Val Lys Lys
1               5                   10                  15

Arg Val Met Lys Phe Phe Lys Lys Pro Met Val Ile Gly Val Thr Phe
            20                  25                  30

Pro Phe
```

<210> SEQ ID NO 12
<211> LENGTH: 34
<212> TYPE: PRT
<213> ORGANISM: Artificial Sequence
<220> FEATURE:
<223> OTHER INFORMATION: recombinant peptide SP14

<400> SEQUENCE: 12

```
Lys Arg Phe Lys Lys Phe Phe Lys Lys Ala Lys Lys Ser Val Lys Lys
1               5                   10                  15

Arg Leu Lys Lys Phe Phe Asn Lys Thr Arg Val Ile Gly Val Ser Ile
            20                  25                  30

Pro Phe
```

<210> SEQ ID NO 13
<211> LENGTH: 31
<212> TYPE: PRT
<213> ORGANISM: Artificial Sequence
<220> FEATURE:
<223> OTHER INFORMATION: recombinant peptide SP15

<400> SEQUENCE: 13

```
Lys Arg Phe Lys Lys Phe Phe Arg Lys Ile Lys Lys Gly Phe Arg Lys
1               5                   10                  15

Ile Phe Lys Lys Thr Lys Ile Phe Ile Gly Gly Thr Ile Pro Ile
            20                  25                  30
```

```
<210> SEQ ID NO 14
<211> LENGTH: 31
<212> TYPE: PRT
<213> ORGANISM: Artificial Sequence
<220> FEATURE:
<223> OTHER INFORMATION: rcombinant peptide SP16

<400> SEQUENCE: 14

Lys Arg Phe Gln Asn Phe Phe Arg Glu Leu Glu Lys Lys Phe Arg Glu
1               5                   10                  15

Phe Phe Arg Val Tyr Arg Ile Thr Ile Gly Ala Thr Ile Arg Phe
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: recombinant peptide SP17

<400> SEQUENCE: 15

Lys Arg Phe Lys Asp Phe Phe His Arg Ile Arg Asp Gly Val Arg Asp
1               5                   10                  15

Phe Phe Arg Asn Asn His Phe Val Cys Gly Val Asn Phe Arg Phe
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: recombinant peptide SP18

<400> SEQUENCE: 16

Lys Arg Phe Lys Lys Phe Phe Lys Lys Ile Lys Thr Gly Ile Lys Lys
1               5                   10                  15

Val Ile Lys Lys Thr Lys Gln Ala Ile Ala Ser His Phe Arg Trp
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: recombinant peptide SP19

<400> SEQUENCE: 17

Lys Arg Phe Leu Arg Val Phe Lys Leu Lys Arg Gly Ile Arg Lys
1               5                   10                  15

Leu Phe Lys Lys Lys Lys Ile Val Thr Gly Pro Leu Thr Ser
            20                  25                  30

<210> SEQ ID NO 18
<211> LENGTH: 25
<212> TYPE: PRT
<213> ORGANISM: Artificial Sequence
<220> FEATURE:
<223> OTHER INFORMATION: recombinant peptide SP20

<400> SEQUENCE: 18

Ala Arg Glu Lys Ser Phe Leu Gln Lys Met Lys Val Ile Leu Gln Leu
1               5                   10                  15

Ser Ser Gln Asp Gln Ile Gln Ala Phe
            20                  25
```

<210> SEQ ID NO 19
<211> LENGTH: 17
<212> TYPE: PRT
<213> ORGANISM: Artificial Sequence
<220> FEATURE:
<223> OTHER INFORMATION: recombinant peptide SP21

<400> SEQUENCE: 19

Lys Arg Phe Ala Gly Phe Phe Gln Phe Val Ile Gly Val Ser Phe His
1               5                   10                  15

Phe

<210> SEQ ID NO 20
<211> LENGTH: 42
<212> TYPE: PRT
<213> ORGANISM: Artificial Sequence
<220> FEATURE:
<223> OTHER INFORMATION: recombinant peptide SP22

<400> SEQUENCE: 20

Asp Gln Val Glu Arg Gly Asn Phe Ala Lys Asp Gly Ser Lys Ala Arg
1               5                   10                  15

Val Lys Lys Ser Leu Thr Lys Trp Val Lys Phe Leu Lys Lys Ile Ile
            20                  25                  30

Ala Lys Leu Gly Arg Pro Leu Ile Gly Phe
        35                  40

<210> SEQ ID NO 21
<211> LENGTH: 34
<212> TYPE: PRT
<213> ORGANISM: Artificial Sequence
<220> FEATURE:
<223> OTHER INFORMATION: recombinant peptide SP23

<400> SEQUENCE: 21

Lys Arg Phe Lys Lys Phe Phe Lys Lys Ile Lys Asn Ser Val Lys Lys
1               5                   10                  15

Arg Val Lys Lys Phe Phe Lys Lys Pro Arg Val Ile Gly Val Ser Ile
            20                  25                  30

Pro Phe

<210> SEQ ID NO 22
<211> LENGTH: 34
<212> TYPE: PRT
<213> ORGANISM: Artificial Sequence
<220> FEATURE:
<223> OTHER INFORMATION: recombinant peptide SP24

<400> SEQUENCE: 22

Lys Arg Phe Lys Lys Phe Phe Lys Lys Leu Lys Asn Ser Val Arg Lys
1               5                   10                  15

Cys Ala Lys Lys Phe Phe Lys Lys Leu Arg Val Ile Arg Val Ser Ile
            20                  25                  30

Pro Phe

<210> SEQ ID NO 23
<211> LENGTH: 34
<212> TYPE: PRT
<213> ORGANISM: Artificial Sequence
<220> FEATURE:
<223> OTHER INFORMATION: recombinant peptide SP25

<400> SEQUENCE: 23

```
Lys Arg Phe Lys Lys Phe Phe Lys Lys Val Lys Lys Ser Val Lys Lys
1               5                   10                  15

Arg Leu Lys Lys Ile Phe Lys Lys Pro Ile Val Ile Gly Val Ser Ile
                20                  25                  30

Pro Phe
```

<210> SEQ ID NO 24
<211> LENGTH: 33
<212> TYPE: PRT
<213> ORGANISM: Artificial Sequence
<220> FEATURE:
<223> OTHER INFORMATION: recombinant peptide SP26

<400> SEQUENCE: 24

```
Lys Arg Phe Thr Phe Tyr Lys Lys Val Lys Lys Asn Val Glu Asn Leu
1               5                   10                  15

Leu Asn Lys Phe Phe Lys Lys Leu Arg Val Ile Gly Asp Ser Ile Pro
                20                  25                  30

Phe
```

<210> SEQ ID NO 25
<211> LENGTH: 33
<212> TYPE: PRT
<213> ORGANISM: Artificial Sequence
<220> FEATURE:
<223> OTHER INFORMATION: recombinant peptide SP27

<400> SEQUENCE: 25

```
Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
                20                  25                  30

Gly
```

<210> SEQ ID NO 26
<211> LENGTH: 32
<212> TYPE: PRT
<213> ORGANISM: Artificial Sequence
<220> FEATURE:
<223> OTHER INFORMATION: recombinant peptide SP28

<400> SEQUENCE: 26

```
Lys Arg Phe Leu Arg Leu Val Val Phe Lys Lys Leu Lys Lys Gly Leu
1               5                   10                  15

Arg Lys Leu Phe Lys Lys Lys Ile Val Thr Gly His Val Thr Ser
                20                  25                  30
```

<210> SEQ ID NO 27
<211> LENGTH: 31
<212> TYPE: PRT
<213> ORGANISM: Artificial Sequence
<220> FEATURE:
<223> OTHER INFORMATION: recombinant peptide SP29

<400> SEQUENCE: 27

```
Lys Arg Phe Lys Asn Phe Phe Lys Ile Arg Asp Gly Ile His Glu
1               5                   10                  15

Phe Ile His Asn Asn Arg Phe Val Ile Gly Val Asn Phe Arg Phe
                20                  25                  30
```

<210> SEQ ID NO 28

```
<211> LENGTH: 31
<212> TYPE: PRT
<213> ORGANISM: Artificial Sequence
<220> FEATURE:
<223> OTHER INFORMATION: recombinant peptide SP30

<400> SEQUENCE: 28

Lys Arg Phe Lys Lys Phe Phe Lys Lys Ile Lys Asn Gly Ile Lys Thr
1               5                   10                  15

Phe Ile Lys Lys Thr Gln Met Ala Ile Gly Ser His Phe Arg Trp
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: recombinant peptide SP31

<400> SEQUENCE: 29

Lys Arg Phe Lys Asn Phe Phe Lys Arg Val Arg Asp Gly Ile Arg Asp
1               5                   10                  15

Phe Phe Arg Lys Asn His Ile Val Ile Gly Val Asn Phe Arg Phe
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: recombinant peptide SP32

<400> SEQUENCE: 30

Lys Arg Phe Leu Arg Val Phe Arg Lys Leu Lys Lys Gly Leu Lys Lys
1               5                   10                  15

Leu Phe Lys Arg Lys Lys Val Val Thr Gly Tyr Val Thr Ala
            20                  25                  30

<210> SEQ ID NO 31
<211> LENGTH: 17
<212> TYPE: PRT
<213> ORGANISM: Artificial Sequence
<220> FEATURE:
<223> OTHER INFORMATION: recombinant peptide SP33

<400> SEQUENCE: 31

Lys Arg Phe Ala Gly Phe Phe Gln Phe Val Val Gly Val Ser Phe Arg
1               5                   10                  15

Phe

<210> SEQ ID NO 32
<211> LENGTH: 17
<212> TYPE: PRT
<213> ORGANISM: Artificial Sequence
<220> FEATURE:
<223> OTHER INFORMATION: recombinant peptide SP34

<400> SEQUENCE: 32

Lys Arg Phe Val Gly Ser Phe Gln Leu Val Val Gly Val Ser Phe Arg
1               5                   10                  15

Phe

<210> SEQ ID NO 33
<211> LENGTH: 30
```

```
<212> TYPE: PRT
<213> ORGANISM: Artificial Sequence
<220> FEATURE:
<223> OTHER INFORMATION: recombinant peptide SP35

<400> SEQUENCE: 33

Lys Arg Phe Lys Lys Phe Leu Lys Lys Leu Lys Ser Val Lys Lys
1               5                   10                  15

His Val Lys Glu Phe Phe Lys Lys Pro Arg Val Ile Gly Val
            20                  25                  30

<210> SEQ ID NO 34
<211> LENGTH: 15
<212> TYPE: PRT
<213> ORGANISM: Artificial Sequence
<220> FEATURE:
<223> OTHER INFORMATION: recombinant peptide

<400> SEQUENCE: 34

Val Lys Lys Gly Val His Arg Tyr Phe Lys Lys Asn Lys Phe Tyr
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: recombinant peptide

<400> SEQUENCE: 35

Lys Val Lys Lys Gly Val His Arg Tyr Phe Lys Lys Asn Lys Phe Tyr
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: recombinant peptide'

<400> SEQUENCE: 36

Arg Lys Val Lys Lys Gly Val His Arg Tyr Phe Lys Lys Asn Lys Phe
1               5                   10                  15

Tyr

<210> SEQ ID NO 37
<211> LENGTH: 18
<212> TYPE: PRT
<213> ORGANISM: Artificial Sequence
<220> FEATURE:
<223> OTHER INFORMATION: recombinant peptide

<400> SEQUENCE: 37

Phe Arg Lys Val Lys Lys Gly Val His Arg Tyr Phe Lys Lys Asn Lys
1               5                   10                  15

Phe Tyr

<210> SEQ ID NO 38
<211> LENGTH: 19
<212> TYPE: PRT
<213> ORGANISM: Artificial Sequence
<220> FEATURE:
<223> OTHER INFORMATION: recombinant peptide

<400> SEQUENCE: 38
```

Phe Phe Arg Lys Val Lys Lys Gly Val His Arg Tyr Phe Lys Lys Asn
1               5                   10                  15

Lys Phe Tyr

<210> SEQ ID NO 39
<211> LENGTH: 20
<212> TYPE: PRT
<213> ORGANISM: Artificial Sequence
<220> FEATURE:
<223> OTHER INFORMATION: recombinant peptide

<400> SEQUENCE: 39

Lys Phe Phe Arg Lys Val Lys Lys Gly Val His Arg Tyr Phe Lys Lys
1               5                   10                  15

Asn Lys Phe Tyr
            20

<210> SEQ ID NO 40
<211> LENGTH: 21
<212> TYPE: PRT
<213> ORGANISM: Artificial Sequence
<220> FEATURE:
<223> OTHER INFORMATION: recombinant peptide'

<400> SEQUENCE: 40

Lys Lys Phe Phe Arg Lys Val Lys Lys Gly Val His Arg Tyr Phe Lys
1               5                   10                  15

Lys Asn Lys Phe Tyr
            20

<210> SEQ ID NO 41
<211> LENGTH: 22
<212> TYPE: PRT
<213> ORGANISM: Artificial Sequence
<220> FEATURE:
<223> OTHER INFORMATION: recombinant peptide

<400> SEQUENCE: 41

Phe Lys Lys Phe Phe Arg Lys Val Lys Lys Gly Val His Arg Tyr Phe
1               5                   10                  15

Lys Lys Asn Lys Phe Tyr
            20

<210> SEQ ID NO 42
<211> LENGTH: 23
<212> TYPE: PRT
<213> ORGANISM: Artificial Sequence
<220> FEATURE:
<223> OTHER INFORMATION: recombinant peptide

<400> SEQUENCE: 42

Arg Phe Lys Lys Phe Phe Arg Lys Val Lys Lys Gly Val His Arg Tyr
1               5                   10                  15

Phe Lys Lys Asn Lys Phe Tyr
            20

<210> SEQ ID NO 43
<211> LENGTH: 24
<212> TYPE: PRT
<213> ORGANISM: Artificial Sequence
<220> FEATURE:
<223> OTHER INFORMATION: recombinant peptide

<400> SEQUENCE: 43

Lys Arg Phe Lys Lys Phe Phe Arg Lys Val Lys Lys Gly Val His Arg
1               5                   10                  15

Tyr Phe Lys Lys Asn Lys Phe Tyr
            20

<210> SEQ ID NO 44
<211> LENGTH: 24
<212> TYPE: PRT
<213> ORGANISM: Artificial Sequence
<220> FEATURE:
<223> OTHER INFORMATION: SP27-64

<400> SEQUENCE: 44

Arg Phe Lys Lys Phe Phe Arg Lys Val Lys Lys Gly Val His Arg Tyr
1               5                   10                  15

Phe Lys Lys Asn Lys Phe Tyr Ile
            20

<210> SEQ ID NO 45
<211> LENGTH: 24
<212> TYPE: PRT
<213> ORGANISM: Artificial Sequence
<220> FEATURE:
<223> OTHER INFORMATION: SP27-65

<400> SEQUENCE: 45

Phe Lys Lys Phe Phe Arg Lys Val Lys Lys Gly Val His Arg Tyr Phe
1               5                   10                  15

Lys Lys Asn Lys Phe Tyr Ile Ala
            20

<210> SEQ ID NO 46
<211> LENGTH: 24
<212> TYPE: PRT
<213> ORGANISM: Artificial Sequence
<220> FEATURE:
<223> OTHER INFORMATION: SP27-66

<400> SEQUENCE: 46

Lys Lys Phe Phe Arg Lys Val Lys Lys Gly Val His Arg Tyr Phe Lys
1               5                   10                  15

Lys Asn Lys Phe Tyr Ile Ala Ala
            20

<210> SEQ ID NO 47
<211> LENGTH: 24
<212> TYPE: PRT
<213> ORGANISM: Artificial Sequence
<220> FEATURE:
<223> OTHER INFORMATION: SP27-67

<400> SEQUENCE: 47

Lys Phe Phe Arg Lys Val Lys Lys Gly Val His Arg Tyr Phe Lys Lys
1               5                   10                  15

Asn Lys Phe Tyr Ile Ala Ala Thr
            20

<210> SEQ ID NO 48
<211> LENGTH: 24
<212> TYPE: PRT
<213> ORGANISM: Artificial Sequence
<220> FEATURE:
<223> OTHER INFORMATION: SP27-68

<400> SEQUENCE: 48

Phe Phe Arg Lys Val Lys Lys Gly Val His Arg Tyr Phe Lys Lys Asn
1               5                   10                  15

Lys Phe Tyr Ile Ala Ala Thr Ile
            20

<210> SEQ ID NO 49
<211> LENGTH: 24
<212> TYPE: PRT
<213> ORGANISM: Artificial Sequence
<220> FEATURE:
<223> OTHER INFORMATION: SP27-69

<400> SEQUENCE: 49

Phe Arg Lys Val Lys Lys Gly Val His Arg Tyr Phe Lys Lys Asn Lys
1               5                   10                  15

Phe Tyr Ile Ala Ala Thr Ile Pro
            20

<210> SEQ ID NO 50
<211> LENGTH: 24
<212> TYPE: PRT
<213> ORGANISM: Artificial Sequence
<220> FEATURE:
<223> OTHER INFORMATION: SP27-70

<400> SEQUENCE: 50

Arg Lys Val Lys Lys Gly Val His Arg Tyr Phe Lys Lys Asn Lys Phe
1               5                   10                  15

Tyr Ile Ala Ala Thr Ile Pro Tyr
            20

<210> SEQ ID NO 51
<211> LENGTH: 24
<212> TYPE: PRT
<213> ORGANISM: Artificial Sequence
<220> FEATURE:
<223> OTHER INFORMATION: SP27-71

<400> SEQUENCE: 51

Lys Val Lys Lys Gly Val His Arg Tyr Phe Lys Lys Asn Lys Phe Tyr
1               5                   10                  15

Ile Ala Ala Thr Ile Pro Tyr Tyr
            20

<210> SEQ ID NO 52
<211> LENGTH: 24
<212> TYPE: PRT
<213> ORGANISM: Artificial Sequence
<220> FEATURE:
<223> OTHER INFORMATION: SP27-72

<400> SEQUENCE: 52

Val Lys Lys Gly Val His Arg Tyr Phe Lys Lys Asn Lys Phe Tyr Ile
1               5                   10                  15

Ala Ala Thr Ile Pro Tyr Tyr Gly
            20

<210> SEQ ID NO 53
<211> LENGTH: 24
<212> TYPE: PRT
<213> ORGANISM: Artificial Sequence
<220> FEATURE:
<223> OTHER INFORMATION: SP27-114

-continued

```
<400> SEQUENCE: 53

Val Lys Lys Gly Val His Arg Tyr Phe Lys Lys Asn Lys Phe Tyr Ile
1               5                   10                  15

Ala Ala Thr Ile Pro Tyr Tyr Gly
            20

<210> SEQ ID NO 54
<211> LENGTH: 15
<212> TYPE: PRT
<213> ORGANISM: Artificial Sequence
<220> FEATURE:
<223> OTHER INFORMATION: SP27-115

<400> SEQUENCE: 54

Val Lys Lys Gly Val His Arg Tyr Phe Lys Lys Asn Lys Phe Tyr
1               5                   10                  15

<210> SEQ ID NO 55
<211> LENGTH: 33
<212> TYPE: PRT
<213> ORGANISM: Artificial Sequence
<220> FEATURE:
<223> OTHER INFORMATION: SP27-1

<400> SEQUENCE: 55

Ala Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 56
<211> LENGTH: 33
<212> TYPE: PRT
<213> ORGANISM: Artificial Sequence
<220> FEATURE:
<223> OTHER INFORMATION: SP27-2

<400> SEQUENCE: 56

Lys Ala Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 57
<211> LENGTH: 33
<212> TYPE: PRT
<213> ORGANISM: Artificial Sequence
<220> FEATURE:
<223> OTHER INFORMATION: SP27-3

<400> SEQUENCE: 57

Lys Arg Ala Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 58
<211> LENGTH: 33
<212> TYPE: PRT
```

<213> ORGANISM: Artificial Sequence
<220> FEATURE:
<223> OTHER INFORMATION: SP27-4

<400> SEQUENCE: 58

Lys Arg Phe Ala Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 59
<211> LENGTH: 33
<212> TYPE: PRT
<213> ORGANISM: Artificial Sequence
<220> FEATURE:
<223> OTHER INFORMATION: SP27-5

<400> SEQUENCE: 59

Lys Arg Phe Lys Ala Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 60
<211> LENGTH: 33
<212> TYPE: PRT
<213> ORGANISM: Artificial Sequence
<220> FEATURE:
<223> OTHER INFORMATION: SP27-6

<400> SEQUENCE: 60

Lys Arg Phe Lys Lys Ala Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 61
<211> LENGTH: 33
<212> TYPE: PRT
<213> ORGANISM: Artificial Sequence
<220> FEATURE:
<223> OTHER INFORMATION: SP27-7

<400> SEQUENCE: 61

Lys Arg Phe Lys Lys Phe Ala Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 62
<211> LENGTH: 33
<212> TYPE: PRT
<213> ORGANISM: Artificial Sequence
<220> FEATURE:
<223> OTHER INFORMATION: SP27-8

<400> SEQUENCE: 62

Lys Arg Phe Lys Lys Phe Phe Ala Lys Val Lys Lys Gly Val His Arg

```
                1               5                   10                  15
Tyr Phe Lys Lys Asn Lys Phe Tyr Ile Ala Ala Thr Ile Pro Tyr Tyr
            20                  25                  30

Gly

<210> SEQ ID NO 63
<211> LENGTH: 33
<212> TYPE: PRT
<213> ORGANISM: Artificial Sequence
<220> FEATURE:
<223> OTHER INFORMATION: SP27-9

<400> SEQUENCE: 63

Lys Arg Phe Lys Lys Phe Phe Arg Ala Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 64
<211> LENGTH: 33
<212> TYPE: PRT
<213> ORGANISM: Artificial Sequence
<220> FEATURE:
<223> OTHER INFORMATION: SP27-10

<400> SEQUENCE: 64

Lys Arg Phe Lys Lys Phe Phe Arg Lys Ala Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 65
<211> LENGTH: 33
<212> TYPE: PRT
<213> ORGANISM: Artificial Sequence
<220> FEATURE:
<223> OTHER INFORMATION: SP27-11

<400> SEQUENCE: 65

Lys Arg Phe Lys Lys Phe Phe Arg Lys Val Ala Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 66
<211> LENGTH: 33
<212> TYPE: PRT
<213> ORGANISM: Artificial Sequence
<220> FEATURE:
<223> OTHER INFORMATION: SP27-12

<400> SEQUENCE: 66

Lys Arg Phe Lys Lys Phe Phe Arg Lys Val Lys Ala Gly Val His Arg
1               5                   10                  15

Tyr Phe Lys Lys Asn Lys Phe Tyr Ile Ala Ala Thr Ile Pro Tyr Tyr
            20                  25                  30

Gly
```

<210> SEQ ID NO 67
<211> LENGTH: 33
<212> TYPE: PRT
<213> ORGANISM: Artificial Sequence
<220> FEATURE:
<223> OTHER INFORMATION: SP27-13

<400> SEQUENCE: 67

Lys Arg Phe Lys Lys Phe Phe Arg Lys Val Lys Lys Ala Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 68
<211> LENGTH: 33
<212> TYPE: PRT
<213> ORGANISM: Artificial Sequence
<220> FEATURE:
<223> OTHER INFORMATION: SP27-14

<400> SEQUENCE: 68

Lys Arg Phe Lys Lys Phe Phe Arg Lys Val Lys Lys Gly Ala His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 69
<211> LENGTH: 33
<212> TYPE: PRT
<213> ORGANISM: Artificial Sequence
<220> FEATURE:
<223> OTHER INFORMATION: SP27-15

<400> SEQUENCE: 69

Lys Arg Phe Lys Lys Phe Phe Arg Lys Val Lys Lys Gly Val Ala Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 70
<211> LENGTH: 33
<212> TYPE: PRT
<213> ORGANISM: Artificial Sequence
<220> FEATURE:
<223> OTHER INFORMATION: SP27-16

<400> SEQUENCE: 70

Lys Arg Phe Lys Lys Phe Phe Arg Lys Val Lys Lys Gly Val His Ala
1               5                   10                  15

Tyr Phe Lys Lys Asn Lys Phe Tyr Ile Ala Ala Thr Ile Pro Tyr Tyr
            20                  25                  30

Gly

<210> SEQ ID NO 71
<211> LENGTH: 33
<212> TYPE: PRT
<213> ORGANISM: Artificial Sequence
<220> FEATURE:
<223> OTHER INFORMATION: SP27-17

<400> SEQUENCE: 71

Lys Arg Phe Lys Lys Phe Phe Arg Lys Val Lys Lys Gly Val His Arg
1               5                   10                  15

Ala Phe Lys Lys Asn Lys Phe Tyr Ile Ala Ala Thr Ile Pro Tyr Tyr
            20                  25                  30

Gly

<210> SEQ ID NO 72
<211> LENGTH: 33
<212> TYPE: PRT
<213> ORGANISM: Artificial Sequence
<220> FEATURE:
<223> OTHER INFORMATION: SP27-18

<400> SEQUENCE: 72

Lys Arg Phe Lys Lys Phe Phe Arg Lys Val Lys Lys Gly Val His Arg
1               5                   10                  15

Tyr Ala Lys Lys Asn Lys Phe Tyr Ile Ala Ala Thr Ile Pro Tyr Tyr
            20                  25                  30

Gly

<210> SEQ ID NO 73
<211> LENGTH: 33
<212> TYPE: PRT
<213> ORGANISM: Artificial Sequence
<220> FEATURE:
<223> OTHER INFORMATION: SP27-19

<400> SEQUENCE: 73

Lys Arg Phe Lys Lys Phe Phe Arg Lys Val Lys Lys Gly Val His Arg
1               5                   10                  15

Tyr Phe Ala Lys Asn Lys Phe Tyr Ile Ala Ala Thr Ile Pro Tyr Tyr
            20                  25                  30

Gly

<210> SEQ ID NO 74
<211> LENGTH: 33
<212> TYPE: PRT
<213> ORGANISM: Artificial Sequence
<220> FEATURE:
<223> OTHER INFORMATION: SP27-20

<400> SEQUENCE: 74

Lys Arg Phe Lys Lys Phe Phe Arg Lys Val Lys Lys Gly Val His Arg
1               5                   10                  15

Tyr Phe Lys Ala Asn Lys Phe Tyr Ile Ala Ala Thr Ile Pro Tyr Tyr
            20                  25                  30

Gly

<210> SEQ ID NO 75
<211> LENGTH: 33
<212> TYPE: PRT
<213> ORGANISM: Artificial Sequence
<220> FEATURE:
<223> OTHER INFORMATION: SP27-21

<400> SEQUENCE: 75

Lys Arg Phe Lys Lys Phe Phe Arg Lys Val Lys Lys Gly Val His Arg
1               5                   10                  15

Tyr Phe Lys Lys Ala Lys Phe Tyr Ile Ala Ala Thr Ile Pro Tyr Tyr

```
                    20                  25                  30

Gly

<210> SEQ ID NO 76
<211> LENGTH: 33
<212> TYPE: PRT
<213> ORGANISM: Artificial Sequence
<220> FEATURE:
<223> OTHER INFORMATION: SP27-22

<400> SEQUENCE: 76

Lys Arg Phe Lys Lys Phe Phe Arg Lys Val Lys Lys Gly Val His Arg
1               5                   10                  15

Tyr Phe Lys Lys Asn Ala Phe Tyr Ile Ala Ala Thr Ile Pro Tyr Tyr
                20                  25                  30

Gly

<210> SEQ ID NO 77
<211> LENGTH: 33
<212> TYPE: PRT
<213> ORGANISM: Artificial Sequence
<220> FEATURE:
<223> OTHER INFORMATION: SP27-23

<400> SEQUENCE: 77

Lys Arg Phe Lys Lys Phe Phe Arg Lys Val Lys Lys Gly Val His Arg
1               5                   10                  15

Tyr Phe Lys Lys Asn Lys Ala Tyr Ile Ala Ala Thr Ile Pro Tyr Tyr
                20                  25                  30

Gly

<210> SEQ ID NO 78
<211> LENGTH: 33
<212> TYPE: PRT
<213> ORGANISM: Artificial Sequence
<220> FEATURE:
<223> OTHER INFORMATION: SP27-24

<400> SEQUENCE: 78

Lys Arg Phe Lys Lys Phe Phe Arg Lys Val Lys Lys Gly Val His Arg
1               5                   10                  15

Tyr Phe Lys Lys Asn Lys Phe Ala Ile Ala Ala Thr Ile Pro Tyr Tyr
                20                  25                  30

Gly

<210> SEQ ID NO 79
<211> LENGTH: 33
<212> TYPE: PRT
<213> ORGANISM: Artificial Sequence
<220> FEATURE:
<223> OTHER INFORMATION: SP27-25

<400> SEQUENCE: 79

Lys Arg Phe Lys Lys Phe Phe Arg Lys Val Lys Lys Gly Val His Arg
1               5                   10                  15

Tyr Phe Lys Lys Asn Lys Phe Tyr Ala Ala Ala Thr Ile Pro Tyr Tyr
                20                  25                  30

Gly

<210> SEQ ID NO 80
<211> LENGTH: 33
```

```
<212> TYPE: PRT
<213> ORGANISM: Artificial Sequence
<220> FEATURE:
<223> OTHER INFORMATION: SP27-26

<400> SEQUENCE: 80

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Ala Ile Pro Tyr Tyr
            20                  25                  30

Gly

<210> SEQ ID NO 81
<211> LENGTH: 33
<212> TYPE: PRT
<213> ORGANISM: Artificial Sequence
<220> FEATURE:
<223> OTHER INFORMATION: SP27-27

<400> SEQUENCE: 81

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ala Pro Tyr Tyr
            20                  25                  30

Gly

<210> SEQ ID NO 82
<211> LENGTH: 33
<212> TYPE: PRT
<213> ORGANISM: Artificial Sequence
<220> FEATURE:
<223> OTHER INFORMATION: SP27-28

<400> SEQUENCE: 82

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Ala Tyr Tyr
            20                  25                  30

Gly

<210> SEQ ID NO 83
<211> LENGTH: 33
<212> TYPE: PRT
<213> ORGANISM: Artificial Sequence
<220> FEATURE:
<223> OTHER INFORMATION: SP27-29

<400> SEQUENCE: 83

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Ala Tyr
            20                  25                  30

Gly

<210> SEQ ID NO 84
<211> LENGTH: 33
<212> TYPE: PRT
<213> ORGANISM: Artificial Sequence
<220> FEATURE:
<223> OTHER INFORMATION: SP27-30

<400> SEQUENCE: 84
```

```
Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Ala
            20                  25                  30

Gly

<210> SEQ ID NO 85
<211> LENGTH: 33
<212> TYPE: PRT
<213> ORGANISM: Artificial Sequence
<220> FEATURE:
<223> OTHER INFORMATION: SP27-31

<400> SEQUENCE: 85

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Ala

<210> SEQ ID NO 86
<211> LENGTH: 33
<212> TYPE: PRT
<213> ORGANISM: Artificial Sequence
<220> FEATURE:
<223> OTHER INFORMATION: SP27-RI

<400> SEQUENCE: 86

Gly Tyr Tyr Pro Ile Thr Ala Ala Ile Tyr Phe Lys Asn Lys Lys Phe
1               5                   10                  15

Tyr Arg His Val Gly Lys Lys Val Lys Arg Phe Phe Lys Lys Phe Arg
            20                  25                  30

Lys

<210> SEQ ID NO 87
<211> LENGTH: 34
<212> TYPE: PRT
<213> ORGANISM: Artificial Sequence
<220> FEATURE:
<223> OTHER INFORMATION: SP27-PEG2
<220> FEATURE:
<221> NAME/KEY: MISC_FEATURE
<222> LOCATION: (34)..(34)
<223> OTHER INFORMATION: X is Fmoc-NH-(PEG)2-COOH
<220> FEATURE:
<221> NAME/KEY: MISC_FEATURE
<222> LOCATION: (35)..(35)
<223> OTHER INFORMATION: B is amide

<400> SEQUENCE: 87

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly Xaa

<210> SEQ ID NO 88
<211> LENGTH: 34
<212> TYPE: PRT
<213> ORGANISM: Artificial Sequence
<220> FEATURE:
<223> OTHER INFORMATION: SP27-PEG3
<220> FEATURE:
<221> NAME/KEY: MISC_FEATURE
```

```
<222> LOCATION: (34)..(34)
<223> OTHER INFORMATION: X is Fmoc-NH-(PEG)3-COOH
<220> FEATURE:
<221> NAME/KEY: MISC_FEATURE
<222> LOCATION: (35)..(35)
<223> OTHER INFORMATION: B is amide

<400> SEQUENCE: 88

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly Xaa

<210> SEQ ID NO 89
<211> LENGTH: 34
<212> TYPE: PRT
<213> ORGANISM: Artificial Sequence
<220> FEATURE:
<223> OTHER INFORMATION: SP27-PEG5
<220> FEATURE:
<221> NAME/KEY: MISC_FEATURE
<222> LOCATION: (34)..(34)
<223> OTHER INFORMATION: X is Fmoc-NH-(PEG)5-COOH
<220> FEATURE:
<221> NAME/KEY: MISC_FEATURE
<222> LOCATION: (35)..(35)
<223> OTHER INFORMATION: B is amide

<400> SEQUENCE: 89

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly Xaa

<210> SEQ ID NO 90
<211> LENGTH: 34
<212> TYPE: PRT
<213> ORGANISM: Artificial Sequence
<220> FEATURE:
<223> OTHER INFORMATION: SP27-PEG11
<220> FEATURE:
<221> NAME/KEY: MISC_FEATURE
<222> LOCATION: (34)..(34)
<223> OTHER INFORMATION: X is Fmoc-NH-(PEG)11-COOH
<220> FEATURE:
<221> NAME/KEY: MISC_FEATURE
<222> LOCATION: (35)..(35)
<223> OTHER INFORMATION: B is amide

<400> SEQUENCE: 90

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly Xaa

<210> SEQ ID NO 91
<211> LENGTH: 34
<212> TYPE: PRT
<213> ORGANISM: Artificial Sequence
<220> FEATURE:
<223> OTHER INFORMATION: SP27-PEG27
<220> FEATURE:
<221> NAME/KEY: MISC_FEATURE
<222> LOCATION: (34)..(34)
```

<223> OTHER INFORMATION: X is Fmoc-NH-(PEG)27-COOH
<220> FEATURE:
<221> NAME/KEY: MISC_FEATURE
<222> LOCATION: (35)..(35)
<223> OTHER INFORMATION: B is amide

<400> SEQUENCE: 91

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly Xaa

<210> SEQ ID NO 92
<211> LENGTH: 34
<212> TYPE: PRT
<213> ORGANISM: Artificial Sequence
<220> FEATURE:
<223> OTHER INFORMATION: PEG2-SP27
<220> FEATURE:
<221> NAME/KEY: MISC_FEATURE
<222> LOCATION: (1)..(1)
<223> OTHER INFORMATION: X is Fmoc-NH-(PEG)2-COOH

<400> SEQUENCE: 92

Xaa Lys Arg Phe Lys Lys Phe Phe Arg Lys Val Lys Lys Gly Val His
1               5                   10                  15

Arg Tyr Phe Lys Lys Asn Lys Phe Tyr Ile Ala Ala Thr Ile Pro Tyr
            20                  25                  30

Tyr Gly

<210> SEQ ID NO 93
<211> LENGTH: 34
<212> TYPE: PRT
<213> ORGANISM: Artificial Sequence
<220> FEATURE:
<223> OTHER INFORMATION: PEG3-SP27
<220> FEATURE:
<221> NAME/KEY: MISC_FEATURE
<222> LOCATION: (1)..(1)
<223> OTHER INFORMATION: X is Fmoc-NH-(PEG)3-COOH

<400> SEQUENCE: 93

Xaa Lys Arg Phe Lys Lys Phe Phe Arg Lys Val Lys Lys Gly Val His
1               5                   10                  15

Arg Tyr Phe Lys Lys Asn Lys Phe Tyr Ile Ala Ala Thr Ile Pro Tyr
            20                  25                  30

Tyr Gly

<210> SEQ ID NO 94
<211> LENGTH: 34
<212> TYPE: PRT
<213> ORGANISM: Artificial Sequence
<220> FEATURE:
<223> OTHER INFORMATION: PEG5-SP27
<220> FEATURE:
<221> NAME/KEY: MISC_FEATURE
<222> LOCATION: (1)..(1)
<223> OTHER INFORMATION: X is Fmoc-NH-(PEG)5-COOH

<400> SEQUENCE: 94

Xaa Lys Arg Phe Lys Lys Phe Phe Arg Lys Val Lys Lys Gly Val His
1               5                   10                  15

Arg Tyr Phe Lys Lys Asn Lys Phe Tyr Ile Ala Ala Thr Ile Pro Tyr
            20                  25                  30

```
<210> SEQ ID NO 95
<211> LENGTH: 34
<212> TYPE: PRT
<213> ORGANISM: Artificial Sequence
<220> FEATURE:
<223> OTHER INFORMATION: PEG11-SP27
<220> FEATURE:
<221> NAME/KEY: MISC_FEATURE
<222> LOCATION: (1)..(1)
<223> OTHER INFORMATION: X is Fmoc-NH-(PEG)11-COOH

<400> SEQUENCE: 95

Xaa Lys Arg Phe Lys Lys Phe Phe Arg Lys Val Lys Lys Gly Val His
 1               5                  10                  15

Arg Tyr Phe Lys Lys Asn Lys Phe Tyr Ile Ala Ala Thr Ile Pro Tyr
            20                  25                  30

Tyr Gly

<210> SEQ ID NO 96
<211> LENGTH: 34
<212> TYPE: PRT
<213> ORGANISM: Artificial Sequence
<220> FEATURE:
<223> OTHER INFORMATION: PEG27-SP27
<220> FEATURE:
<221> NAME/KEY: MISC_FEATURE
<222> LOCATION: (1)..(1)
<223> OTHER INFORMATION: X is Fmoc-NH-(PEG)27-COOH

<400> SEQUENCE: 96

Xaa Lys Arg Phe Lys Lys Phe Phe Arg Lys Val Lys Lys Gly Val His
 1               5                  10                  15

Arg Tyr Phe Lys Lys Asn Lys Phe Tyr Ile Ala Ala Thr Ile Pro Tyr
            20                  25                  30

Tyr Gly

<210> SEQ ID NO 97
<211> LENGTH: 25
<212> TYPE: PRT
<213> ORGANISM: Artificial Sequence
<220> FEATURE:
<223> OTHER INFORMATION: SP27-63-PEG2
<220> FEATURE:
<221> NAME/KEY: MISC_FEATURE
<222> LOCATION: (25)..(25)
<223> OTHER INFORMATION: X is Fmoc-NH-(PEG)2-COOH
<220> FEATURE:
<221> NAME/KEY: MISC_FEATURE
<222> LOCATION: (26)..(26)
<223> OTHER INFORMATION: B is amide

<400> SEQUENCE: 97

Lys Arg Phe Lys Lys Phe Phe Arg Lys Val Lys Lys Gly Val His Arg
 1               5                  10                  15

Tyr Phe Lys Lys Asn Lys Phe Tyr Xaa
            20                  25

<210> SEQ ID NO 98
<211> LENGTH: 25
<212> TYPE: PRT
<213> ORGANISM: Artificial Sequence
<220> FEATURE:
<223> OTHER INFORMATION: SP27-63-PEG3
<220> FEATURE:
```

```
<221> NAME/KEY: MISC_FEATURE
<222> LOCATION: (25)..(25)
<223> OTHER INFORMATION: X is Fmoc-NH-(PEG)3-COOH
<220> FEATURE:
<221> NAME/KEY: MISC_FEATURE
<222> LOCATION: (26)..(26)
<223> OTHER INFORMATION: B is amide

<400> SEQUENCE: 98

Lys Arg Phe Lys Lys Phe Phe Arg Lys Val Lys Lys Gly Val His Arg
1               5                   10                  15

Tyr Phe Lys Lys Asn Lys Phe Tyr Xaa
            20                  25

<210> SEQ ID NO 99
<211> LENGTH: 25
<212> TYPE: PRT
<213> ORGANISM: Artificial Sequence
<220> FEATURE:
<223> OTHER INFORMATION: SP27-63-PEG5
<220> FEATURE:
<221> NAME/KEY: MISC_FEATURE
<222> LOCATION: (25)..(25)
<223> OTHER INFORMATION: X is Fmoc-NH-(PEG)5-COOH
<220> FEATURE:
<221> NAME/KEY: MISC_FEATURE
<222> LOCATION: (26)..(26)
<223> OTHER INFORMATION: B is amide

<400> SEQUENCE: 99

Lys Arg Phe Lys Lys Phe Phe Arg Lys Val Lys Lys Gly Val His Arg
1               5                   10                  15

Tyr Phe Lys Lys Asn Lys Phe Tyr Xaa
            20                  25

<210> SEQ ID NO 100
<211> LENGTH: 25
<212> TYPE: PRT
<213> ORGANISM: Artificial Sequence
<220> FEATURE:
<223> OTHER INFORMATION: SP27-63-PEG11
<220> FEATURE:
<221> NAME/KEY: MISC_FEATURE
<222> LOCATION: (25)..(25)
<223> OTHER INFORMATION: X is Fmoc-NH-(PEG)11-COOH
<220> FEATURE:
<221> NAME/KEY: MISC_FEATURE
<222> LOCATION: (26)..(26)
<223> OTHER INFORMATION: B is amide

<400> SEQUENCE: 100

Lys Arg Phe Lys Lys Phe Phe Arg Lys Val Lys Lys Gly Val His Arg
1               5                   10                  15

Tyr Phe Lys Lys Asn Lys Phe Tyr Xaa
            20                  25

<210> SEQ ID NO 101
<211> LENGTH: 25
<212> TYPE: PRT
<213> ORGANISM: Artificial Sequence
<220> FEATURE:
<223> OTHER INFORMATION: SP27-63-PEG27
<220> FEATURE:
<221> NAME/KEY: MISC_FEATURE
<222> LOCATION: (25)..(25)
<223> OTHER INFORMATION: X is Fmoc-NH-(PEG)27-COOH
<220> FEATURE:
<221> NAME/KEY: MISC_FEATURE
<222> LOCATION: (26)..(26)
<223> OTHER INFORMATION: B is amide
```

<400> SEQUENCE: 101

Lys Arg Phe Lys Lys Phe Phe Arg Lys Val Lys Gly Val His Arg
1               5                   10                  15

Tyr Phe Lys Lys Asn Lys Phe Tyr Xaa
            20                  25

<210> SEQ ID NO 102
<211> LENGTH: 25
<212> TYPE: PRT
<213> ORGANISM: Artificial Sequence
<220> FEATURE:
<223> OTHER INFORMATION: PEG2-SP27-63
<220> FEATURE:
<221> NAME/KEY: MISC_FEATURE
<222> LOCATION: (1)..(1)
<223> OTHER INFORMATION: X is Fmoc-NH-(PEG)2-COOH

<400> SEQUENCE: 102

Xaa Lys Arg Phe Lys Lys Phe Phe Arg Lys Val Lys Lys Gly Val His
1               5                   10                  15

Arg Tyr Phe Lys Lys Asn Lys Phe Tyr
            20                  25

<210> SEQ ID NO 103
<211> LENGTH: 25
<212> TYPE: PRT
<213> ORGANISM: Artificial Sequence
<220> FEATURE:
<223> OTHER INFORMATION: PEG3-SP27-63
<220> FEATURE:
<221> NAME/KEY: MISC_FEATURE
<222> LOCATION: (1)..(1)
<223> OTHER INFORMATION: X is Fmoc-NH-(PEG)3-COOH

<400> SEQUENCE: 103

Xaa Lys Arg Phe Lys Lys Phe Phe Arg Lys Val Lys Lys Gly Val His
1               5                   10                  15

Arg Tyr Phe Lys Lys Asn Lys Phe Tyr
            20                  25

<210> SEQ ID NO 104
<211> LENGTH: 25
<212> TYPE: PRT
<213> ORGANISM: Artificial Sequence
<220> FEATURE:
<223> OTHER INFORMATION: PEG5-SP27-63
<220> FEATURE:
<221> NAME/KEY: MISC_FEATURE
<222> LOCATION: (1)..(1)
<223> OTHER INFORMATION: X is Fmoc-NH-(PEG)5-COOH

<400> SEQUENCE: 104

Xaa Lys Arg Phe Lys Lys Phe Phe Arg Lys Val Lys Lys Gly Val His
1               5                   10                  15

Arg Tyr Phe Lys Lys Asn Lys Phe Tyr
            20                  25

<210> SEQ ID NO 105
<211> LENGTH: 25
<212> TYPE: PRT
<213> ORGANISM: Artificial Sequence
<220> FEATURE:
<223> OTHER INFORMATION: PEG11-SP27-63
<220> FEATURE:
<221> NAME/KEY: MISC_FEATURE
<222> LOCATION: (1)..(1)

<223> OTHER INFORMATION: X is Fmoc-NH-(PEG)11-COOH

<400> SEQUENCE: 105

Xaa Lys Arg Phe Lys Lys Phe Phe Arg Lys Val Lys Lys Gly Val His
1               5                   10                  15

Arg Tyr Phe Lys Lys Asn Lys Phe Tyr
            20                  25

<210> SEQ ID NO 106
<211> LENGTH: 25
<212> TYPE: PRT
<213> ORGANISM: Artificial Sequence
<220> FEATURE:
<223> OTHER INFORMATION: PEG27-SP27-63
<220> FEATURE:
<221> NAME/KEY: MISC_FEATURE
<222> LOCATION: (1)..(1)
<223> OTHER INFORMATION: X is Fmoc-NH-(PEG)27-COOH

<400> SEQUENCE: 106

Xaa Lys Arg Phe Lys Lys Phe Phe Arg Lys Val Lys Lys Gly Val His
1               5                   10                  15

Arg Tyr Phe Lys Lys Asn Lys Phe Tyr
            20                  25

<210> SEQ ID NO 107
<211> LENGTH: 33
<212> TYPE: PRT
<213> ORGANISM: Artificial Sequence
<220> FEATURE:
<223> OTHER INFORMATION: SP27-73
<220> FEATURE:
<221> NAME/KEY: MISC_FEATURE
<222> LOCATION: (1)..(1)
<223> OTHER INFORMATION: X is homolysine

<400> SEQUENCE: 107

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 108
<211> LENGTH: 33
<212> TYPE: PRT
<213> ORGANISM: Artificial Sequence
<220> FEATURE:
<223> OTHER INFORMATION: SP27-74
<220> FEATURE:
<221> NAME/KEY: MISC_FEATURE
<222> LOCATION: (1)..(1)
<223> OTHER INFORMATION: X is e-Methyl lysine (Lys(Me))

<400> SEQUENCE: 108

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 109
<211> LENGTH: 33
<212> TYPE: PRT
<213> ORGANISM: Artificial Sequence
<220> FEATURE:
<223> OTHER INFORMATION: SP27-75
<220> FEATURE:
<221> NAME/KEY: MISC_FEATURE
<222> LOCATION: (1)..(1)
<223> OTHER INFORMATION: X is e,e -Dimethyl lysine (Lys(Me)2)

<400> SEQUENCE: 109

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 110
<211> LENGTH: 33
<212> TYPE: PRT
<213> ORGANISM: Artificial Sequence
<220> FEATURE:
<223> OTHER INFORMATION: SP27-76
<220> FEATURE:
<221> NAME/KEY: MISC_FEATURE
<222> LOCATION: (1)..(1)
<223> OTHER INFORMATION: X is e, e, e-Trimethyl lysine (Lys(Me)3)

<400> SEQUENCE: 110

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 111
<211> LENGTH: 33
<212> TYPE: PRT
<213> ORGANISM: Artificial Sequence
<220> FEATURE:
<223> OTHER INFORMATION: SP27-77
<220> FEATURE:
<221> NAME/KEY: MOD_RES
<222> LOCATION: (1)..(1)
<223> OTHER INFORMATION: Orn

<400> SEQUENCE: 111

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 112
<211> LENGTH: 33
<212> TYPE: PRT
<213> ORGANISM: Artificial Sequence
<220> FEATURE:
<223> OTHER INFORMATION: SP27-78
<220> FEATURE:
<221> NAME/KEY: MOD_RES
<222> LOCATION: (1)..(1)
<223> OTHER INFORMATION: Dpr

<400> SEQUENCE: 112

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr

Gly

<210> SEQ ID NO 113
<211> LENGTH: 33
<212> TYPE: PRT
<213> ORGANISM: Artificial Sequence
<220> FEATURE:
<223> OTHER INFORMATION: SP27-79
<220> FEATURE:
<221> NAME/KEY: MISC_FEATURE
<222> LOCATION: (1)..(1)
<223> OTHER INFORMATION: X is 2,4-Diaminobutanoic acid (Dab)

<400> SEQUENCE: 113

Xaa Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 114
<211> LENGTH: 33
<212> TYPE: PRT
<213> ORGANISM: Artificial Sequence
<220> FEATURE:
<223> OTHER INFORMATION: SP27-80
<220> FEATURE:
<221> NAME/KEY: MISC_FEATURE
<222> LOCATION: (2)..(2)
<223> OTHER INFORMATION: X is homoarginine (hArg)

<400> SEQUENCE: 114

Lys Xaa Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 115
<211> LENGTH: 33
<212> TYPE: PRT
<213> ORGANISM: Artificial Sequence
<220> FEATURE:
<223> OTHER INFORMATION: SP27-81
<220> FEATURE:
<221> NAME/KEY: MISC_FEATURE
<222> LOCATION: (2)..(2)
<223> OTHER INFORMATION: X is Methylarginine (Arg(Me))

<400> SEQUENCE: 115

Lys Xaa Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 116
<211> LENGTH: 33
<212> TYPE: PRT
<213> ORGANISM: Artificial Sequence
<220> FEATURE:
<223> OTHER INFORMATION: SP27-82
<220> FEATURE:
<221> NAME/KEY: MISC_FEATURE
<222> LOCATION: (2)..(2)
<223> OTHER INFORMATION: X is Asym. dimethylarginine (ADMA)

<400> SEQUENCE: 116

Lys Xaa Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 117
<211> LENGTH: 33
<212> TYPE: PRT
<213> ORGANISM: Artificial Sequence
<220> FEATURE:
<223> OTHER INFORMATION: SP27-83
<220> FEATURE:
<221> NAME/KEY: MISC_FEATURE
<222> LOCATION: (2)..(2)
<223> OTHER INFORMATION: X is Shortend Arg (Agb)

<400> SEQUENCE: 117

Lys Xaa Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 118
<211> LENGTH: 33
<212> TYPE: PRT
<213> ORGANISM: Artificial Sequence
<220> FEATURE:
<223> OTHER INFORMATION: SP27-84
<220> FEATURE:
<221> NAME/KEY: MISC_FEATURE
<222> LOCATION: (2)..(2)
<223> OTHER INFORMATION: X is Citrulline (Cit)

<400> SEQUENCE: 118

Lys Xaa Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 119
<211> LENGTH: 33
<212> TYPE: PRT
<213> ORGANISM: Artificial Sequence
<220> FEATURE:
<223> OTHER INFORMATION: SP27-85
<220> FEATURE:
<221> NAME/KEY: MISC_FEATURE
<222> LOCATION: (3)..(3)
<223> OTHER INFORMATION: X is Homophenylalanine (hPhe)

<400> SEQUENCE: 119

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 120
<211> LENGTH: 33
<212> TYPE: PRT
<213> ORGANISM: Artificial Sequence
<220> FEATURE:
<223> OTHER INFORMATION: SP27-86
<220> FEATURE:
<221> NAME/KEY: MISC_FEATURE
<222> LOCATION: (3)..(3)
<223> OTHER INFORMATION: X is Homotyrosine (hTyr)

<400> SEQUENCE: 120

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 121
<211> LENGTH: 33
<212> TYPE: PRT
<213> ORGANISM: Artificial Sequence
<220> FEATURE:
<223> OTHER INFORMATION: SP27-87
<220> FEATURE:
<221> NAME/KEY: MISC_FEATURE
<222> LOCATION: (3)..(3)
<223> OTHER INFORMATION: X is Phenylglycine (Phg)

<400> SEQUENCE: 121

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 122
<211> LENGTH: 33
<212> TYPE: PRT
<213> ORGANISM: Artificial Sequence
<220> FEATURE:
<223> OTHER INFORMATION: SP27-88
<220> FEATURE:
<221> NAME/KEY: MISC_FEATURE
<222> LOCATION: (3)..(3)
<223> OTHER INFORMATION: X is 4-Fluorophenylalanine (Phe(4-F))

<400> SEQUENCE: 122

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 123
<211> LENGTH: 33
<212> TYPE: PRT
<213> ORGANISM: Artificial Sequence
<220> FEATURE:
<223> OTHER INFORMATION: SP27-89
<220> FEATURE:
<221> NAME/KEY: MISC_FEATURE
<222> LOCATION: (3)..(3)
<223> OTHER INFORMATION: X is 4-Chlorophenylalanine (Phe(4-Cl))

<400> SEQUENCE: 123

```
Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 124
<211> LENGTH: 33
<212> TYPE: PRT
<213> ORGANISM: Artificial Sequence
<220> FEATURE:
<223> OTHER INFORMATION: SP27-90
<220> FEATURE:
<221> NAME/KEY: MISC_FEATURE
<222> LOCATION: (3)..(3)
<223> OTHER INFORMATION: X is 4-Cyanophenylalanine (Phe(4-CN))

<400> SEQUENCE: 124

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 125
<211> LENGTH: 33
<212> TYPE: PRT
<213> ORGANISM: Artificial Sequence
<220> FEATURE:
<223> OTHER INFORMATION: SP27-91
<220> FEATURE:
<221> NAME/KEY: MISC_FEATURE
<222> LOCATION: (3)..(3)
<223> OTHER INFORMATION: X is 4-Nitrophenylalanine (Phe(4-NO2))

<400> SEQUENCE: 125

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 126
<211> LENGTH: 33
<212> TYPE: PRT
<213> ORGANISM: Artificial Sequence
<220> FEATURE:
<223> OTHER INFORMATION: SP27-92
<220> FEATURE:
<221> NAME/KEY: MISC_FEATURE
<222> LOCATION: (3)..(3)
<223> OTHER INFORMATION: X is Cyclohexylalanine (Cha)

<400> SEQUENCE: 126

Lys Arg Xaa Lys Lys Phe Phe Arg Lys Val Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 127
<211> LENGTH: 33
<212> TYPE: PRT
```

```
<213> ORGANISM: Artificial Sequence
<220> FEATURE:
<223> OTHER INFORMATION: SP27-93
<220> FEATURE:
<221> NAME/KEY: MOD_RES
<222> LOCATION: (10)..(10)
<223> OTHER INFORMATION: Nva

<400> SEQUENCE: 127
```

Lys Arg Phe Lys Lys Phe Phe Arg Lys Xaa Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

```
<210> SEQ ID NO 128
<211> LENGTH: 33
<212> TYPE: PRT
<213> ORGANISM: Artificial Sequence
<220> FEATURE:
<223> OTHER INFORMATION: SP27-94
<220> FEATURE:
<221> NAME/KEY: MISC_FEATURE
<222> LOCATION: (10)..(10)
<223> OTHER INFORMATION: X is homoleucine (hLeu)

<400> SEQUENCE: 128
```

Lys Arg Phe Lys Lys Phe Phe Arg Lys Xaa Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

```
<210> SEQ ID NO 129
<211> LENGTH: 33
<212> TYPE: PRT
<213> ORGANISM: Artificial Sequence
<220> FEATURE:
<223> OTHER INFORMATION: SP27-95
<220> FEATURE:
<221> NAME/KEY: MOD_RES
<222> LOCATION: (10)..(10)
<223> OTHER INFORMATION: Nle

<400> SEQUENCE: 129
```

Lys Arg Phe Lys Lys Phe Phe Arg Lys Xaa Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

```
<210> SEQ ID NO 130
<211> LENGTH: 33
<212> TYPE: PRT
<213> ORGANISM: Artificial Sequence
<220> FEATURE:
<223> OTHER INFORMATION: SP27-96
<220> FEATURE:
<221> NAME/KEY: MOD_RES
<222> LOCATION: (10)..(10)
<223> OTHER INFORMATION: Abu

<400> SEQUENCE: 130
```

Lys Arg Phe Lys Lys Phe Phe Arg Lys Xaa Lys Lys Gly Val His Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 131
<211> LENGTH: 33
<212> TYPE: PRT
<213> ORGANISM: Artificial Sequence
<220> FEATURE:
<223> OTHER INFORMATION: SP27-97
<220> FEATURE:
<221> NAME/KEY: MISC_FEATURE
<222> LOCATION: (15)..(15)
<223> OTHER INFORMATION: X is 1-Methylhistidine (His(1-Me)

<400> SEQUENCE: 131

Lys Arg Phe Lys Lys Phe Phe Arg Lys Val Lys Lys Gly Val Xaa Arg
1               5                   10                  15

Tyr Phe Lys Lys Asn Lys Phe Tyr Ile Ala Ala Thr Ile Pro Tyr Tyr
            20                  25                  30

Gly

<210> SEQ ID NO 132
<211> LENGTH: 33
<212> TYPE: PRT
<213> ORGANISM: Artificial Sequence
<220> FEATURE:
<223> OTHER INFORMATION: SP27-98
<220> FEATURE:
<221> NAME/KEY: MISC_FEATURE
<222> LOCATION: (17)..(17)
<223> OTHER INFORMATION: X is 3-Methylhistidine (His(3-Me)

<400> SEQUENCE: 132

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

<210> SEQ ID NO 133
<211> LENGTH: 33
<212> TYPE: PRT
<213> ORGANISM: Artificial Sequence
<220> FEATURE:
<223> OTHER INFORMATION: SP27-99
<220> FEATURE:
<221> NAME/KEY: MISC_FEATURE
<222> LOCATION: (17)..(17)
<223> OTHER INFORMATION: X is O-Methyltyrosine (Tyr(OMe))

<400> SEQUENCE: 133

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

<210> SEQ ID NO 134
<211> LENGTH: 33
<212> TYPE: PRT
<213> ORGANISM: Artificial Sequence
<220> FEATURE:
<223> OTHER INFORMATION: SP27-100
<220> FEATURE:

<221> NAME/KEY: MISC_FEATURE
<222> LOCATION: (17)..(17)
<223> OTHER INFORMATION: X is Homotyrosine (hTyr)

<400> SEQUENCE: 134

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

<210> SEQ ID NO 135
<211> LENGTH: 33
<212> TYPE: PRT
<213> ORGANISM: Artificial Sequence
<220> FEATURE:
<223> OTHER INFORMATION: SP27-101
<220> FEATURE:
<221> NAME/KEY: MISC_FEATURE
<222> LOCATION: (17)..(17)
<223> OTHER INFORMATION: X is Homophenylalanine (hPhe)

<400> SEQUENCE: 135

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

<210> SEQ ID NO 136
<211> LENGTH: 33
<212> TYPE: PRT
<213> ORGANISM: Artificial Sequence
<220> FEATURE:
<223> OTHER INFORMATION: SP27-102
<220> FEATURE:
<221> NAME/KEY: MISC_FEATURE
<222> LOCATION: (17)..(17)
<223> OTHER INFORMATION: X is 4-Fluorophenylalanine (Phe(4-F))

<400> SEQUENCE: 136

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

<210> SEQ ID NO 137
<211> LENGTH: 33
<212> TYPE: PRT
<213> ORGANISM: Artificial Sequence
<220> FEATURE:
<223> OTHER INFORMATION: SP27-103
<220> FEATURE:
<221> NAME/KEY: MISC_FEATURE
<222> LOCATION: (17)..(17)
<223> OTHER INFORMATION: X is 4-Chlorophenylalanine (Phe(4-Cl))

<400> SEQUENCE: 137

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

```
<210> SEQ ID NO 138
<211> LENGTH: 33
<212> TYPE: PRT
<213> ORGANISM: Artificial Sequence
<220> FEATURE:
<223> OTHER INFORMATION: SP27-104
<220> FEATURE:
<221> NAME/KEY: MISC_FEATURE
<222> LOCATION: (17)..(17)
<223> OTHER INFORMATION: X is 4-Cyanophenylalanine (Phe(4-CN))

<400> SEQUENCE: 138
```

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

```
<210> SEQ ID NO 139
<211> LENGTH: 33
<212> TYPE: PRT
<213> ORGANISM: Artificial Sequence
<220> FEATURE:
<223> OTHER INFORMATION: SP27-105
<220> FEATURE:
<221> NAME/KEY: MISC_FEATURE
<222> LOCATION: (17)..(17)
<223> OTHER INFORMATION: X is 4-Nitrophenylalanine (Phe(4-NO2))

<400> SEQUENCE: 139
```

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

```
<210> SEQ ID NO 140
<211> LENGTH: 33
<212> TYPE: PRT
<213> ORGANISM: Artificial Sequence
<220> FEATURE:
<223> OTHER INFORMATION: SP27-106
<220> FEATURE:
<221> NAME/KEY: MISC_FEATURE
<222> LOCATION: (17)..(17)
<223> OTHER INFORMATION: X is Dihydroxyphenylalanine (DOPA)

<400> SEQUENCE: 140
```

Lys Arg Phe Lys Lys Phe Phe Arg Lys Val Lys Lys Gly Val His Arg
1               5                   10                  15

Xaa Phe Lys Lys Asn Lys Phe Tyr Ile Ala Ala Thr Ile Pro Tyr Tyr
            20                  25                  30

Gly

```
<210> SEQ ID NO 141
<211> LENGTH: 33
<212> TYPE: PRT
<213> ORGANISM: Artificial Sequence
<220> FEATURE:
<223> OTHER INFORMATION: SP27-107
<220> FEATURE:
<221> NAME/KEY: MOD_RES
<222> LOCATION: (25)..(25)
<223> OTHER INFORMATION: Nva
```

<400> SEQUENCE: 141

Lys Arg Phe Lys Lys Phe Phe Arg Lys Val Lys Lys Gly Val His Arg
1               5                   10                  15

Tyr Phe Lys Lys Asn Lys Phe Tyr Xaa Ala Ala Thr Ile Pro Tyr Tyr
            20                  25                  30

Gly

<210> SEQ ID NO 142
<211> LENGTH: 33
<212> TYPE: PRT
<213> ORGANISM: Artificial Sequence
<220> FEATURE:
<223> OTHER INFORMATION: SP27-108
<220> FEATURE:
<221> NAME/KEY: MISC_FEATURE
<222> LOCATION: (25)..(25)
<223> OTHER INFORMATION: Homoleucine (hLeu)

<400> SEQUENCE: 142

Lys Arg Phe Lys Lys Phe Phe Arg Lys Val Lys Lys Gly Val His Arg
1               5                   10                  15

Tyr Phe Lys Lys Asn Lys Phe Tyr Xaa Ala Ala Thr Ile Pro Tyr Tyr
            20                  25                  30

Gly

<210> SEQ ID NO 143
<211> LENGTH: 33
<212> TYPE: PRT
<213> ORGANISM: Artificial Sequence
<220> FEATURE:
<223> OTHER INFORMATION: SP27-109
<220> FEATURE:
<221> NAME/KEY: MOD_RES
<222> LOCATION: (25)..(25)
<223> OTHER INFORMATION: Nle

<400> SEQUENCE: 143

Lys Arg Phe Lys Lys Phe Phe Arg Lys Val Lys Lys Gly Val His Arg
1               5                   10                  15

Tyr Phe Lys Lys Asn Lys Phe Tyr Xaa Ala Ala Thr Ile Pro Tyr Tyr
            20                  25                  30

Gly

<210> SEQ ID NO 144
<211> LENGTH: 33
<212> TYPE: PRT
<213> ORGANISM: Artificial Sequence
<220> FEATURE:
<223> OTHER INFORMATION: SP27-110
<220> FEATURE:
<221> NAME/KEY: MOD_RES
<222> LOCATION: (25)..(25)
<223> OTHER INFORMATION: Abu

<400> SEQUENCE: 144

Lys Arg Phe Lys Lys Phe Phe Arg Lys Val Lys Lys Gly Val His Arg
1               5                   10                  15

Tyr Phe Lys Lys Asn Lys Phe Tyr Xaa Ala Ala Thr Ile Pro Tyr Tyr
            20                  25                  30

Gly

<210> SEQ ID NO 145
<211> LENGTH: 33

```
<212> TYPE: PRT
<213> ORGANISM: Artificial Sequence
<220> FEATURE:
<223> OTHER INFORMATION: SP27-111
<220> FEATURE:
<221> NAME/KEY: MISC_FEATURE
<222> LOCATION: (30)..(30)
<223> OTHER INFORMATION: X is Hydroxyproline (Hyp)

<400> SEQUENCE: 145

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Xaa Tyr Tyr
            20                  25                  30

Gly

<210> SEQ ID NO 146
<211> LENGTH: 33
<212> TYPE: PRT
<213> ORGANISM: Artificial Sequence
<220> FEATURE:
<223> OTHER INFORMATION: SP27-112
<220> FEATURE:
<221> NAME/KEY: MISC_FEATURE
<222> LOCATION: (30)..(30)
<223> OTHER INFORMATION: X is Isonipecotic acid (Isn)

<400> SEQUENCE: 146

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Xaa Tyr Tyr
            20                  25                  30

Gly

<210> SEQ ID NO 147
<211> LENGTH: 33
<212> TYPE: PRT
<213> ORGANISM: Artificial Sequence
<220> FEATURE:
<223> OTHER INFORMATION: SP27-113
<220> FEATURE:
<221> NAME/KEY: MISC_FEATURE
<222> LOCATION: (30)..(30)
<223> OTHER INFORMATION: X is Thiaproline (Thz)

<400> SEQUENCE: 147

Lys Arg Phe Lys Lys Phe Phe Arg Lys Val Lys Lys Gly Val His Arg
1               5                   10                  15

Tyr Phe Lys Lys Asn Lys Phe Tyr Ile Ala Ala Thr Ile Xaa Tyr Tyr
            20                  25                  30

Gly
```

BIOACTIVE PEPTIDES DERIVED FROM SNAKES

CROSS-REFERENCE TO RELATED APPLICATIONS

This application is a national phase entry under 35 U.S.C. § 371 of International Patent Application PCT/NL2019/050612, filed Sep. 17, 2019, designating the United States of America and published as International Patent Publication WO 2020/060401 A2 on Mar. 26, 2020, which claims the benefit under Article 8 of the Patent Cooperation Treaty to European Patent Application Serial No. 18194912.4, filed Sep. 18, 2019.

TECHNICAL FIELD

The disclosure concerns peptides and the useful application of such peptides to inhibit bacterial, fungal, viral and parasitic infections. The disclosed peptides are also useful for the treatment of inflammatory conditions or cancers.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

Bacterial infections are a major cause of disease and death worldwide. In addition, resistance against antibiotics among bacteria is nowadays a major threat to society. It is expected that—if no solutions are introduced—in 2050 there will be 10 million deaths yearly due to infections with antimicrobial resistant (AMR) microorganisms (de Kraker et al., 2016, O'Neill 2016). The top six most threatening bacteria include AMR *Enterococcus faecium, Staphylococcus aureus, Klebsiella pneumoniae, Acinetobacter baumannii, Pseudomonas aeruginosa*, and *Enterobacter* species, further referred to as the ESKAPE bacteria (Boucher et al., 2009). Infections by Gram-negative bacteria are currently considered as the major threat to human health, in particular due to emerging resistance and lack of classes of antibiotics.

Antibiotics are poorly effective in degrading bacterial biofilms. Elimination of bacteria within a biofilm requires 100-1000 times higher concentrations of antibiotics than planktonic bacteria (N. Hoiby et al., 2010; Olsen 2015). In a biofilm, the bacteria are surrounded by a matrix of extracellular polysaccharides, DNA and proteins. This matrix may protect the bacteria residing within biofilms from the actions of antibiotics by limiting the penetration into the matrix (Olsen 2015). The impaired activity of antibiotics on biofilm bacteria is also due to the presence of metabolically inactive bacteria within biofilms, referred to as persisters (Hoiby et al., 2010; Olsen 2015). Persisters are tolerant to antibiotics, which may lead to chronic, recurrent infections. Novel antibacterial agents are urgently needed, in particular as agents against antibiotic resistant as well as tolerant pathogens and to prevent and/or disrupt biofilms.

BRIEF SUMMARY

In one aspect, the disclosure provides an isolated or recombinant peptide having up to 200 amino acids and a) comprising at least 60% of an amino acid sequence selected from:

SP1
(SEQ ID NO: 1)
RKFKKSFKKIRKWVKKATKIAGEVAVEILITKVILGSVGL

SP2
(SEQ ID NO: 2)
KRVKRFKKFFKKVKKSVKKRLKKIFKKPMVIGVTIPF

SP3
(SEQ ID NO: 3)
KRFKKFFKKLKNSVKKRVKKFFRKPRVIGVTFPF

SP4
(SEQ ID NO: 4)
KRFKKFFKKLKNNVKKRVKKFFRKPRVIGVTIPF

SP5
(SEQ ID NO: 5)
KRFKKFFRKLKKSVKKRAKEFFKKPRVIGVSIPF

SP6
(SEQ ID NO: 6)
KRFKKFFKKVKKSVKKRLKKIFKKPMVIGVTIPF

SP7
(SEQ ID NO: 7)
KRFKKFFKKVKKSVKKRLKKIFKKPMVIGVSIPF

SP8
(SEQ ID NO: 8)
KRFRKFFKRLLKSVRRAVKKFRKKPRLIGLSTLL

SP9
(SEQ ID NO: 9)
KRFKKFFKKVKKSVKKRLKKIFKKPMVIGVTFPF

SP11
(SEQ ID NO: 10)
KRFKKFFRKLKKSVKKRVKKFFKKPRVIGVTIPF

SP12
(SEQ ID NO: 11)
KRFKKFFMKLKKSVKKRVMKFFKKPMVIGVTFPF

SP14
(SEQ ID NO: 12)
KRFKKFFKKAKKSVKKRLKKFFNKTRVIGVSIPF

SP15
(SEQ ID NO: 13)
KRFKKFFRKIKKGFRKIFKKTKIFIGGTIPI

SP16
(SEQ ID NO: 14)
KRFQNFFRELEKKFREFFRVYRITIGATIRF

SP17
(SEQ ID NO: 15)
KRFKDFFHRIRDGVRDFFRNNHFVCGVNFRF

SP18
(SEQ ID NO: 16)
KRFKKFFKKIKTGIKKVIKKTKQAIASHFRW

SP19
(SEQ ID NO: 17)
KRFLRVFKKLKRGIRKLFKKKKIVTGPLTS

SP20
(SEQ ID NO: 18)
AREKSFLQKMKVILQLSSQDQIQAF

SP21
(SEQ ID NO: 19)
KRFAGFFQFVIGVSFHF

-continued

SP22
(SEQ ID NO: 20)
DQVERGNFAKDGSKARVKKSLTKWVKFLKKIIAKLGRPLIGF

SP23
(SEQ ID NO: 21)
KRFKKFFKKIKNSVKKRVKKFFKKPRVIGVSIPF

SP24
(SEQ ID NO: 22)
KRFKKFFKKLKNSVRKCAKKFFKKLRVIRVSIPF

SP25
(SEQ ID NO: 23)
KRFKKFFKKVKKSVKKRLKKIFKKPIVIGVSIPF

SP26
(SEQ ID NO: 24)
KRFTFYKKVKKNVENLLNKFFKKLRVIGDSIPF

SP27
(SEQ ID NO: 25)
KRFKKFFRKVKKGVHRYFKKNKFYIAATIPYYG

SP28
(SEQ ID NO: 26)
KRFLRLVVFKKLKKGLRKLFKKKKIVTGHVTS

SP29
(SEQ ID NO: 27)
KRFKNFFKKIRDGIHEFIHNNRFVIGVNFRF

SP30
(SEQ ID NO: 28)
KRFKKFFKKIKNGIKTFIKKTQMAIGSHFRW

SP31
(SEQ ID NO: 29)
KRFKNFFKRVRDGIRDFFRKNHIVIGVNFRF

SP32
(SEQ ID NO: 30)
KRFLRVFRKLKKGLKKLFKRKKVVTGYVTA

SP33
(SEQ ID NO: 31)
KRFAGFFQFVVGVSFRF

SP34
(SEQ ID NO: 32)
KRFVGSFQLVVGVSFRF
and

SP35
(SEQ ID NO: 33)
KRFKKFLKKLKKSVKKHVKEFFKKPRVIGV;

preferably wherein the sequence is selected from (SEQ ID NO: 25)
KRFKKFFRKVKKGVHRYFKKNKFYIAATIPYYG (SP27), (SEQ ID NO: 10)
KRFKKFFRKLKKSVKKRVKKFFKKPRVIGVTIPF (SP11),
and (SEQ ID NO: 21)
KRFKKFFKKIKNSVKKRVKKFFKKPRVIGVSIPF (SP23);

b) comprising at least 60% of consecutive amino acids of a retro-inverso sequence of the sequences; or
c) a functional variant of a) or b), wherein the variant has one or more substitutions of an amino acid by a corresponding non-natural amino acid, has one or more substitutions of an amino acid by a corresponding D-amino acid, and/or has up to 5 amino acid substitutions, preferably wherein the amino acid substitutions are conservative amino acid substitutions.

In preferred embodiments, the amino acid sequence comprises at least 80% of the sequences.

In one aspect, the disclosure provides an isolated or recombinant peptide having between 20-200 amino acids, the peptide comprising:
a) at least 20 consecutive amino acids of an amino acid sequence selected from:

(SEQ ID NO: 25)
KRFKKFFRKVKKGVHRYFKKNKFYIAATIPYYG (SP27), (SEQ ID NO: 10)
KRFKKFFRKLKKSVKKRVKKFFKKPRVIGVTIPF (SP11),
and (SEQ ID NO: 21)
KRFKKFFKKIKNSVKKRVKKFFKKPRVIGVSIPF (SP23);

b) at least 20 consecutive amino acids of a retro-inverso sequence of a); or
c) a functional variant of a) or b), wherein the variant:
has one or more substitutions of an amino acid by a corresponding non-natural amino acid;
has one or more substitutions of an amino acid by a corresponding D-amino acid; and/or
has up to 5 amino acid substitutions, preferably wherein the amino acid substitutions are conservative amino acid substitutions.

Preferably the polypeptide further comprises:
a) at least an amino acid sequence VKKGVHRYFKKNKFY (SEQ ID NO:34),
b) the retro-inverso sequence of a); or
c) a functional variant of a) or b), wherein the variant has up to 2 substitutions selected from:
substitutions of an amino acid by a corresponding non-natural amino acid;
substitutions of an amino acid by a corresponding D-amino acid; and/or
amino acid substitutions, preferably wherein the amino acid substitutions are conservative amino acid substitutions.

In one aspect, the disclosure provides an isolated or recombinant peptide having between 20-200 amino acids, a nucleic acid molecule encoding the peptide, or a composition comprising the peptide or the nucleic acid for use in therapy as an anti-bacterial, antiviral, antifungal, anti-parasitic, anti-inflammatory, immune-modulating, and/or anti-cancer agent, the peptide comprises:
a) at least 20 consecutive amino acids of the amino acid sequence (SEQ ID NO: 4)
KRFKKFFKKLKNNVKKRVKKFFRKPRVIGVTIPF (SP4);

b) at least 20 consecutive amino acids of a retro-inverso sequence of a); or
c) a functional variant of a) or b), wherein the variant:
has one or more substitutions of an amino acid by a corresponding non-natural amino acid;
has one or more substitutions of an amino acid by a corresponding D-amino acid; and/or
has up to 5 amino acid substitutions, preferably wherein the amino acid substitutions are conservative amino acid substitutions.

In one aspect, the disclosure provides a nucleic acid molecule comprising a nucleic acid sequence encoding a peptide as disclosed herein. In one aspect, the disclosure provides a vector comprising the nucleic acid molecule as disclosed herein. Preferably the vector is an expression vector.

In one aspect, the disclosure provides a recombinant host cell comprising the nucleic acid molecule and/or the vector as disclosed herein. Preferably, the host cell is a mammalian, human, plant, bacterial and/or yeast cell.

In one aspect, the disclosure provides a composition comprising the peptide, the nucleic acid molecule and/or the vector as disclosed herein, wherein the composition is selected from a pharmaceutical composition comprising at least one pharmaceutically acceptable carrier, diluent and/or excipient; a cosmetic product; a food product; an oral care product; a cleaning product or an ophthalmic product. In some embodiments, the peptide, the nucleic acid molecule, the vector and/or the composition as disclosed herein are provided as a medicament.

In one aspect, the disclosure provides an article coated with the isolated or recombinant peptide as disclosed herein. Preferably wherein the article is a medical device and/or surgical instrument.

In some embodiments, the peptide, the nucleic acid molecule, the vector and/or the composition as disclosed herein is for use in therapy. Preferably, the therapy is for the treatment of a bacterial, fungal, viral and/or parasitic infection, an inflammatory condition, or a carcinoma. Preferably, the therapy is for the treatment of a condition resulting from bacterial, fungal, viral and/or parasitic infection, biofilm formation, an inflammatory condition, and/or a carcinoma. Preferably the peptide as disclosed herein has bioactivity against Gram-negative bacteria.

In one aspect, the disclosure provides the use of the isolated or recombinant peptide as disclosed herein to inhibit biofilm formation or to degrade biofilms; as an anti-bacterial agent, anti-fungal agent, antiviral agent, anti-parasitic agent, as a diagnostic, crop protectant, disinfectant, preservative anti-inflammatory agent, immune-modulating agent and/or anti-cancer agent, preferably wherein the use does not comprise the treatment of a human or animal body.

In some embodiments, the isolated or recombinant peptide, the nucleic acid molecule, or the composition for use in therapy as an anti-bacterial agent as disclosed herein, wherein the bacteria are antibiotic resistant bacteria, antibiotic tolerant bacteria, persistent bacteria, antibiotic persistent bacteria and/or a biofilm, preferably wherein the bacteria is antibiotic tolerant bacteria or part of a biofilm.

In some embodiments, the peptide or peptide for use as disclosed herein, is N-terminally and/or C-terminally modified, or the peptide is in a cyclic confirmation.

In preferred embodiments, the peptide is N-terminally and/or C-terminally modified with a Polyethylene glycol (PEG) group, polysaccharide and/or lipid.

In some embodiments, the peptide or a functional variant as disclosed herein comprises up to 200 amino acids, preferably between 25-200 amino acids. In some embodiments, the peptide or a functional variant comprises 25-100 amino acids, preferably 30-50 amino acids.

In some embodiments, the peptide or a functional variant as disclosed herein comprises up to 200 amino acids, preferably between 15-200 amino acids. In some embodiments, the peptide or a functional variant comprises 15-100 amino acids, preferably 15-50 amino acids, preferably 15-40 amino acids.

In some embodiments, the peptide or a functional variant as disclosed herein comprises up to 200 amino acids, preferably between 20-200 amino acids. In some embodiments, the peptide or a functional variant comprises 20-100 amino acids, preferably 20-50 amino acids, preferably 20-40 amino acids.

In some embodiments, the peptide or a functional variant as disclosed herein comprises up to 200 amino acids, preferably between 23-200 amino acids. In some embodiments, the peptide or a functional variant comprises 23-100 amino acids, preferably 23-50 amino acids, preferably 23-40 amino acids.

In some embodiments, the peptide or a functional variant as disclosed herein comprises up to 200 amino acids, preferably between 24-200 amino acids. In some embodiments, the peptide or a functional variant comprises 24-100 amino acids, preferably 24-50 amino acids, preferably 24-40 amino acids.

In one aspect, the disclosure provides a method of treating a subject in need thereof comprising administering to the subject a therapeutically effective amount of the peptide, the nucleic acid molecule, the vector and/or the composition as disclosed herein.

In one aspect, the disclosure provides a method of treating or preventing a bacterial, fungal, viral and/or parasitic infection in a subject in need thereof comprising administering to the subject a therapeutically effective amount of the peptide, the nucleic acid molecule, the vector and/or the composition as disclosed herein. In some embodiments, the subject has been diagnosed with a bacterial, fungal, viral and/or parasitic infection.

In one aspect, the disclosure provides a method of inhibiting biofilm formation or degrading a biofilm in a subject in need thereof comprising administering to the subject the peptide, the nucleic acid molecule, the vector and/or the composition as disclosed herein. In some embodiments, the subject has been implanted with a medical device.

In one aspect, the disclosure provides a method of treating an inflammatory disorder, preferably an auto-immune disease, or modulating an immune response in a subject in need thereof comprising administering to the subject a therapeutically effective amount of the peptide, the nucleic acid molecule, the vector and/or the composition as disclosed herein.

In one aspect, the disclosure provides a method of treating a cancer in a subject in need thereof comprising administering to the subject a therapeutically effective amount of the peptide, the nucleic acid molecule, the vector and/or the composition as disclosed herein.

In one aspect, the disclosure provides a method of inhibiting biofilm formation on a surface or degrading biofilm from a surface, the method comprising contacting the surface with the isolated or recombinant peptide and/or the composition as disclosed herein.

In one aspect, the disclosure provides, a method of eliminating, inhibiting, or reducing bacteria, viruses, fungi, and/or parasites, comprising providing the isolated or recombinant peptide and/or the composition as disclosed herein.

In one aspect, the disclosure provides a method of disinfecting a surface, or composition, the method comprising contacting the surface and/or composition or providing the surface or composition with the isolated or recombinant peptide and/or the composition as disclosed herein.

In one aspect, the disclosure provides a method of preparing a composition, the method comprising providing the surface or composition with the isolated or recombinant peptide and/or the composition as disclosed herein. In some embodiments, the isolated or recombinant peptide acts as a preservative.

In one aspect, the disclosure provides a method of protecting a plant from infection, the method comprising providing the isolated or recombinant peptide as disclosed herein to the plant, preferably crop plant.

In one aspect, the disclosure provides a method of modulating an immune response, preferably inhibiting or redirecting an immune response; reducing cancers; or inhibiting bacteria, viruses, fungi, and/or parasites in a system comprising providing the isolated or recombinant peptide, the nucleic acid molecule, the vector and/or the composition as disclosed herein to the system. In some embodiments, the system comprises in vitro cells or a cell culture.

In one aspect, the disclosure provides a method of inhibiting biofilm formation to a surface or degrading biofilm from a surface, the method comprising contacting the surface with an isolated or recombinant peptide and/or a composition as disclosed herein.

In one aspect, the disclosure provides a method of treating a bacterial infection in a subject in need thereof as disclosed herein, wherein the bacteria are antibiotic resistant bacteria, antibiotic tolerant bacteria and/or bacteria residing within a biofilm, including persisters.

The disclosure further provides methods for treating an individual in need thereof, comprising implanting a medical device at least partially coated with a peptide as disclosed herein into an individual in need thereof.

In one aspect, the disclosure provides an isolated or recombinant peptide having up to 200 amino acids for use in therapy, the peptide:

a) comprising at least 60% of an amino acid sequence selected from:

```
SP1
                                        (SEQ ID NO: 1)
RKFKKSFKKIRKWVKKATKIAGEVAVEILITKVILGSVGL

SP2
                                        (SEQ ID NO: 2)
KRVKRFKKFFKKVKKSVKKRLKKIFKKPMVIGVTIPF

SP3
                                        (SEQ ID NO: 3)
KRFKKFFKKLKNSVKKRVKKFFRKPRVIGVTFPF

SP4
                                        (SEQ ID NO: 4)
KRFKKFFKKLKNNVKKRVKKFFRKPRVIGVTIPF

SP5
                                        (SEQ ID NO: 5)
KRFKKFFRKLKKSVKKRAKEFFKKPRVIGVSIPF

SP6
                                        (SEQ ID NO: 6)
KRFKKFFKKVKKSVKKRLKKIFKKPMVIGVTIPF

SP7
                                        (SEQ ID NO: 7)
KRFKKFFKKVKKSVKKRLKKIFKKPMVIGVSIPF

SP8
                                        (SEQ ID NO: 8)
KRFRKFFKRLLKSVRRAVKKFRKKPRLIGLSTLL

SP9
                                        (SEQ ID NO: 9)
KRFKKFFKKVKKSVKKRLKKIFKKPMVIGVTFPF

SP11
                                       (SEQ ID NO: 10)
KRFKKFFRKLKKSVKKRVKKFFKKPRVIGVTIPF

SP12
                                       (SEQ ID NO: 11)
KRFKKFFMKLKKSVKKRVMKFFKKPMVIGVTFPF

SP14
                                       (SEQ ID NO: 12)
KRFKKFFKKAKKSVKKRLKKFFNKTRVIGVSIPF

SP15
                                       (SEQ ID NO: 13)
KRFKKFFRKIKKGFRKIFKKTKIFIGGTIPI

SP16
                                       (SEQ ID NO: 14)
KRFQNFFRELEKKFREFFRVYRITIGATIRF

SP17
                                       (SEQ ID NO: 15)
KRFKDFFHRIRDGVRDFFRNNHFVCGVNFRF

SP18
                                       (SEQ ID NO: 16)
KRFKKFFKKIKTGIKKVIKKTKQAIASHFRW

SP19
                                       (SEQ ID NO: 17)
KRFLRVFKKLKRGIRKLFKKKKIVTGPLTS

SP20
                                       (SEQ ID NO: 18)
AREKSFLQKMKVILQLSSQDQIQAF

SP21
                                       (SEQ ID NO: 19)
KRFAGFFQFVIGVSFHF

SP22
                                       (SEQ ID NO: 20)
DQVERGNFAKDGSKARVKKSLTKWVKFLKKIIAKLGRPLIGF

SP23
                                       (SEQ ID NO: 21)
KRFKKFFKKIKNSVKKRVKKFFKKPRVIGVSIPF

SP24
                                       (SEQ ID NO: 22)
KRFKKFFKKLKNSVRKCAKKFFKKLRVIRVSIPF

SP25
                                       (SEQ ID NO: 23)
KRFKKFFKKVKKSVKKRLKKIFKKPIVIGVSIPF

SP26
                                       (SEQ ID NO: 24)
KRFTFYKKVKKNVENLLNKFFKKLRVIGDSIPF

SP27
                                       (SEQ ID NO: 25)
KRFKKFFRKVKKGVHRYFKKNKFYIAATIPYYG

SP28
                                       (SEQ ID NO: 26)
KRFLRLVVFKKLKKGLRKLFKKKKIVTGHVTS

SP29
                                       (SEQ ID NO: 27)
KRFKNFFKKIRDGIHEFIHNNRFVIGVNFRF

SP30
                                       (SEQ ID NO: 28)
KRFKKFFKKIKNGIKTFIKKTQMAIGSHFRW

SP31
                                       (SEQ ID NO: 29)
KRFKNFFKRVRDGIRDFFRKNHIVIGVNFRF

SP32
                                       (SEQ ID NO: 30)
KRFLRVFRKLKKGLKKLFKRKKVVTGYVTA
```

```
SP33
                                  (SEQ ID NO: 31)
KRFAGFFQFVVGVSFRF

SP34
                                  (SEQ ID NO: 32)
KRFVGSFQLVVGVSFRF
and

SP35
                                  (SEQ ID NO: 33)
KRFKKFLKKLKKSVKKHVKEFFKKPRVIGV;
``` b) comprising at least 60% of consecutive amino acids of a retro-inverso sequence of a); or c) a functional variant of a) or b), wherein the variant:
- has one or more substitutions of an amino acid by a corresponding non-natural amino acid;
- has one or more substitutions of an amino acid by a corresponding D-amino acid; and/or
- has up to 5 amino acid substitutions, preferably wherein the amino acid substitutions are conservative amino acid substitutions, preferably wherein the use in therapy is as an anti-bacterial, antiviral, anti-fungal, anti-parasitic, anti-biofilm, anti-inflammatory, immune modulating, and/or anticancer agent.

In one aspect the disclosure provides the use of an isolated or recombinant peptide having between 20-200 amino acids to inhibit biofilm formation or to degrade biofilms; as an anti-bacterial agent, anti-fungal agent, antiviral agent, anti-parasitic agent, as a diagnostic, crop protectant, disinfectant, preservative, anti-inflammatory agent, immune-modulating agent and/or anticancer agent, wherein the peptide comprises:

a) comprising at least 60% of an amino acid sequence selected from:

```
SP1
                                   (SEQ ID NO: 1)
RKFKKSFKKIRKWVKKATKIAGEVAVEILITKVILGSVGL

SP2
                                   (SEQ ID NO: 2)
KRVKRFKKFFKKVKKSVKKRLKKIFKKPMVIGVTIPF

SP3
                                   (SEQ ID NO: 3)
KRFKKFFKKLKNSVKKRVKKFFRKPRVIGVTFPF

SP4
                                   (SEQ ID NO: 4)
KRFKKFFKKLKNNVKKRVKKFFRKPRVIGVTIPF

SP5
                                   (SEQ ID NO: 5)
KRFKKFFRKLKKSVKKRAKEFFKKPRVIGVSIPF

SP6
                                   (SEQ ID NO: 6)
KRFKKFFKKVKKSVKKRLKKIFKKPMVIGVTIPF

SP7
                                   (SEQ ID NO: 7)
KRFKKFFKKVKKSVKKRLKKIFKKPMVIGVSIPF

SP8
                                   (SEQ ID NO: 8)
KRFRKFFKRLLKSVRRAVKKFRKKPRLIGLSTLL

SP9
                                   (SEQ ID NO: 9)
KRFKKFFKKVKKSVKKRLKKIFKKPMVIGVTFPF

SP11
                                  (SEQ ID NO: 10)
KRFKKFFRKLKKSVKKRVKKFFKKPRVIGVTIPF

SP12
                                  (SEQ ID NO: 11)
KRFKKFFMKLKKSVKKRVMKFFKKPMVIGVTFPF

SP14
                                  (SEQ ID NO: 12)
KRFKKFFKKAKKSVKKRLKKFFNKTRVIGVSIPF

SP15
                                  (SEQ ID NO: 13)
KRFKKFFRKIKKGFRKIFKKTKIFIGGTIPI

SP16
                                  (SEQ ID NO: 14)
KRFQNFFRELEKKFREFFRVYRITIGATIRF

SP17
                                  (SEQ ID NO: 15)
KRFKDFFHRIRDGVRDFFRNNHFVCGVNFRF

SP18
                                  (SEQ ID NO: 16)
KRFKKFFKKIKTGIKKVIKKTKQAIASHFRW

SP19
                                  (SEQ ID NO: 17)
KRFLRVFKKLKRGIRKLFKKKKIVTGPLTS

SP20
                                  (SEQ ID NO: 18)
AREKSFLQKMKVILQLSSQDQIQAF

SP21
                                  (SEQ ID NO: 19)
KRFAGFFQFVIGVSFHF

SP22
                                  (SEQ ID NO: 20)
DQVERGNFAKDGSKARVKKSLTKWVKFLKKIIAKLGRPLIGF

SP23
                                  (SEQ ID NO: 21)
KRFKKFFKKIKNSVKKRVKKFFKKPRVIGVSIPF

SP24
                                  (SEQ ID NO: 22)
KRFKKFFKKLKNSVRKCAKKFFKKLRVIRVSIPF

SP25
                                  (SEQ ID NO: 23)
KRFKKFFKKVKKSVKKRLKKIFKKPIVIGVSIPF

SP26
                                  (SEQ ID NO: 24)
KRFTFYKKVKKNVENLLNKFFKKLRVIGDSIPF

SP27
                                  (SEQ ID NO: 25)
KRFKKFFRKVKKGVHRYFKKNKFYIAATIPYYG

SP28
                                  (SEQ ID NO: 26)
KRFLRLVVFKKLKKGLRKLFKKKKIVTGHVTS

SP29
                                  (SEQ ID NO: 27)
KRFKNFFKKIRDGIHEFIHNNRFVIGVNFRF

SP30
                                  (SEQ ID NO: 28)
KRFKKFFKKIKNGIKTFIKKTQMAIGSHFRW

SP31
                                  (SEQ ID NO: 29)
KRFKNFFKRVRDGIRDFFRKNHIVIGVNFRF
```

-continued

SP32
KRFLRVFRKLKKGLKKLFKRKKVVTGYVTA
(SEQ ID NO: 30)

SP33
KRFAGFFQFVVGVSFRF
(SEQ ID NO: 31)

SP34
KRFVGSFQLVVGVSFRF
(SEQ ID NO: 32)
and

SP35
KRFKKFLKKLKKSVKKHVKEFFKKPRVIGV;
(SEQ ID NO: 33)

b) comprising at least 60% of consecutive amino acids of a retro-inverso sequence of a); or
c) a functional variant of a) or b) wherein the variant:
has one or more substitutions of an amino acid by a corresponding non-natural amino acid;
has one or more substitutions of an amino acid by a corresponding D-amino acid; and/or
has up to 5 amino acid substitutions, preferably wherein the amino acid substitutions are conservative amino acid substitutions; wherein the use does not comprise the treatment of a human or animal body.

BRIEF DESCRIPTION OF THE DRAWINGS

FIG. 3: Bactericidal activity of SP4 and SP27 on MDR ESKAPE strains and colistin-resistant *E. coli*. Bacteria were exposed to increasing concentrations of the snake peptides in 50% v/v human plasma (in the case of *E. coli* also in 50% pooled urine). After 2 hours, the surviving bacteria were plated on blood agar for microbiological assessment of the number of viable bacteria compared to the negative control, i.e., no peptide. The antibiotic resistance profiles of the various bacteria are indicated. If the bacteria are sensitive for the antibiotic class a green box is shown, the red box means that the bacteria is intermediate or resistant for at least one of the antibiotics in the class. A gray box means the susceptibility for that class has not been accessed. The bactericidal activity is expressed as the $LC_{99.9}$, i.e., the lowest dose of the peptide resulting in killing of 99.95 of the bacteria within 2 hours.

DETAILED DESCRIPTION

In the search for novel antibacterial agents, antimicrobial peptides are considered to be promising candidates. These peptides are an essential component of the defensive system of organisms throughout nature and offer protection against invading pathogens. The peptides are known to act on the cell membrane allowing them to kill micro-organisms like bacteria and fungi rapidly. Therefore, the peptides are effective against bacteria regardless of the susceptibility to current antibiotics and the metabolic activity of the bacteria. This is in contrast to conventional antibiotics in which effectiveness generally depends on metabolic active, multiplying bacteria. In addition, certain anti-microbial peptides are shown to regulate the adaptive and the innate immune system, inflammation and wound healing. Furthermore, certain peptides are shown to have anti-fungal, anti-viral, anti-parasitic and anti-cancer activities.

The sequence and secondary structure of antimicrobial peptides reported in the literature is diverse. However, most peptides are around 15-40 amino acids, cationic and amphipathic. Their interaction with the anionic membrane surfaces of the target microbes leads to permeabilization of the membrane. As a result the membrane integrity is lost, which leads to lysis and death of the bacterial/fungal cells. Various molecular mechanisms are postulated for membrane permeabilization by antimicrobial peptides.

Antimicrobial peptides are part of the innate immune system and combine a broad activity against microorganisms with immunomodulatory capabilities (Bahar et al., 2013; De Latour et al., 2010). Antimicrobial peptides have a positive charge that makes it possible to bind to the negatively charged membrane of bacteria and disrupt the lipid bilayer (Dean et al., 2011). An important family of antimicrobial peptides are the cathelicidins. In humans, only one cathelicidin has been identified (LL-37) that has anti-bacterial and immunomodulatory effects (Kosciuczuk et al., 2012; Scott et al., 2002). From the novel cathelicidin sequences found in the genomes of seventeen snake species, a total of 35 different snake peptides were synthesized.

Figure 1:
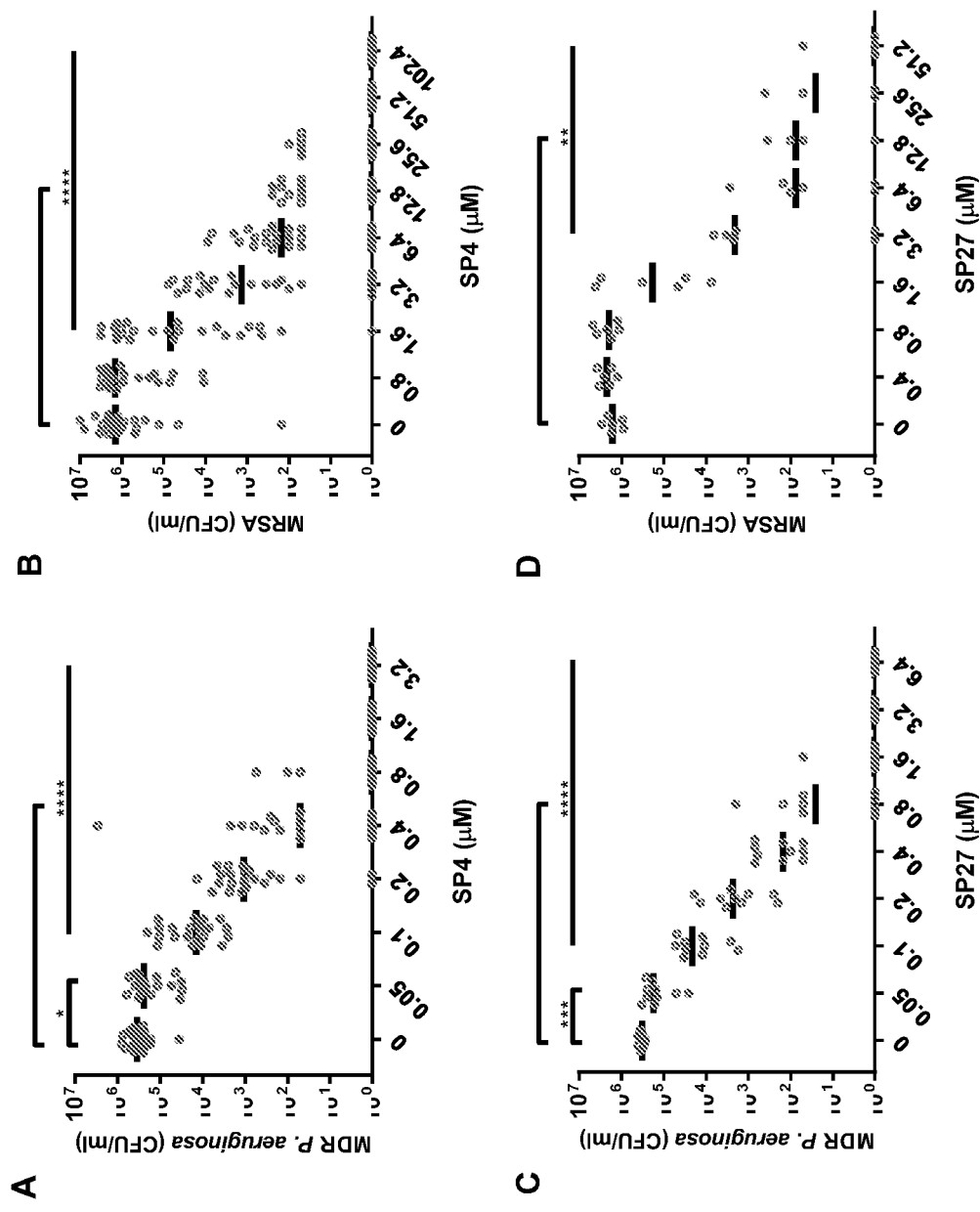
FIG. 1: Dose-dependent killing of multidrug resistant (MDR) *P. aeruginosa* and *S. aureus* by SP4 and SP27. Bactericidal effect of SP4 on MDR *P. aeruginosa* LUH 15103 (Panel A) and MDR *S. aureus* LUH 14616 (Panel B). Bactericidal effect of SP27 on AMR *P. aeruginosa* (Panel C) and MDR *S. aureus* (Panel D). Killing was assessed as the reduction in viable bacteria (CFU/ml) after a 2-hour exposure to increasing peptide concentrations in the presence of 50% v/v human plasma. Significance compared to control (0 μM) was calculated with the Mann-Whitney U test (*P<0.05, P<0.01, *P<0.001 and ****P<0.0001).
Figure 2:
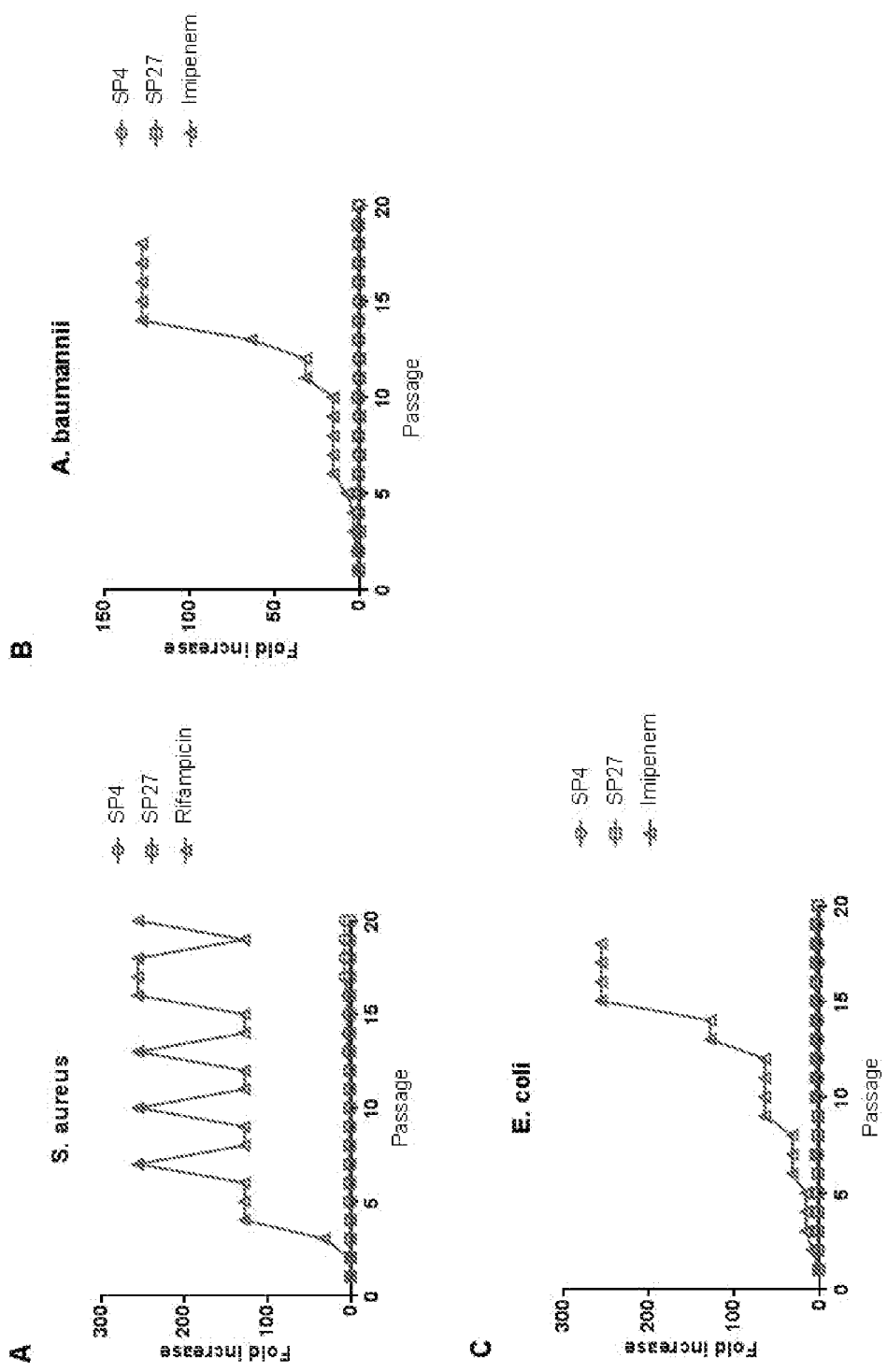
FIG. 2: Resistance development of *S. aureus* (Panel A) and *A. baumannii* (Panel B) against SP4, SP27 and rifampicin. The development of resistance of *S. aureus* LUH 14616 and *A. Baumannii* to SP4 (○), SP27 (□) and rifampicin (Δ) was assessed using 20 passages. The values are the fold increase of the MIC at each passage compared to the MIC at the first passage. (Panel C) Resistance development of *E. coli* against SP4, SP27 and imipenem. The development of resistance of *E. coli* to SP4 (○), SP27 (□) and imipenem (Δ) was assessed using 20 passages. The values are the fold increase of the MIC at each passage compared to the MIC at the first passage.

Provided are novel peptides that exerts high activity against pathogenic microorganisms, but low toxicity in humans. As depicted in FIG. 1, the LC99.9 (i.e., the lowest concentration of peptide that kills ≥99.9% of the bacteria) for many of the novel peptides is at least 2-3 orders of magnitude lower than the concentration of peptide that begins to demonstrate hemolytic effects. Also provided are peptides that are effective against both gram-negative and gram-positive bacteria. While not wishing to be bound by theory, the peptides disclosed herein also offer the advantage that bacterial resistance to the peptides develops significantly slower than resistance to antibiotics.

Figure 9A:
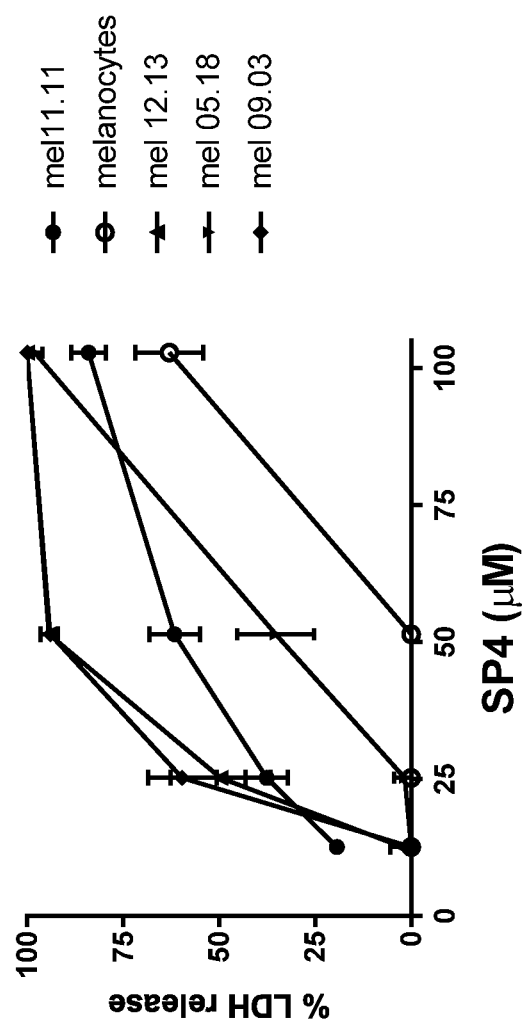
FIGS. 9A and 9B: Selective tumoricidal activity of SP4 and SP27. Briefly, primary human melanocytes and 4 melanoma cell lines were exposed to increasing doses of SP4 (FIG. 9A) and SP27 (FIG. 9B) for 4 hours and then the cell viability was assessed by measuring the LDH release by the cells. Results are expressed as the percentage of LDH release by peptide-exposed cells as compared to triton-exposed cells (=100% LDH release).
Figure 9B:
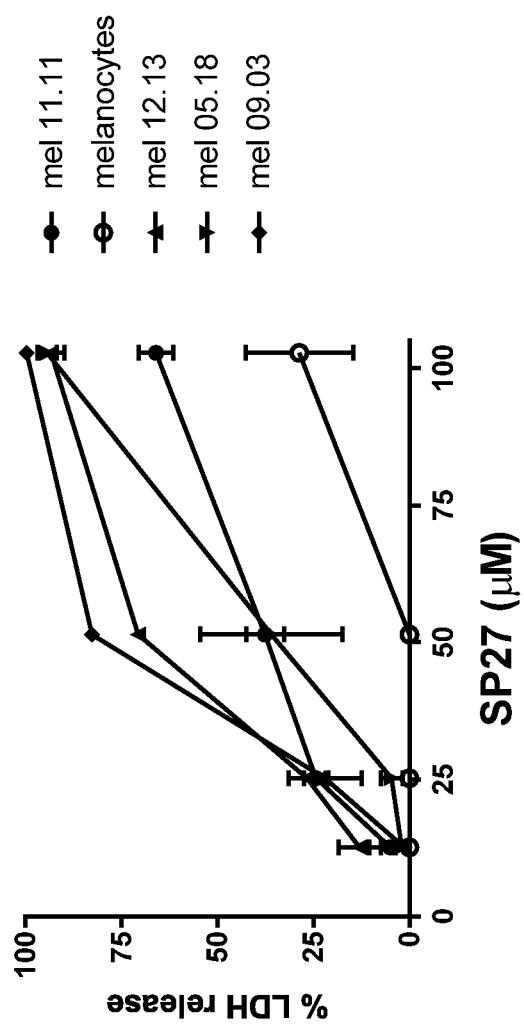

Further provided are novel peptides that selectively kill cancer cells. As depicted in FIGS. 9A and 9B, the novel peptides exert effects on cancer cells at concentrations that have no effect on non-cancerous cells.

In one aspect, the present disclosure provides isolated or recombinant peptides having up to 200 amino acids and comprising an amino acid sequence selected from:

```
SP1
                                        (SEQ ID NO: 1)
RKFKKSFKKIRKWVKKATKIAGEVAVEILITKVILGSVGL

SP2
                                        (SEQ ID NO: 2)
KRVKRFKKFFKKVKKSVKKRLKKIFKKPMVIGVTIPF

SP3
                                        (SEQ ID NO: 3)
KRFKKFFKKLKNSVKKRVKKFFRKPRVIGVTFPF

SP4
                                        (SEQ ID NO: 4)
KRFKKFFKKLKNNVKKRVKKFFRKPRVIGVTIPF

SP5
                                        (SEQ ID NO: 5)
KRFKKFFRKLKKSVKKRAKEFFKKPRVIGVSIPF

SP6
                                        (SEQ ID NO: 6)
KRFKKFFKKVKKSVKKRLKKIFKKPMVIGVTIPF

SP7
                                        (SEQ ID NO: 7)
KRFKKFFKKVKKSVKKRLKKIFKKPMVIGVSIPF

SP8
                                        (SEQ ID NO: 8)
KRFRKFFKRLLKSVRRAVKKFRKKPRLIGLSTLL

SP9
                                        (SEQ ID NO: 9)
KRFKKFFKKVKKSVKKRLKKIFKKPMVIGVTFPF

SP11
                                       (SEQ ID NO: 10)
KRFKKFFRKLKKSVKKRVKKFFKKPRVIGVTIPF

SP12
                                       (SEQ ID NO: 11)
KRFKKFFMKLKKSVKKRVMKFFKKPMVIGVTFPF

SP14
                                       (SEQ ID NO: 12)
KRFKKFFKKAKKSVKKRLKKFFNKTRVIGVSIPF

SP15
                                       (SEQ ID NO: 13)
KRFKKFFRKIKKGFRKIFKKTKIFIGGTIPI

SP16
                                       (SEQ ID NO: 14)
KRFQNFFRELEKKFREFFRVYRITIGATIRF

SP17
                                       (SEQ ID NO: 15)
KRFKDFFHRIRDGVRDFFRNNHFVCGVNFRF

SP18
                                       (SEQ ID NO: 16)
KRFKKFFKKIKTGIKKVIKKTKQAIASHFRW

SP19
                                       (SEQ ID NO: 17)
KRFLRVFKKLKRGIRKLFKKKKIVTGPLTS

SP20
                                       (SEQ ID NO: 18)
AREKSFLQKMKVILQLSSQDQIQAF

SP21
                                       (SEQ ID NO: 19)
KRFAGFFQFVIGVSFHF

SP22
                                       (SEQ ID NO: 20)
DQVERGNFAKDGSKARVKKSLTKWVKFLKKIIAKLGRPLIGF

SP23
                                       (SEQ ID NO: 21)
KRFKKFFKKIKNSVKKRVKKFFKKPRVIGVSIPF

SP24
                                       (SEQ ID NO: 22)
KRFKKFFKKLKNSVRKCAKKFFKKLRVIRVSIPF

SP25
                                       (SEQ ID NO: 23)
KRFKKFFKKVKKSVKKRLKKIFKKPIVIGVSIPF

SP26
                                       (SEQ ID NO: 24)
KRFTFYKKVKKNVENLLNKFFKKLRVIGDSIPF

SP27
                                       (SEQ ID NO: 25)
KRFKKFFRKVKKGVHRYFKKNKFYIAATIPYYG

SP28
                                       (SEQ ID NO: 26)
KRFLRLVVFKKLKKGLRKLFKKKKIVTGHVTS
```

```
SP29
                                       (SEQ ID NO: 27)
KRFKNFFKKIRDGIHEFIHNNRFVIGVNFRF

SP30
                                       (SEQ ID NO: 28)
KRFKKFFKKIKNGIKTFIKKTQMAIGSHFRW

SP31
                                       (SEQ ID NO: 29)
KRFKNFFKRVRDGIRDFFRKNHIVIGVNFRF

SP32
                                       (SEQ ID NO: 30)
KRFLRVFRKLKKGLKKLFKRKKVVTGYVTA

SP33
                                       (SEQ ID NO: 31)
KRFAGFFQFVVGVSFRF

SP34
                                       (SEQ ID NO: 32)
KRFVGSFQLVVGVSFRF
and SP35
                                       (SEQ ID NO: 33)
KRFKKFLKKLKKSVKKHVKEFFKKPRVIGV;
```

The disclosure further provides peptides having deletions at the N- and/or C-terminus. In a particular embodiment, the disclosure provides at least 15, preferably at least 20, or at least 25 consecutive amino acids of an amino acid sequence selected from:

```
                                       (SEQ ID NO: 25)
KRFKKFFRKVKKGVHRYFKKNKFYIAATIPYYG (SP27), (SEQ ID NO: 10)
KRFKKFFRKLKKSVKKRVKKFFKKPRVIGVTIPF (SP11), (SEQ ID NO: 21)
KRFKKFFKKIKNSVKKRVKKFFKKPRVIGVSIPF (SP23);
and

KRFKKFFKKLKNNVKKRVKKFFRKPRVIGVTIPF (SP4).
```

The disclosure further provides peptides having an amino acid sequence that comprises at least 80% of any of the above mentioned sequences. Preferably, such a peptide comprises 80% of a consecutive sequence provided herein. For example, the peptide may lack a limited number of amino acids at the N-terminus and/or C-terminus, as long as 80% of the sequence is present. For example, 80% of SP1 includes 32 of the consecutive amino acids of SP1 (RKFKKSFKKIRKWVKKATKIAGEVAVEIL-ITKVILGSVGL). This includes a deletion of up to 8 amino acids on the C-terminus or a deletion of up to 8 amino acids on the C-terminus, or a deletion at the N-terminus and deletion on the C-terminus of in total up to 8 amino acids.

The disclosure further provides peptides having an amino acid sequence that comprises at least 60% of any of the above mentioned sequences. Preferably, such a peptide comprises 60% of a consecutive sequence provided herein. For example, the peptide may lack a limited number of amino acids at the N-terminus and/or C-terminus, as long as 60% of the sequence is present. For example, 60% of SP4 includes 21 of the consecutive amino acids of SP4 (KRFKKFFKKLKNNVKKRVKKFFRKPRVIGVTIPF (SEQ ID NO:4)). This includes a deletion of up to 13 amino acids on the C-terminus or a deletion of up to 13 amino acids on the C-terminus, or a deletion at the N-terminus and deletion on the C-terminus of in total up to 13 amino acids.

For example, 60% of SP27 includes 20 of the consecutive amino acids of SP27 (KRFKKFFRKVKKGVHRYFK-KNKFYIAATIPYYG (SEQ ID NO:25)). This includes a deletion of up to 13 amino acids on the C-terminus or a deletion of up to 13 amino acids on the C-terminus, or a deletion at the N-terminus and deletion on the C-terminus of in total up to 13 amino acids.

Preferably, the peptide may have a deletion of up to 9 amino acids on the C-terminus or a deletion of up to 9 amino acids on the C-terminus, or a deletion at the N-terminus and deletion on the C-terminus of in total up to 13 amino acids, whereby the deletion at the N-terminus and deletion on the C-terminus are limited to maximum 9 amino acids.

The disclosure further provides peptides having a retro-inverso sequence of the peptides disclosed herein. These "retro-inverso peptides" may similarly have deletions as the N- or C-terminus as disclosed herein. As known to a skilled person, retro-inverso peptides are peptides in which the amino acid sequence is reversed and the alpha-center chirality of the amino acids is inverted. Typically, and in preferred embodiments, a retro-inverso peptide consists of D-amino acids. Retro-inverso peptides may have binding characteristics similar to their L-peptide counterparts.

The disclosure further provides functional variants of the peptides as described herein. The functional variant may have one or more substitutions of an amino acid by a corresponding non-natural amino acid, one or more substitutions of an amino acid by a corresponding D-amino acid, and/or up to 5 amino acid substitutions, preferably wherein the amino acid substitutions are conservative amino acid substitutions.

In one embodiment, one or more natural amino acids of the sequence are substituted by a corresponding non-natural amino acid. As used herein, a "corresponding non-natural amino acid" refers to a non-natural amino acid that is a derivative of the reference natural amino acid. For instance, a natural amino acid is substituted by the corresponding β-amino acid. β-amino acids have their amino group bonded to the β carbon rather than the α carbon as in the natural amino acids. For instance, α-alanine is substituted by β-alanine, etc. Other examples of substitution of a natural amino acid by a non-natural amino acid that is a derivative of the natural amino acid are the following. Alanine is, for instance, substituted by beta-alanine, t-butylalanine, 2-naphthylalanine; L-3-(2-naphthyl)alanine, or 2-aminoisobutyric acid. Arginine is, for instance, substituted by homoarginine, ornithine, N5-carbamoyl ornithine, 3-amino-propionic acid, methylarginine, asymmetric dimethylarginine, shortened arginine, or citrulline. Asparagine is, for instance, substituted by N-ethylasparagine. Aspartic acid is, for instance, substituted by 4-tert-butyl hydrogen 2-azidosuccinate. Cysteine is, for instance, substituted by cysteic acid or homocysteine. Glutamic acid is, for instance, substituted by γ-carboxy-DL-glutamic acid or 4-fluoro-DL-glutamic acid. Glutamine is, for instance, substituted by D-citrulline or thio-L-citrulline. Glycine is, for instance, substituted by N-methylglycine, t-butylglycine, N-methylglycine, or D-allylglycine. Histidine is, for instance, substituted by 3-(3-methyl-4-nitrobenzyl)-L-histidine methyl ester, 1-methylhistidine, or 3-methylhistidine. Isoleucine is, for instance, substituted by isodesmosine, N-methylisoleucine, allo-isoleucine, norvaline, homoleucine, norleucine, or 2-aminobutyric acid. Leucine is, for instance, substituted by norleucine, desmosine, or 5,5,5-trifluoro-leucine. Lysine is, for instance, substituted by 6-N-methyllysine, 2-aminoheptanoic acid, N-acetyl lysine, hydroxylysine, allo-hydroxylysine, homolysine, ε-methyl lysine, ε,ε-dimethyl lysine, ε,ε,ε-trimethyl lysine, ornithine, 2,3-diaminopropanoic acid, or 2,4-diaminobutanoic acid. Methionine is, for instance, substituted by methionine sulfoxide. Phenylalanine is, for instance, substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine, homophenylalanine, homotyrosine, phenylglycine, 4-fluorophenylalanine, 4-chlorophenylalanine, 4-cyanophenylalanine, 4-nitrophenylalanine, or cyclohexylalanine. Proline is, for instance, substituted by 3-hydroxyproline, 4-hydroxyproline, isonipecotic acid, or thiaproline. Serine is, for instance, substituted by homoserine, isoserine, or 3-phenylserine. Threonine is, for instance, substituted by D-thyroxine or allo-threonine. Tryptophan is, for instance, substituted by 5-hydroxy-tryptophan, 5-methoxy-tryptophan, or 5-fluoro-tryptophan. Tyrosine is, for instance, substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine. Valine is, for instance, substituted by norvaline, N-methylvaline, 3-fluoro-valine, homoleucine, norleucine, or 2-aminobutyric acid.

In preferred embodiments, one or more amino acids selected from Lysine (K), Arginine (R), Phenylalanine (F), Valine (V), Histidine (H), Tyrosine (Y), Isoleucine (I), or Proline (P) are substituted by a corresponding non-natural amino acid.

In one embodiment, a variant of an amino acid sequence as defined herein may contain one or more substitutions of an L-amino acid by its corresponding D-amino acid. "Corresponding D-amino acid" as used herein is defined as the D-amino acid counter part of an L-amino acid. For example, the corresponding D-amino acid of alanine (A) is D-alanine (a), the corresponding D-amino acid of arginine (R) is D-arginine (r), the corresponding D-amino acid of asparagine (N) is D-asparagine (n), etc. All L-amino acids of a variant as defined herein may be substituted by their corresponding D-amino acids. Hence, the variant may consist entirely of D-amino acids because activity is retained in polypeptides comprising such amino acid variant. Peptides that contain D-amino acids may have advantages over peptides that contain only L-amino acids. In general, D-amino acid containing peptides are less susceptible to proteolytic degradation and have a longer effective time when used as pharmaceuticals. Retro-inverso peptides or D-amino acids allow the design of peptide based drugs that are bioactive and possess increased bioavailability in addition to being resistant to proteolysis.

In some embodiments, functional variants of the peptides may also have up to 5 amino acid substitutions. Optionally, the functional variants of the peptides may have up to 4 amino acid substitutions. Optionally, the functional variants of the peptides may have up to 3 amino acid substitutions. Optionally, the functional variants of the peptides may have up to 2 amino acid substitutions. Optionally, the functional variants of the peptides may have 1 amino acid substitution.

In preferred embodiments, functional variants of the peptides may also have up to 5 conservative amino acid substitutions. Conservative substitutions are amino acid substitutions that change the given amino acid to a different amino acid with similar biochemical properties. For example, amino acids with a hydrophobic side chain are substituted with another amino acid having a hydrophobic side chain. Amino acids with electrically charged side chains are substituted with another amino acid having an electrically charged side chain, preferably an amino acid with a positively charged side chain is substituted by another amino acid with a positively charged side chain and an amino acid with a negatively charged side chain is substituted by another amino acid with a negatively charged side chain. Amino acids with a polar side chain are substituted with another amino acid having a polar side chain.

In preferred embodiments, functional variants of the peptides may have up to 4 conservative amino acid substitutions, preferably up to 3 conservative amino acid substitutions, preferably up to 2 conservative amino acid substitutions, preferably up to 1 conservative amino acid substitution.

Examples of conservative amino acid substitutions are substitution of one or more amino acids selected from the group of L, I, V or A by another amino acid selected from the group; substitution of one or more amino acids selected from the group of R, K or H by another amino acid selected from the group; substitution of E by Q; substitution of Y or W by F; substitution of one or more amino acids selected from the group of Q, N, A, S or T by another amino acid selected from the group.

The peptides or functional variants as disclosed herein comprise up to 200 amino acids. In some embodiments, the peptide or a functional variant comprises between 25-200 amino acids. In some embodiments, the peptide or a functional variant comprises 25-100 amino acids, preferably between 30-50 amino acids.

The peptides or functional variants as disclosed herein comprise up to 200 amino acids. In some embodiments, the peptide or a functional variant comprises between 15-200 amino acids. In some embodiments, the peptide or a functional variant comprises 15-100 amino acids, preferably between 15-50 amino acids, preferably 15-40 amino acids.

The peptides or functional variants as disclosed herein comprise up to 200 amino acids. In some embodiments, the peptide or a functional variant comprises between 20-200 amino acids. In some embodiments, the peptide or a functional variant comprises 20-100 amino acids, preferably between 20-50 amino acids, preferably 20-40 amino acids.

The peptides or functional variants as disclosed herein comprise up to 200 amino acids. In some embodiments, the peptide or a functional variant comprises between 23-200 amino acids. In some embodiments, the peptide or a functional variant comprises 23-100 amino acids, preferably between 23-50 amino acids, preferably 23-40 amino acids.

The peptides or functional variants as disclosed herein comprise up to 200 amino acids. In some embodiments, the peptide or a functional variant comprises between 24-200 amino acids. In some embodiments, the peptide or a functional variant comprises 24-100 amino acids, preferably between 24-50 amino acids, preferably 24-40 amino acids.

In some embodiments, the peptides as disclosed herein are N-terminally and/or C-terminally modified, or the peptide is in a cyclic confirmation. Such modifications may be useful to increase the stability of the peptides disclosed herein and/or reduce degradation by peptidases and proteases. The modifications may also permit coupling of the peptides to other groups, for example, to other amino acid sequences or other biomolecules. As used herein, "N-terminally and/or C-terminally modified" includes a modified amino group or carboxy group. Examples of N-terminal modifications include acetylated, formylated, or guanylated N-termini and examples of C-terminal modifications are amidated C-termini. Additional modifications include acetylation, amidation, formylation, or guanylation. The peptides disclosed herein may also be conjugated to a non-peptide moiety at the N- or C-terminus to form a peptide conjugate.

Suitable non-peptide moieties include, e.g., polymers (e.g., PEG), oligosaccharides, lipids, small molecule drugs, etc.

In some embodiments, the peptides as disclosed herein are N-terminally and/or C-terminally modified with a polymer chain, polysaccharide and/or lipid. In preferred embodiments, the peptides are N-terminally and/or C-terminally modified with Polyethylene glycol (PEG) and/or PEGylated. Examples of PEG polymer chains include PEG2, PEG3, PEG5, PEG11, and PEG27. Such modification may be useful to increase the stability of the peptides disclosed herein and/or reduce degradation by peptidases and proteases. The covalent attachment of PEG to a peptide may "mask" the agent from the host's immune system and potentially reducing immunogenicity. Modification with PEG may also increase its hydrodynamic size, which may prolong the circulatory time by reducing renal clearance. Modification with PEG may also provide water solubility to the peptides.

It is clear to a skilled person that the peptides disclosed herein also include the salts of such peptides, in particular, a "pharmaceutically acceptable salt" such as acid addition salts and base addition salts. As used herein, a "pharmaceutically acceptable salt" refers to a salt that retains the desired activity and is suitable for administration to humans or animals. Methods for the preparation of salts of peptides are known in the art and generally involve mixing of the peptide with a pharmaceutically acceptable acid or based, for instance, by reacting the free acid or free base forms of the product with one or more equivalents of the appropriate acid or base in a solvent or medium in which the salt is insoluble, or in a solvent such as water, which is then removed in vacuo or by freeze-drying, or by exchanging the cations of an existing salt for another cation on a suitable ion exchange resin. Examples of pharmaceutically acceptable acids and bases include organic and inorganic acids such as formic acid, acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid, phosphoric acid, and thiocyanic acid, which form ammonium salts with free amino groups of polypeptides, and bases, which form carboxylate salts with free carboxylic groups of polypeptides, such as ethylamine, methylamine, dimethylamine, triethylamine, isopropylamine, diisopropylamine, and other mono-, di- and trialkylamines, and arylamines.

A preferred isolated or recombinant peptide of the disclosure has between 15-200 amino acids comprising at least 15 consecutive amino acids of an amino acid sequence selected from: KRFKKFFRKVKKGVHRYFK-KNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNS-VKKRVKKFFKKPRVIGVSIPF (SP23) (SEQ ID NO:21). In some embodiments, the peptide comprises at least 15 consecutive amino acids of a retro-inverso sequence of the sequences or is a functional variant of the peptides.

A preferred isolated or recombinant peptide of the disclosure has between 20-200 amino acids comprising at least 20 consecutive amino acids of an amino acid sequence selected from: KRFKKFFRKVKKGVHRYFK-KNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNS-VKKRVKKFFKKPRVIGVSIPF (SP23) (SEQ ID NO:21). In some embodiments, the peptide comprises at least 20 consecutive amino acids of a retro-inverso sequence of the sequences or is a functional variant of the peptides.

A preferred isolated or recombinant peptide of the disclosure has between 24-200 amino acids comprising at least 24 consecutive amino acids of an amino acid sequence selected from: KRFKKFFRKVKKGVHRYFK-KNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNS-VKKRVKKFFKKPRVIGVSIPF (SP23) (SEQ ID NO:21). In some embodiments, the peptide comprises at least 24 consecutive amino acids of a retro-inverso sequence of the sequences or is a functional variant of the peptides.

A preferred isolated or recombinant peptide of the disclosure has between 25-200 amino acids comprising at least 25 consecutive amino acids of an amino acid sequence selected from: KRFKKFFRKVKKGVHRYFK-KNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNS-VKKRVKKFFKKPRVIGVSIPF (SP23) (SEQ ID NO:21). In some embodiments, the peptide comprises at least 25 consecutive amino acids of a retro-inverso sequence of the sequences or is a functional variant of the peptides.

A preferred isolated or recombinant peptide of the disclosure has between 15-200 amino acids comprising at least 15 consecutive amino acids of the amino acid sequence KRFKKFFKKLKNNVKKRVKKFFRKPRVIGVTIPF (SP4) (SEQ ID NO:4). In some embodiments, the peptide comprises at least 15 consecutive amino acids of a retro-inverso sequence of the sequence or is a functional variant of the peptides.

Preferably, the isolated or recombinant peptide of the disclosure has between 20-200 amino acids comprises at least 20 consecutive amino acids of the amino acid sequence KRFKKFFKKLKNNVKKRVKKFFRKPRVIGVTIPF (SP4) (SEQ ID NO:4). In some embodiments, the peptide comprises at least 20 consecutive amino acids of a retro-inverso sequence of the sequence or is a functional variant of the peptides.

Preferably, the isolated or recombinant peptide of the disclosure has between 24-200 amino acids comprises at least 24 consecutive amino acids of the amino acid sequence KRFKKFFKKLKNNVKKRVKKFFRKPRVIGVTIPF (SP4) (SEQ ID NO:4). In some embodiments, the peptide comprises at least 24 consecutive amino acids of a retro-inverso sequence of the sequence or is a functional variant of the peptides.

A preferred isolated or recombinant peptide of the disclosure has between 25-200 amino acids comprising at least 25 consecutive amino acids of the amino acid sequence KRFKKFFKKLKNNVKKRVKKFFRKPRVIGVTIPF (SP4) (SEQ ID NO:4). In some embodiments, the peptide comprises at least 25 consecutive amino acids of a retro-inverso sequence of the sequence or is a functional variant of the peptides.

A preferred isolated or recombinant peptide of the disclosure comprises:
 a) at least an amino acid sequence VKKGVHRYFK-KNKFY (SEQ ID NO:34),
 b) the retro-inverso sequence of a); or
 c) a functional variant of a) or b), wherein the variant has up to 5 substitutions, preferably up to 4 substitutions, preferably up to 3 substitutions, preferably up to 2 substitutions, preferably up to 1 substitution, selected from:

substitutions of an amino acid by a corresponding non-natural amino acid;

substitutions of an amino acid by a corresponding D-amino acid; and/or amino acid substitutions, preferably wherein the amino acid substitutions are conservative amino acid substitutions.

Preferably, the isolated or recombinant peptide comprises at least an amino acid sequence KVKKGVHRYFKKNKFY (SEQ ID NO:35), preferably RKVKKGVHRYFKKNKFY (SEQ ID NO:36); preferably FRKVKKGVHRYFKKNKFY (SEQ ID NO:37), preferably FFRKVKKGVHRYFK-KNKFY (SEQ ID NO:38), preferably KFFRKVKKGVHRYFKKNKFY(SEQ ID NO:39), preferably KKFFRKVKKGVHRYFKKNKFY (SEQ ID NO:40), preferably FKKFFRKVKKGVHRYFKKNKFY (SEQ ID NO:41), preferably RFKKFFRKVKKGVHRYFKKNKFY (SEQ ID NO:42), preferably KRFKKFFRKVKKGVHRYFKKNKFY (SEQ ID NO:43).

Preferably, the peptide may in total may have up to 5 amino acid substitutions. For example, the peptide may have up to 2 amino acid substitutions in the amino acid sequence VKKGVHRYFKKNKFY (SEQ ID NO:34) and an additional 3 amino acid substitutions in the rest of the SP27 sequence (KRFKKFFRKVKKGVHRYFKKNKFYIAA-TIPYYG (SEQ ID NO:25)).

Preferred peptides comprise
a) an amino acid sequence selected from:

```
SP27-63     K R F K K F F R K V K K G V H R Y F K K N K F Y
SP27-64       R F K K F F R K V K K G V H R Y F K K N K F Y I
SP27-65         F K K F F R K V K K G V H R Y F K K N K F Y I A
SP27-66           K K F F R K V K K G V H R Y F K K N K F Y I A A
SP27-67             K F F R K V K K G V H R Y F K K N K F Y I A A T
SP27-68               F F R K V K K G V H R Y F K K N K F Y I A A T I
SP27-69                 F R K V K K G V H R Y F K K N K F Y I A A T I P
SP27-70                   R K V K K G V H R Y F K K N K F Y I A A T I P Y
SP27-71                     K V K K G V H R Y F K K N K F Y I A A T I P Y Y
SP27-72                       V K K G V H R Y F K K N K F Y I A A T I P Y Y G
SP27-114            K F F R K V K K G V H R Y F K K N K F Y
SP27-115                      V K K G V H R Y F K K N K F Y
```

(see, SEQ ID NO: 97 and SEQ ID NO:44-54, respectively);

b) a retro-inverso sequence of a); or
c) a functional variant of a) or b), wherein the variant:
has one or more substitutions of an amino acid by a corresponding non-natural amino acid;
has one or more substitutions of an amino acid by a corresponding D-amino acid; and/or
has up to 5 amino acid substitutions, preferably wherein the amino acid substitutions are conservative amino acid substitutions.

The peptides and functional variants disclosed herein are useful for a number of applications including to inhibit biofilm formation or to degrade biofilms; as an anti-bacterial agent, anti-fungal agent, anti-viral agent, anti-parasitic agent, as a diagnostic, crop protectant, disinfectant, preservative anti-inflammatory agent, immune-modulating agent and/or anti-cancer agent as well as a therapeutic for the treatment of a bacterial, fungal, viral and/or parasitic infection, an inflammatory condition, or a cancer; or in the treatment of a condition resulting from bacterial, fungal, viral and/or parasitic infection, biofilm formation, an inflammatory condition, or a cancer. The peptides and functional variants disclosed herein preferably have bactericidal activity and in particular bactericidal activity on MDR *S. aureus* and/or MDR *P. aeruginosa*, preferably with low toxicity against human erythrocytes. Preferably, the peptide and functional variants disclosed herein have anti-bacterial, anti-viral, anti-fungal, anti-parasitic, anti-inflammatory and/or anti-cancer-activity.

The peptides as disclosed herein may be produced synthetically. For example, a peptide may be synthesized by commonly used solid-phase synthesis methods, e.g., methods that involve t-BOC or FMOC protection of alpha-amino groups, which are well known in the art. The peptides may also be produced using recombinant technology. Accordingly, the disclosure further provides nucleic acid molecules encoding the peptides. A nucleic acid as used in the disclosure is typically, but not exclusively, a ribonucleic acid (RNA) or a deoxyribonucleic acid (DNA). Based on the genetic code, a skilled person may determine the nucleic acid sequence that encodes the antibody variants disclosed herein. Based on the degeneracy of the genetic code, sixty-four codons may be used to encode twenty amino acids and translational terminal signal. As is known to a skilled person, codon usage bias in different organisms may effect gene expression level. Various computational tools are available to the skilled person in order to optimize codon usage depending on which organisms the desired nucleic acid will be expressed.

The disclosure further provides a vector comprising a nucleic acid sequence molecule according to this disclosure. The term "vector" as used herein refers to a nucleic acid molecule, such as a plasmid, bacteriophage or virus, capable of introducing a heterologous nucleic acid sequence into a host cell. A vector according to the disclosure allows the expression or production of a peptide encoded by the heterologous nucleic acid sequence in a host cell. It is within the purview of a skilled person to prepare suitable expression vectors for expressing the peptides disclosed herein. Suitable regulatory sequences including enhancers, promoters, translation initiation signals, and polyadenylation signals may be included. Additionally, depending on the host cell chosen and the vector employed, other sequences, such as an origin of replication, additional DNA restriction sites, enhancers, and sequences conferring inducibility of transcription may be incorporated into the expression vector. The expression vectors may also contain a selectable marker gene that facilitates the selection of host cells transformed or transfected. Examples of selectable marker genes are genes encoding a protein such as G418 and hygromycin that confer resistance to certain drugs, β-galactosidase, chloramphenicol acetyltransferase, and firefly luciferase.

When the nucleic acid is expressed in a cell, the cell produces a peptide according to the disclosure. Therefore, in one embodiment, a cell is provided comprising a nucleic acid or vector according to the disclosure. The host cells may be a mammalian, insect, plant, bacterial, or yeast cell. The disclosure further encompasses cell cultures that comprise the cells.

The disclosure further provides methods for transforming a host cell with a nucleic acid or vector as disclosed herein. "Transformation" refers to the introduction of a foreign nucleic acid into a recipient cell. Transformation of a host cell may result in transient expression of a recombinant protein by the cell, meaning that the recombinant protein is only expressed for a defined period of time. Alternatively, transformation of a recipient cell may result in stable expression, meaning that the nucleic acid is introduced into the genome of the cell and thus passed on to next generations of cells. Additionally, inducible expression of a recombinant protein may be achieved. An inducible expression system requires the presence or absence of a molecule that allows for expression of a nucleic acid sequence encoding a polypeptide of this disclosure. Examples of inducible expression systems include, but are not limited to, Tet-On and Tet-Off expression systems, hormone inducible gene expression system such as, for instance, an ecdysone inducible gene expression system, an arabinose-inducible gene expression system, and a *Drosophila* inducible expression system using a pMT/BiP vector (Invitrogen) that comprises an inducible metallothioneine promoter.

The disclosure further provides methods for producing the peptides of the disclosure comprising transforming a host cell with a vector as disclosed herein. Examples of suitable host cells include plant cells such as corn cells, rice cells, duckweed cells, tobacco cells (such as BY-2 or NT-1 cells), and potato cells. Examples of yeast cells are *Saccharomyces* and *Pichia*. Examples of insect cells are *Spodoptera frugiperda* cells, such as Tn5, SF-9 and SF-21 cells, and *Drosophila* cells, such as *Drosophila* Schneider 2 (S2) cells. Examples of mammalian cells that are suitable for expressing a peptide as disclosed include African Green Monkey kidney (Vero) cells, baby hamster kidney (such as BHK-21) cells, Human retina cells (for example, PER.C6 cells), human embryonic kidney cells (such as HEK293 cells), Madin-Darby Canine Kidney (MDCK) cells, Chicken embryo fibroblasts (CEF), Chicken embryo kidney cells (CEK cells), blastoderm-derived embryonic stem cells (e.g., EB14), mouse embryonic fibroblasts (such as 3T3 cells), Chinese hamster ovary (CHO) cells, and derivatives of these cell types.

In some embodiments, the methods for producing the peptides of the disclosure further comprise a step of harvesting, purifying and/or isolating the peptides. Methods for peptide purification are known to a skilled person and include, e.g., gel electrophoresis or chromatography methods.

In some embodiments, the disclosure provides a method for the preparation of a peptide as disclosed herein comprising:
  providing a nucleic acid molecule comprising a nucleic acid sequence encoding the peptide;
  transforming a host cell with the nucleic acid molecule;
  culturing the host cell under conditions that allow expression of the peptide;
  harvesting the peptide from the cells; and
  optionally, N-terminally or C-terminally modifying the peptide.

As disclosed further herein, the peptides of the disclosure exhibit a number of activities that may be advantageously used in both therapeutic and nontherapeutic applications. As such, the disclosure further provides compositions comprising one or more peptides as disclosed herein that are suitable for such uses. In one embodiment, the compositions are useful as a medicament for use in an individual. An individual refers to a human or animal, preferably wherein the animal is a vertebrate, in particular a mammal or bird. An individual, as used herein, may also refer to other organisms, for example, a plant. Accordingly, the disclosure provides compositions comprising one or more peptides as disclosed herein together with at least one pharmaceutically acceptable carrier, diluent and/or excipient. As used herein, the term "pharmaceutically acceptable" refers to those compositions or combinations of agents, materials, or compositions, and/or their dosage forms, that are within the scope of sound medical judgment, suitable for use in contact with the tissues of human beings and animals without excessive toxicity, irritation, allergic response, or other problem or complication, commensurate with a reasonable benefit/risk ratio. Furthermore, the term "pharmaceutically acceptable diluent or carrier" refers to a pharmaceutically acceptable material, composition or vehicle, such as a liquid or solid filler, diluent, excipient, solvent or encapsulating material, involved in carrying or transporting the peptide from one organ, or portion of the body, to another organ, or portion of the body.

The pharmaceutical composition may be administered by any suitable route and mode. As will be appreciated by the person skilled in the art, the route and/or mode of administration will vary depending upon the desired results. The pharmaceutical compositions may be formulated in accordance with routine procedures for administration by any routes, such as parenteral, topical (including ocular), oral, sublingual, transdermal, or by inhalation. Parenteral administration includes, e.g., intravenous, intramuscular, intra-arterial, intracoronary, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The compositions may be in any suitable forms, such as liquid, semi-solid and solid dosage forms. The compositions may be in the form of tablets, capsules, powders, granules, lozenges, creams or liquid preparations (in particular for administration to the skin or eye), such as sterile parenteral solutions or suspensions or in the form of a spray, aerosol or other conventional method for inhalation. The pharmaceutical compositions of the present disclosure include those suitable for oral, nasal, topical (including buccal and sublingual), rectal, vaginal and/or parenteral administration. In particular embodiments, the composition is a topical composition in the form of a cream, gel, ointment, lotion, foam, suspension, spray, aerosol, or powder aerosol. The compositions are particularly useful for administration to the skin.

The peptides may be formulated in the compositions for controlled release and/or targeted delivery carrier. As used herein, the term "controlled release" refers to the release of the peptide in a time-dependent manner. In one embodiment, controlled release refers to slow release. As used herein, the term "targeted delivery" refers to the release of the peptide in a site-directed manner. Preferably, a peptide is targeted to a site infected by bacteria, fungi, viruses and/or parasites or to the cancer. Controlled release and/or targeted delivery carriers are well known in the art. Non limiting examples of controlled release and/or targeted delivery vehicles are nanoparticles, microparticles, nanocapsules, microcapsules, liposomes, microspheres, hydrogels, polymers, lipid complexes, serum albumin, antibodies, cyclodextrins and dextrans. Targeted delivery is, for instance, achieved by providing a carrier with targeting groups on the surface thereof. Examples of such carrier comprising targeting groups are antibody-functionalized carriers, carriers having a site-specific ligand and carriers having a positive or negative surface charge. Preferred particles for controlled release and/or targeted delivery are nanoparticles, i.e., particles in the range of about 1 to 500 nm in diameter, preferably up to about 200 nm in diameter, and liposomes, optionally provided with targeting groups.

Actual dosage levels of the pharmaceutical compositions may be varied so as to obtain an amount of peptide that is effective ("effective amount") to achieve the desired therapeutic response for a particular patient, composition, and mode of administration, without being toxic to the patient. The selected dosage level will depend upon a variety of pharmacokinetic factors including the activity of the peptide, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts. The dosage and scheduling for the formulation that is selected may be determined by standard procedures well known by a skilled person. Such procedures involve extrapolating and estimating dosing schedule from animal models, and then determining the optimal dosage in a human clinical dose ranging study. The dosage in pharmaceutical compositions will vary depending upon a number of factors, such as the desired release and pharmacodynamic characteristics. Typical doses of administration of the peptide are between 0.01 and 100 mg per kg body weight. As disclosed further herein, the peptide compositions may be used in the treatment of humans, animals, and crop plants.

The disclosure further provides oral care products comprising a peptide as disclosed herein. Suitable oral care compositions include, e.g., toothpaste, dentifrice, tooth powder, tooth gel, subgingival gel, mouthrinse/mouthwash, artificial saliva, denture product, mouthspray, lozenge, oral tablet, and chewing gum.

The peptides are useful as disinfectants and may be used in cleaning compositions together with, or as alternatives to, other disinfectants commonly used in the art. Cleaning products include, e.g., surface cleaning compositions (for example, glass, floor, counter, bath, toilet bowl, sink, appliance and furniture cleaning compositions); deodorants (for example, solid, liquid and spray deodorants air and/or surface deodorants); disinfectants (for example, spray and solid air or surface disinfectants); waxes and other surface protecting and/or polishing compositions; laundry compositions (for example, detergents, fabric softeners and whiteners); and rug shampoo. Such cleaning compositions may further include detergents, enzymes (e.g., proteases), ethanol, propanol, propylene glycol, isopropanol, or other alcohols. The cleaning composition may be provided as a solution, including a concentrate that should be diluted prior to use, as well as in the form of wipes impregnated with the cleaning composition.

The disclosure further provides method for disinfecting a surface or composition, the method comprising contacting the surface or composition or providing the surface or composition with the isolated or recombinant peptide and/or the composition as disclosed herein. Suitable surfaces and compositions are disclosed herein. For example, in an exemplary embodiment, a surface (e.g., a hospital floor or sink, dental unit water system) is contacted with a cleaning composition comprising one or more peptides of the disclosure.

The peptides are also useful as preservatives and may be used in compositions together with, or as alternatives to, other preservatives commonly used in the art. In some embodiments, the composition is a cosmetic product, e.g., a cosmetic cream, gel, lotion, shampoo, conditioner, body rinse, body lotion, color agent, skin color agent, eye color agent, or perfume. In some embodiments, the composition is an ophthalmic composition suitable for administration to the eye. Preferred ophthalmic compositions include contact lens solution, eyewash, eye drops, and eye gel.

In some embodiments, the composition is a food product. Pathogenic microorganisms in foods may cause infections or intoxication of subjects or change the look, consistency, flavor and/or odor of food products. The peptides of the disclosure may be applied directly to a food product (such as spraying or washing), mixed directly into a food product (e.g., added to a sauce or dairy product), or applied to the food packaging (e.g., a plastic container). Suitable food products include, e.g., vegetables, fruit, meat products, bakery products (baked goods) and dairy products.

The disclosure further provides articles coated with the peptides disclosed herein. Suitable articles include cleaning products such as wipes and cloths that have been impregnated with the peptides. Suitable articles also include medical devices and surgical equipment, or articles for storing the devices and equipment or articles that come into contact with the devices and equipment. Medical devices include, e.g., wound or tissue dressings, prosthetics (hip implants, dental implants, prosthetic joint, a voice prosthetic, a penile prosthetic), stents (e.g., biliary, urethral, ureteral, tracheal, coronary, gastrointestinal and esophageal stents), a mechanical heart valve, a cardiac pacemaker, an arteriovenous shunt, a schleral buckle, catheters (e.g., central venous catheter, an intravascular catheter, an urinary catheter, a Hickman catheter, a peritoneal dialysis catheter, an endrotracheal catheter), tympanostomy tube, a tracheostomy tube, a surgical suture, a bone anchor, a bone screw, an intraocular lens, a contact lens, an intrauterine device, an aortofemoral graft, or a vascular graft. Surgical instruments include, e.g., clamp, forceps, scissor, skin hook, tubing, needle, retractor, scaler, drill, chisel, rasp, or saw. Suitable articles also include articles that come in contact with or store such medical devices or surgical equipment, e.g., a contact lens case.

In some embodiments, the article is coated with a peptide as disclosed herein, in particular wherein the coating allows for the slow release of the peptide. In particular, the coating is biodegradable and comprises a material selected from the group consisting of PLA (poly lactic acid), PGA (poly glycolic acid), polycaprolactone (PCA), polyethylene oxide (PEO), polydioxanone (PDS), polycaprolactone (PCL), polypropylene fumarate, polymers derived from lactones, such as lactide, glycolide and caprolactone, carbonates such as trimethylene carbonate and tetramethylene carbonate, dioxanones, ethylene glycol, polyester amide (PEA) ethylene oxide, esteramides, γ-hydroxyvalerate, β-hydroxypropionate, α-hydroxy acid, hydroxybuterates, hydroxy alkanoates, polyimide carbonates, polyurethanes, polyanhydrides, and combinations thereof, polysaccharides such as hyaluronic acid, chitosan and cellulose, and proteins such as gelatin and collagen.

The peptides and compositions disclosed herein are useful for treating and/or preventing various disorders and conditions. In some embodiments, the peptides and compositions disclosed herein are useful for treating and/or preventing bacterial infection, particularly in a human, animal and plants. As used herein, "treating and/or preventing bacterial infection" refers to delaying, inhibiting or preventing a bacterial infection as well as delaying, inhibiting, preventing, or reducing the severity of one or more symptoms of a bacterial infection. Examples of pathogenic bacteria that may cause infections in humans or animals that are treatable with the peptides disclosed herein include acinetobacters, listeriae, escherichiae, chlamydiae, rickettsial bacteria, mycoplasma's, mycobacteria, staphylococci, streptococci, pneumonococci, meningococci, klebsiella, pseudomonae, legionellae, diphtheria, salmonellae, bacilli, *Vibrio cholerae*, tetanus, clostridiae, bacilli, yersiniae, and Leptospira bacteria. Preferably, the bacteria are gram-negative bacteria. Accordingly, the disclosure provides the use of the peptides as disclosed herein for treating, including prophylactic treatment, of a human or animal. The peptides, nucleic acids, vectors, or compositions comprising same, may be administered to an individual in need thereof by any means known to a skilled person and may be administered to an individual at risk of developing a bacterial infection or to an individual after a bacterial infection has been diagnosed.

The peptides and compositions disclosed herein are also useful for ex vivo applications, e.g., as anti-bacterial agents. Method are disclosed herein for inhibiting bacteria on a surface or in a composition comprising providing the surface or composition with a peptide as disclosed herein. As used herein, "inhibiting bacteria" refers to impairing, inhibiting or slowing bacterial growth as well as promoting bacteria death.

As used herein, a "surface" refers to any hard or soft surface, such as those found in household environments, in industrial environments, and surfaces of food products such as fruits, vegetables and meat. A surface includes glass, metal, porous, and non-porous surfaces. It also pertains to exterior and interior surfaces of equipment that may be contaminated, such as those found in the food industry or the medical equipment found in hospitals and health care facilities, as well as plumbing systems (e.g., sink drain), countertops, building materials, ductwork, and clean rooms. A surface also refers to the surface of a medical or surgical device. A surface also refers to the interior or exterior of pipes, for example, drains. A surface also includes the surfaces of plants (e.g., leaves, roots, seeds, etc.). In some embodiments, a surface refers to an exterior or interior surface of a human or animal body (e.g., mucosal membrane, oral cavity). In some embodiments, the surface is not an in vivo surface (or rather is not a surface of a human or animal body). Treatment of the surface is accomplished by any means known to those of ordinary skill in the art including, but not limited to, dipping, soaking, brushing, spraying, mopping, washing, or the like. The length of treatment required will vary according to treatment conditions, the selection of which is known to those skilled in the art.

As used herein, a "composition" may be liquid, solid, or semi-solid and may include one or more compounds or materials. Suitable compositions include those already described, e.g., medicaments/pharmaceutical preparations, oral care compositions, cleaning compositions, food products, cosmetic products, and ophthalmic compositions.

In some embodiments, the peptides are useful for inhibiting, inhibiting, and/or reducing antibiotic resistant bacteria. As used herein, "antibiotic-resistant bacteria" refers to bacteria that have acquired an inherited mutation/alteration allowing them to grow at higher concentrations of an antibiotic irrespective of the duration of treatment. This may be quantified by the minimum inhibitory concentration (MIC) of a particular antibiotic. MIC refers to the lowest concentration of an antibiotic that prevents the visible growth of a bacterium. In a preferred embodiment, the antibiotic resistant bacteria is selected from *Enterococcus faecium, Staphylococcus aureus, Klebsiella pneumoniae, Acinetobacter baumannii, Pseudomonas aeruginosa*, and *Enterobacter* species.

In some embodiments, the peptides are useful for inhibiting antibiotic tolerant bacteria. See, Brauner et al., *Nature* 2016, 14:321-330, for a review on antibiotic tolerance. As used herein, antibiotic tolerance refers to the ability of a micro-organism to survive transient exposure to high doses of an antibiotic for long periods. In contrast to antibiotic resistance, the MIC of a particular antibiotic does not change in case of an antibiotic tolerant bacterium. Tolerance may be inheritable or non-inheritable and is generally associated with the slowed growth or dormancy.

In some embodiments, the peptides are useful for inhibiting bacterial persisters. See, Brauner et al., *Nature* 2016, 14:321-330, for a review on persistence. As used herein, antibiotic persistence refer to the ability of a sub-population of bacteria to survive antibiotic treatment. Persistence may be detected by a bimodal time-kill curve, demonstrating the presence of at least two coexisting subpopulations of bacteria. Generally, bacterial persisters have a slower growth rate than the majority of the bacterial population or they have a transient decrease in antibiotic sensitivity, e.g., by the overexpression of a resistance factor.

In some embodiments, the peptides are useful for inhibiting biofilm formation or for removing or reducing a biofilm. As used herein, inhibiting biofilm formation refers to a reduction or prevention in the amount of biofilm formed as compared to the amount of biofilm that would have formed in the absence of treatment with the peptides. Such a reduction may be due to a decrease in microbial growth, an increase in microbial killing, degradation of the extracellular matrix, reduced production of matrix and/or a modulation in the ability of a microbe to attach to a surface. Similarly, removing or reducing a biofilm may include a decrease in microbial growth, an increase in microbial killing, degradation of the extracellular matrix, reduced production of matrix and/or a modulation in the ability of a microbe to attach/detach to a surface (in particular, detachment from a surface may be promoted). The disclosure further provides methods for inhibiting biofilm formation on a surface (as disclosed herein) and/or degrading the biofilm from a surface, the method comprising contacting the surface with the isolated or recombinant peptide and/or the composition as disclosed herein.

As used herein, microbial biofilms develop when micro-organisms adhere to a surface and produce extracellular polymers that facilitate adhesion and provide a structural matrix. The extracellular matrix comprises exopolysaccharides, proteins and nucleic acids. Biofilms may form on living or non-living surfaces and are found in natural, industrial and hospital settings. Biofilms may contain many different types of micro-organisms, e.g., bacteria, archaea, protozoa, fungi and algae.

Biofilms may negatively impact human and animal health. Biofilms have been found to be involved in a wide variety of clinical infections in the body, by one estimates 80% of all infections. For example, biofilms are involved in bacterial vaginosis, urinary tract infections, catheter infections, middle ear infections, gingivitis, coating contact lenses. Examples of lethal infections whereby biofilms are involved are, endocarditis, infections in cystic fibrosis, infections of permanent implants such as joint prosthesis, heart valves and intervertebral disc indwelling devises, e.g., catheters, intravenous lines etc. Bacterial biofilms may delay cutaneous wound healing and reduce topical antibacterial efficiency of conventional antibiotics in healing or treating infected skin wounds, skin infections or urinary tract infections. In addition, biofilms may form on teeth of animals or humans as dental plaque. These biofilms contribute to tooth decay and gum disease. Biofilm formation may also occur along the gastrointestinal tract. A "healthy" biofilm of the gastrointestinal tract is beneficial and has lubricating and anti-inflammatory properties. However, a disruption in the normal biofilm of the intestine may lead to an "unhealthy" biofilm that is associated with bloating, stomach cramps, inflammatory bowel disease, ulcerative colitis, and Crohn's Disease (see, e.g., Von Rosenvinge et al., Pathog. Dis. 2013; 67(1): 25-38). *Helicobacter pylori* biofilms, for example, are associated with peptic ulcer disease.

Implantable or insertable medical devices are frequently susceptible to bacterial infection and/or biofilm formation. This is particularly relevant for devices that are adapted for long-term use, e.g., longer than a few days or weeks. Microbes often colonize on and around the medical device and, upon attaching to surfaces of the device, proliferate and form aggregates resulting in biofilm formation. This may lead to the failure of the working of the device.

Biofilms commonly grow in showers as well as on floors and counters making it difficult to maintain sanitary conditions in food preparation areas and medical settings. Biofilms are also found in marine engineering systems, such as pipelines of the offshore oil and gas industry may lead to substantial corrosion problems. At least 20% of corrosion is caused by micro-organisms that are attached to the metal subsurface. Biofilms may form on the surface of stagnant pools of water. Biofilms may be found on the surface of plants and may contribute to crop disease. Examples of crop disease related to biofilms include Citrus Canker, Pierce's Disease of grapes and Bacterial Spot of plants such as peppers and tomatoes.

Figure 4:
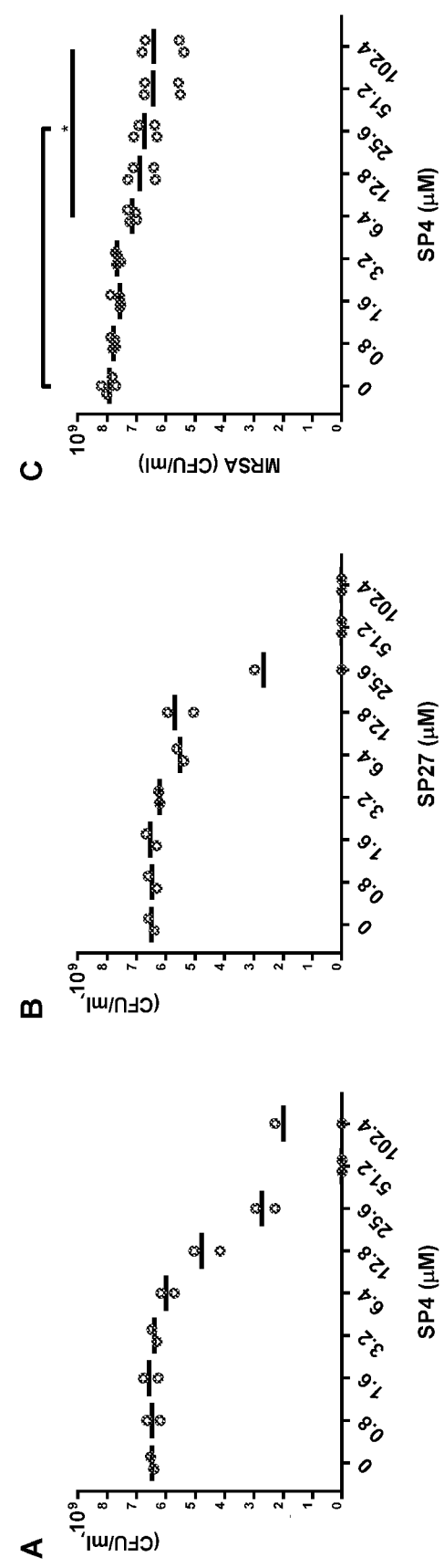
FIG. 4: Degradation of an established *A. baumannii* and *S. aureus* biofilm by SP4 and SP27. Dose-dependent degradation of a 24-hour biofilm of *A. baumannii* RUH 875 after a 2-hour treatment with SP4 (Panel A) and SP27 (Panel B). Results are expressed as the CFU/ml. Panel C) Dose-dependent degradation of a 24-hour matured biofilm of *S. aureus* LUH 14616 after a 2-hour treatment with SP4. The results are expressed as the CFU/ml. Significance compared to control (0 μM) was calculated with the Mann-Whitney U test (*P<0.05).
Figure 5:
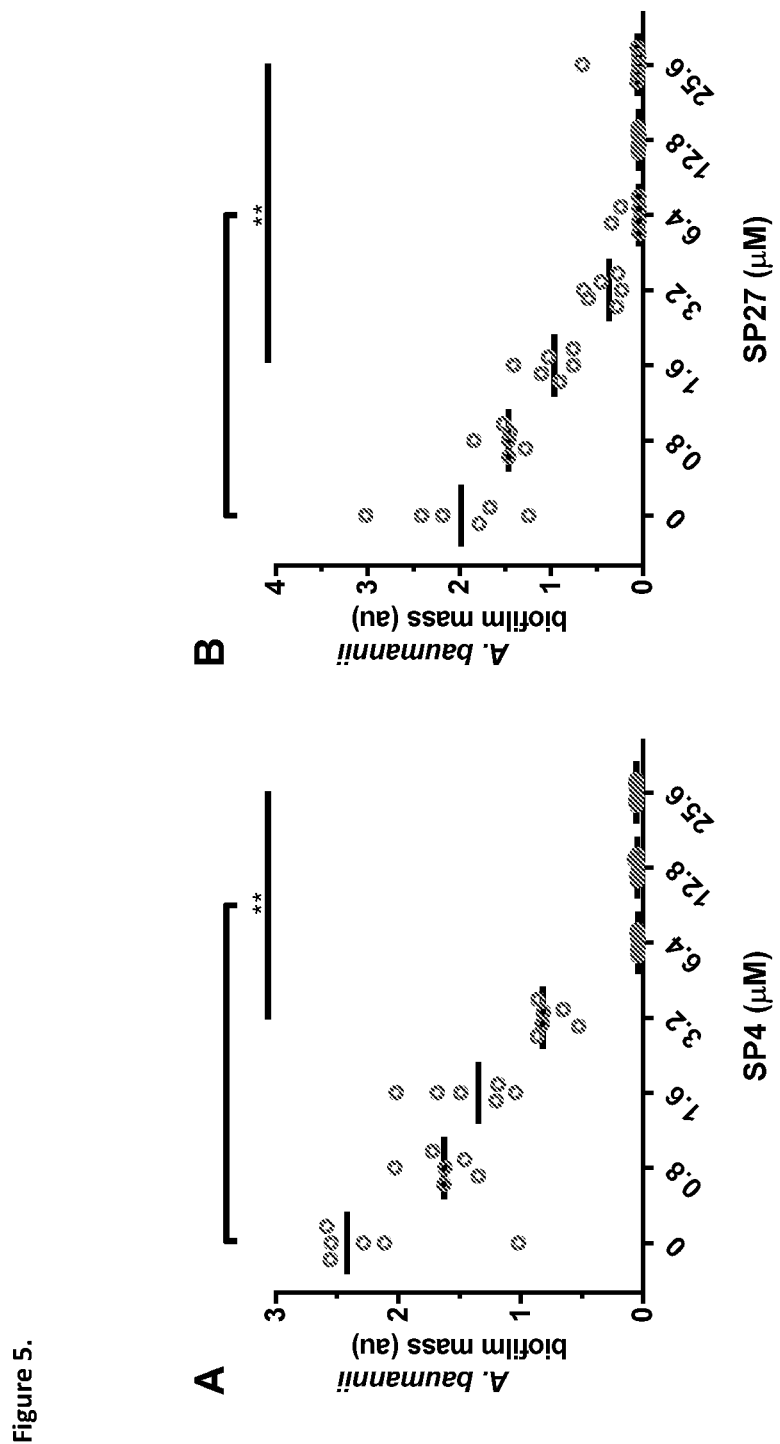
FIG. 5: Prevention of biofilm formation by SP4 and SP27. *A. baumannii* RUH 875 bacteria were incubated with increasing SP4 (A) and SP27 (B) concentrations in BM2 medium for 24 hours. Thereafter, biofilms were stained with crystal violet and the biofilm mass quantified by determining the optical density of the crystal violet staining. Results are medians of sixplicates from one experiment. Results are expressed as the biofilm mass in arbitrary units (au). Significance compared to control (0 μM) was calculated with the Mann-Whitney U test (**P<0.01).

Although not wanting to be bound by theory, the limited access to nutrients in a biofilm is thought to result in metabolically inactive bacteria leading to bacterial "tolerance" and "persistence" as described herein. The reliance of antibiotics on bacterial growth and multiplication renders these compounds generally ineffective against biofilm. In contrast, FIGS. 4 and 5 depict the ability of the peptides disclosed herein to degrade biofilms and prevent their formation, respectively.

The peptides and compositions disclosed herein are also useful for treating and/or preventing viral infection, particularly in a human or animal. As used herein, "treating and/or preventing viral infection" refers to delaying, inhibiting or preventing a viral infection, decreasing the viral load as compared to the viral load without treatment, as well as delaying, inhibiting, preventing, or reducing the severity of one or more symptoms of a viral infection. Examples of pathogenic viruses that may cause infections in humans or animals that are treatable with polypeptides and compositions of the disclosure include, but are not limited to, A, B or C hepatitis, herpes virus (for instance, VZV, HSV-I, HAV-6, HSV-II, CMV, Epstein-Barr virus), adenovirus, influenza virus, flaviviruses (e.g., yellow fever, dengue and chikungunya virus), echovirus, rhinovirus, coxsackie virus, coronavirus, respiratory syncytial virus (RSV), rotavirus, Morbillivirus, rubella virus, parvovirus, vaccinia virus, HTLV virus, papillomavirus, poliovirus, rabies virus and human immunodeficiency virus (HIV virus; e.g., type I and II). The peptides, nucleic acids, vectors, or compositions comprising same, may be administered to an individual in need thereof by any means known to a skilled person and may be administered to an individual at risk of developing a viral infection or to an individual after a viral infection has been diagnosed.

The peptides and compositions disclosed herein are useful for ex vivo applications, e.g., as anti-viral agents. Method are disclosed herein for inhibiting viruses on a surface or in a composition comprising providing the surface or composition with a peptide as disclosed herein. As used herein, "inhibiting a virus" refers to inhibiting or slowing viral growth/replication as well as promoting viral inactivation/degradation.

Virus plaque assays may be used to assess the antiviral activity of a peptide as disclosed herein. In short, a virus inoculum is exposed to the peptide prior to infection of a permissive cell monolayer. After a standard interval, the virus titer in the cellular extracts is determined using multiple dilutions of these extracts by infecting fresh cell monolayers and quantifying their effects on the cell monolayer.

The peptides and compositions disclosed herein are useful for treating and/or preventing fungal infection, particularly in a human, animal or crop plant. As used herein, "treating and/or preventing fungal infection" refers to delaying, inhibiting or preventing, or reducing the severity of one or more symptoms of a bacterial infection. Examples of pathogenic fungi that may cause infections in humans, animals or crop plants that are treatable with polypeptides and compositions of this disclosure include, but are not limited to *Candida* (e.g., *albicans, krusei, glabrata, tropicalis*), *Aspergillus* (e.g., *fumigatus, niger*), *Cryptococcus neoformans*, *Histoplasma capsulatum*, Genus Mucorales, *Blastomyces dermatitidis, Paracoccidioides brasiliensis*, and *Coccidioides immitis*. Accordingly, the disclosure provides the use of the peptides as disclosed herein for treating a human or animal. The peptides, nucleic acids, vectors, or compositions comprising same, may be administered to an individual in need thereof by any means known to a skilled person and may be administered to an individual at risk of developing a fungal infection or to an individual after a fungal infection has been diagnosed.

The peptides and compositions disclosed herein are useful for ex vivo applications, e.g., as anti-fungal agents. Method are disclosed herein for inhibiting fungi on a surface or in a composition comprising providing the surface or composition with a peptide as disclosed herein. As used herein, "inhibiting fungi" refers to inhibiting or slowing hyphenation, as well as promoting fungal death.

The peptides and compositions disclosed herein are useful for treating and/or preventing parasitic infection, particularly in a human or animal. As used herein, "treating and/or preventing parasitic infection" refers to delaying, inhibiting or preventing, or reducing the severity of one or more symptoms of a parasitic infection. Examples of pathogenic parasites that may cause infections in humans or animals that are treatable with polypeptides and compositions of the disclosure include, but are not limited to, *Entamoeba histolytica, Plasmodium* (e.g., *falciparum, vivax*), *Entamoeba, Giardia, Balantidium coli, Acanthamoeba, Cryptosporidium* sp., *Pneumocystis carinii, Babesia microti, Trypanosoma* (e.g., *brucei, cruzi*), *Leishmania* (e.g., *donovani*), and *Toxoplasma gondii*. Accordingly, the disclosure provides the use of the peptides as disclosed herein for treating a human or animal. The peptides, nucleic acids, vectors, or compositions comprising same, may be administered to an individual in need thereof by any means known to a skilled person and may be administered to an individual at risk of developing a parasitic infection or to an individual after a parasitic infection has been diagnosed.

The peptides and compositions disclosed herein are useful for ex vivo applications, e.g., as anti-parasitic agents. Method are disclosed herein for inhibiting parasites on a surface or in a composition comprising providing the surface or composition with a peptide as disclosed herein. As used herein, "inhibiting parasites" refers to inhibiting or slowing down parasitic growth and/or development as well as promoting parasitic death.

For assessment of anti-parasitic activity, a peptide as disclosed herein and a parasite are incubated for a standard time interval. Thereafter, the metabolic activity of the parasites may be analyzed directly, for instance, by an MTT assay, or the parasites are transferred to mammalian cells and, after incubation, parasite multiplication in these cells is assessed by microscopy.

The peptides and compositions disclosed herein are useful for treating an inflammatory condition or modulating an immune response, particularly in a human or animal. In particular, the inflammatory condition is an inflammatory response in an individual suffering from a bacterial, fungal, viral and/or parasitic infection. While not wishing to be bound by theory, the anti-inflammatory activity of peptides disclosed herein may be achieved by inhibiting, reducing or preventing the release of pro-inflammatory cytokines/molecules upon exposure to microbial compounds, such as lipoteichoic acid (LTA), peptidoglycan (PG) and/or lipopolysaccharides (LPS). The peptides are thus useful as anti-inflammatory agents as they neutralize the pro-inflammatory actions of microbial endotoxins such as lipoteichoic acid, peptidoglycan and lipopolysaccharides thereby inhibiting, reducing or preventing influx of neutrophils, macrophages/monocytes and lymphocytes and the release of pro-inflammatory compounds by the infected subject. Accordingly, the disclosure further provides methods for inhibiting the release of pro-inflammatory compounds comprising contacting a cell capable of releasing pro-inflammatory compounds with a peptide as disclosed herein. Contacting may be performed in vivo and in vitro.

Anti-inflammatory activity may be measured by methods known in the art. One example of such method is a lipopolysaccharide neutralization assay. In this method, a polypeptide of the disclosure is mixed with 1 mg of lipopolysaccharides and incubated for 60 minutes. Thereafter, these mixtures were added to 4 times diluted fresh human blood and 18 hours thereafter the level of cytokines (IL-8, IL-12p40) in the blood sample are measured by ELISA.

The disclosure further provides the use of peptides as disclosed herein to redirect the tumor-tolerating immune response towards a tumor-controlling response. Redirection of the immune response may be measured by methods known in the art. One example of such a method is the redirection of the MCF-driven as well as tumor conditioned medium-driven differentiation of monocytes towards macrophages with a pro-inflammatory signature.

The disclosure further provides the use of the peptides as disclosed herein as diagnostics. In particular, the peptides may be used to detect a bacterial, fungal, viral and/or parasitic infection. For example, a peptide may be coupled to a suitable moiety such as a biotin, a fluorescein label, a near infrared dye or a radioactive isotope. The labelled peptide may then be administered to an individual having or suspected of having an infection. The peptide may then localize to the site of infection, if present, and may be detected by suitable means.

The peptides and compositions disclosed herein are useful for protecting plants and may be used in methods for treating and/or preventing infection of a plant, particularly in a crop plant. As used herein, "treating and/or preventing infection of a plant" refers to delaying, inhibiting or preventing, or reducing the severity of infection or of one or more symptoms of an infection in the plant. Examples of pathogenic infections that may cause infections of a plant that are treatable with polypeptides and compositions of the disclosure include, but are not limited to, fungi from the Ascomycetes and Basidiomycetes species, bacteria such as *Burkholderia*, Proteobacteria (e.g., *Xanthomonas* and *Pseudomonas*) and viruses such as Tobacco mosaic virus, Cauliflower mosaic virus, Cucumber green mottle mosaic virus and Pepino mosaic virus. Accordingly, the disclosure provides the use of the peptides as disclosed herein for plant protection. The peptides, nucleic acids, vectors, or compositions comprising same, may be provided to a plant by any means known to a skilled person and may be provided to a plant at risk of developing an infection or after an infection has been diagnosed. For example, plants may be sprayed with a composition as disclosed herein if crops in a neighboring field are infected.

For assessment of protective activity, a peptide as disclosed herein is administered to a plant. Thereafter, the plant is infected with a pathogen, for instance, with a bacteria, virus, fungi or parasite. After incubation for a time sufficient to infect the plant, the plant is analyzed for infection symptoms. Preferably, the plant is compared to other plants infected with the same pathogen that were not pre-treated with the peptide.

The disclosure further provides a method for protecting a plant comprising contacting the plant with a peptide, nucleic acid molecule, vector, and/or composition as disclosed herein. As used herein, "protecting a plant" refers to protecting a plant against disease and/or infection. Preferably, protecting against infection with bacteria, fungi, viruses and/or parasites, and/or reducing the severity of bacterial, fungal, virus and/or parasite infections. Protection may result in a reduction of the multiplication of the bacteria, fungi, viruses and parasites. Protection may result from killing the bacteria, fungi, viruses and/or parasites. Preferably, the methods as described herein comprise exposing a plant or plant part to an effective dosage of the peptide as described herein.

The peptides and compositions disclosed herein are useful for treating a cancer in an individual. In some embodiments, the peptides and compositions disclosed herein are useful for promoting an anti-tumor immune response. In some embodiments, topical compositions are provided comprising the peptides disclosed herein. In some embodiments, the cancer is selected from melanomas, epithelioid cervix carcinomas and ovarian carcinomas.

The disclosure further provides the use of the peptides disclosed herein in screening and research applications. In some embodiments, methods are provided comprising providing the isolated or recombinant peptide, the nucleic acid molecule, the vector and/or the composition as disclosed herein to a system. Exemplary systems include cell culture, cell-free in-vitro systems, animal models, and organoid cultures. As used herein, cell culture refers to any kind of cell culture, including mammalian cell culture, insect cell culture, plant cell culture, bacterial cell culture, yeast cell culture. Cell culture includes both small and large scale cell culture, for example, at industrial scale.

In such systems, the peptides may be used to induce or inhibit various processes. For example, the growth of in vitro cultured carcinoma cells may be reduced or the excretion of cytokines by in vitro-cultured immune cells may be influenced. The disclosed systems are also useful for performing screening assays.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, the additional component(s) not altering the unique characteristic of the disclosure.

The articles "a" and "an" are used herein to refer to one or to more than one (i.e., to at least one) of the grammatical object of the article. By way of example, "an element" means one element or more than one element.

REFERENCES

Bahar A. A., Ren D. "Antimicrobial peptides." *Pharmaceuticals*. 2013; Vol. 6: p 1543-15'75; doi:10.3390/ph6121543.
Boucher H. W., Talbot G. H. et al. "Bad Bugs, No Drugs: No ESKAPE! An Update from the Infectious Diseases Society of America." *Clin. Infect. Dis.* 2009; Vol. 48: p 1-12.
Brauner et al. Distinguishing between resistance, tolerance and persistence to antibiotic treatment. *Nature* 2016, Vol. 14: p 321-330.
Cai S., Qiao X. et al. "Python cathelicidin CATHPb1 protects against multidrug-resistant staphylococcal infections by antimicrobial-immunomodulatory duality." *J. medicinal chemistry* 2018; Vol. 61: p 2075-2086.
Cho Y. C., Lee S. H. et al. "Enhanched IL-12p40 production in LPS-stimulated macrophages by inhibiting JNK activation by artemisinin." *Arh. Pharm. Res.* 2012; Vol. 35: p 1951-1968.
De Kraker M. E. A., Stewardson A. J., Harbarth S. "Will 10 Million People Die a Year due to Antimicrobial Resistance by 2050?" *PLoS Med.* 2016; doi:10.1371/journal.
De Latour F. A., Amer L. S. et al. "Antimicrobial activity of the *Naja atra* cathelicidin and related small peptides." *BBRC.* 2010; Vol. 396: p 825-830.
Dean S. N. et al. "Natural and synthetic cathelicidin peptides with anti-microbial and anti-biofilm activity against *Staphylococcus aureus*." *BMC Microbiology* 2011; doi: 10.1186/1471-2180-11-114.
Falcao C. B. et al. Vipericidins; a novel family of cathelicidin-related peptides from the venom gland of South American pit vipers. *Aminoacids* 2014; Vol 46: p 2561-2571.
Hoiby N., Bjarnsholt T. et al. "Antibiotic resistance of bacterial biofilms." *International J. Antimicrobial Agents* 2010; Vol. 35: p 322-332.
Kościuczuk E. M., Lisowski P. et al. "Cathelicidins: family of antimicrobial peptides. A review." *Mol. Biol. Rep.* 2012; Vol. 39: p 10957-10970.
O'Neill. "Tackling drug-resistant infections globally: Final report and recommendations." 2016; on the world-wide web at amr-review.org/sites/default/files/160518_Final%20paper_with%20cover.pdf.
Olsen I. "Biofilms-specific antibiotic tolerance and resistance." *Eur. J. Clin. Microbiol. Infect. Dis.* 2015; Vol. 34: p 877-886.
Overhage J., Campisano A. et al. "Human host defense peptide LL-37 prevents bacterial biofilm formation." *Infect. Immun.* 2008; Vol. 76: p 4176-4182.
Scott M. G., Davidson D. J. et al. "The human antimicrobial peptide LL-37 is a multifunctional modulator of innate immune responses." *J. Immunol.* 2002; Vol. 169: p 3883-3891.
Shek K. C., Tsui K. L. et al. "Oral bacterial flora of the Chinese cobra (*Naja atra*) and bamboo pit viper (*Trimeresurus albolabris*) in Hong Kong SAR, China." *Hong Kong Med. J.* 2009; Vol. 15: p 183-190.
Van der Does A. M. et al. LL-37 directs macrophage differentiation toward macrophages with a pro-inflammatory signature. *J. Immunol.* 2010; Vol 185: p 1442-1449.
Von Rosenvinge et al. Microbial biofilms and gastrointestinal diseases. Pathog. Dis. 2013; 67: p 25-38.
Wang H. et al. BF30 selectively inhibits melanoma cell proliferation via cytoplasmic membrane permeabilization and DNA-binding in vitro and in Bl6F10-bearing mice. *Eur. J. Pharmacol.* 2013; Vol 707: p 1-10.
Zhao F., Lan X. Q. et al. "King cobra peptide OH-CATH30 as a potential candidate drug through clinic drug-resistant isolates." *Zoological research*. 2018; Vol. 39: p 87-96.

The disclosure is further explained in the following examples. These examples do not limit the scope of the disclosure, but merely serve to clarify the disclosure.

EXAMPLES

Example 1

The present study is to identify optimal candidates for the development of novel agents. In this connection, first compared were the antibacterial and hemolytic activities of cathelicidins from various snakes. From this screening, the two most promising peptides were selected for further investigation studies of, i.e., their ability to kill multidrug resistant bacteria, to interfere with biofilm formation, to induce resistance, to modulate inflammatory responses, and to kill cancer cells.

In order to select promising antimicrobial peptides sequences encoding for cathelicidins found in the genome of various snakes were tested for their bactericidal activity against MRSA and multi drug resistant (MDR) *P. aeruginosa* with an in vitro killing assay. The peptides were also tested for their hemolytic activity as an indicator for their toxicity. In this hemolysis assay, red blood cells were mixed with the peptide. If the peptide was toxic, the cells would lyse and thereby release their hemoglobin, which could be measured. As a positive control TRITON® X-100 was used, this is a surfactant that lyses the red blood cells.

The snake peptides that had a promising antimicrobial activity and a low toxicity were selected and tested more extensively. As a start the two most potent peptides, being SP4 and SP27, were tested further for antibacterial activity against the multidrug resistant strains of the ESKAPE panel and colistin-resistant *E. coli* in a killing assay.

Next, the ability of MRSA to form resistance against SP4 and SP27 was assessed in a resistance development assay. In this assay the bacteria are incubated with peptide in a serial passing, with the half MIC being used for the subsequent passage to select for resistant isolates.

The peptides were tested on MDR *A. baumannii* for biofilm degrading activity and the ability to prevent biofilm formation. For the biofilm degradation an established biofilm of 24 hours was grown and then treated with the peptide, where after sonicating the number of viable bacteria could be determined. For the biofilm preventing ability the bacteria and peptide are incubated together for 24 hours. This incubation takes place in biofilm medium 2 (BM2), this is a minimal medium allowing bacteria to survive and form a biofilm (Overhage et al., 2008). After incubation a crystal violet stain was used to assess the mass of the formed biofilms.

To simulate a more in vivo like experiment the ability of SP4 and SP27 to reduce a MRSA colonization on ex vivo human skin was tested. Therefore, ex vivo skin punches have been inoculated with bacteria and thereafter treated with peptide. After treatment the number of viable bacteria could be determined.

To determine if the peptides also have immunomodulatory effects, the chemotactic activity, the lipopolysaccharide (LPS) neutralizing effect and the ability to redirect M-CSF-driven monocyte-macrophage differentiation were examined. For the chemotactic effect neutrophils were obtained after ficoll separation and the use subsequent lysis of the red blood cells within the neutrophil-containing fraction. The neutrophils were added to an insert with the peptide in the lower compartment as chemoattractant. As a positive control fMLP (N-formyl-Met-Leu-Phe) was used, this is a peptide with potent chemotaxis activities (sigma Aldrich cat number F3506). After the incubation period the number of migrated neutrophils in the lower compartment was measured by FACS. The ability of the peptides to neutralize LPS was tested in a LPS neutralization assay. The LPS was preincubated with the peptide and added to whole blood. If the LPS is neutralized by the peptide it will not be able to stimulate the IL-12p40 production by the blood cells (Cho et al., 2012), measured with an ELISA. The ability of the peptides to redirect monocyte-macrophage differentiation was assessed in cultures of human monocytes exposed to M-CSF (van der Does at al., 2010). Finally, the tumoricidal activity of the peptides was assessed in cultures of primary human melanocytes and 4 different melanoma cell line cells.

Materials and Methods:
Bacterial Strains and Culturing

*Enterococcus faecium* (LUH 15122), *Staphylococcus aureus* (LUH 14616), *Klebsiella pneumoniae* (LUH 15104), *Acinetobacter baumannii* (RUH 875), *Pseudomonas aeruginosa* (LUH 15103), *Enterobacter cloacae* (LUH 15114) and *Escherichia coli* (LUH 15117) were used. Prior to experimentation the bacteria were taken from a glycerol stock stored at −80° C. and cultured overnight on sheep blood agar plates at 37° C. On the day of experimentation the bacteria were cultured in tryptic soy broth (TSB; Oxoid) for 2.5 hours at 37° C. and 200 rpm to a mid-logarithmic phase. The bacterial suspension was washed in phosphate buffered saline (PBS; pH 7.4), centrifuged for 10 minutes at 3000 rpm, and resuspended in PBS to the desired concentration, as determined by measuring the absorbance at 600 nm.

Peptides

Mining the genomes of 17 different snake species (see Table 1) for genes encoding members of the cathelicidin family resulted in the identification of 35 different genomic sequences. The predicted amino acid sequences of the various mature snake cathelicidins were produced using solid phase peptide synthesis by F-MOC technology. The peptides were over 98% pure as assessed by HPLC. In addition, batch of HPLC-purified SP4 and SP27 were prepared. Furthermore, a set of snake peptide 4 shortened at the N and the C termini with one up to 10 amino acids was prepared.

Bactericidal Activity of Peptides

A bacterial suspension of $5 \times 10^6$ CFU/ml was added to peptides solutions ranging from final concentrations of 0.8 µM to 102.4 µM in PBS with either 50% (v/v) pooled human plasma (Sanquin) or 50% pooled urine (from healthy volunteers) in a polypropylene 96-well flat-bottom plate (Greiner). As a control the bacteria were also incubated in PBS with either 50% plasma or 50% urine without peptide. The plate was incubated for 2 hours at 37° C. and 200 rpm. After incubation the number of viable bacteria was determined microbiologically by plating the samples and a 10-times dilution series in PBS on diagnostic sensitivity test agar plates (DST; Sigma). The DST plates were incubated overnight at 37° C. Results were expressed as lethal concentration 99.9, or LC99.9, which represents the lowest concentration of peptide that killed 99.9% of the bacteria within 2 hours of incubation.

Hemolysis Assay

Whole blood was collected (from healthy volunteers) in citrate tubes and centrifuged for 10 minutes at 3000 rpm. The pellet containing the erythrocytes was washed in PBS three times for 10 minutes at 1000 rpm. From the pellet a 20% erythrocyte suspension was made in PBS. The 20% erythrocyte suspension was diluted 10 times to form a 2% (v/v) erythrocyte suspension. In a polypropylene V-bottom plate 50 µl of human plasma were added to 25 µl of peptide solutions with final concentrations ranging from 12.8 µM to 204.8 µM in triplicate. Next, 25 µl of the 2% erythrocyte solution were added to the wells containing peptide and plasma. As a negative control wells containing 25 µl of PBS instead of peptide were included. As a positive control wells with 25 µl of 5% (v/v) TRITON®-X (Sigma-Aldrich) were included. The plate was sealed off with sealing tape (Costar) and the suspensions mixed by shaking for 10 seconds at 300 rpm. Thereafter, the plate was incubated for 1 hour at 37° C. For analysis, the plate was centrifuged for 5 minutes at 2000 rpm. From the supernatant 75 µl were transferred to a polystyrene 96-well flat-bottom plate and the absorbance at 415 nm was assessed. Results were expressed as the highest concentration that resulted in <5% erythrocyte lysis.

Resistance Development Assay

A bacterial culture was prepared and washed as described before. The bacterial culture was diluted to a concentration of $5 \times 10^6$ CFU/ml in modified RPMI 1640 comprising 20 mM HEPES, L-glutamine and without sodium bicarbonate (RPMImod; Sigma-Aldrich). In a polypropylene 96-well plate, a two-fold peptide dilution series was made in RPMImod with concentrations ranging from 0.94 µM to 240 µM. An antibiotic dilution series of ciprofloxacin and rifampicin (Sigma-Aldrich) was added with concentrations ranging from 0.25 µg/ml to 500 µg/ml in RPMImod. A negative control of RPMImod without peptide or an antibiotic was included for both dilution series. A contamination control was included containing only RPMImod. To all the wells, except the contamination control wells, 5 µl of the bacterial suspension were added. The plate was sealed and incubated overnight at 37° C. and 200 rpm. After incubation the MIC was determined as the well with the lowest peptide concentration and no bacterial growth. The well with half the MIC was diluted 2.5-fold with RPMImod and transferred to an Eppendorf tube. For the next passage the peptide and antibiotic series were prepared as described before and 5 µl of the half MIC were added. The results were expressed as the fold increase of the MIC compared to the MIC at the first passage.

Biofilm Breakdown Assay

To a polypropylene 96-well flat-bottom plate (Greiner) 50 µl of a bacterial suspension at a concentration of $1\times10^7$ CFU/ml in BM2 medium (Overhage et al., 2008) were added. A control comprising BM2 medium alone was included. The plate was sealed off with a seal (Costar) and incubated in a humidified environment for 24 hours at 37° C. Thereafter the wells were washed 2 times with PBS. Next, the wells were exposed to 100 µl of peptide solution ranging from final concentrations of 0.8 µM to 102.4 and a control without peptide was included. The plate was sealed off and incubated for 2 hours at 37° C. and 200 rpm. For analysis the plate was sonicated (Ultrasoonbad BRANSONIC® m1800H-E; Boom b.v.) for 5 minutes to detach the biofilm bacteria. The number of viable bacteria in the sonicates was determined microbiologically by plating the samples and a 10-times dilution series on DST agar plates and incubating these overnight at 37° C. Results were expressed as the LC99.9.

Biofilm Prevention Assay

In a polypropylene 96-well flat-bottom plate 50 µl of peptide solution in BM2 medium was added to achieve final concentrations ranging from 0.8 µM to 25.6 µM in sixplicate. From a bacterial suspension with a concentration of $1\times10^7$ CFU/ml in BM2 medium 50 µl was added to the wells with peptide. As an untreated control the bacteria were added to BM2 medium without peptide. As a contamination control BM2 medium alone was included. The plate was sealed off and incubated for 24 hours at 37° C. in a humidified environment. After incubation the wells were washed four times with PBS. Next, the biofilm bacteria were stained with 1% crystal violet (Sigma-Aldrich) for 10 minutes at room temperature. The excess crystal violet was washed away with PBS four times. Subsequently, 96% ethanol was added to the wells and incubated for 10 minutes at room temperature. The supernatant was transferred to a polystyrene 96-well flat-bottom plate and the absorbance at 595 nm measured. Results were expressed as arbitrary units (au), i.e., biofilm mass, as measured after crystal violet staining.

Ex Vivo Skin Model

The donor skin was transported to the LUMC in RPMI 1640 medium (Gibco) supplemented with penicillin/streptomycin (Gibco). Skin samples were washed in PBS and left overnight in RPMI 1640 medium without antibiotics. On the day of the experiment the skin was again washed in PBS, then spread out and punches with a diameter of 8 mm diameter were made with a biopsy punch (Stiefel). The skin samples were dried with a cotton swab. A liquid dam was made with LC Block-Out Resin (Ultradent) on the edge of the skin samples to prevent liquids from dripping off. The liquid dam was solidified by 4 seconds exposure of UV light (Super 1200 led; ECO). The skin samples were placed on grids in a 12-well plate (Costar) filled underneath with medium comprising Ham F12, DMEM and FCS (Gibco). An S. aureus LUH 14616 bacterial suspension was cultured and washed as described before. The skin punches were inoculated with 5 µl of the bacterial suspension ($1\times10^8$ CFU/ml) for one hour at 37° C. and 5% $CO_2$. Peptide concentrations ranging from 2.5 µM-204.8 µM were made in PBS. The infected skin was treated for 1 hour at 37° C. and 5% $CO_2$ with 10 µl of the peptide solutions, including a control with 10 µl of PBS alone. Polypropylene tubes were filed with glass beads (1.7 mm diameter) and 1 ml of PBS. The liquid dam was removed from the skin after treatment. The skin was transferred to the tubes with beads and beated two times for 20 seconds in the MINILYS® bead beater (Bertin Technologies), the samples were placed on ice between the beatings. The beated samples were diluted in a 2-times dilution series and plated on a DST agar plate. The DST plates were incubated overnight at 37° C. Results were expressed as the number of viable bacteria (CFU/ml) after treatment.

Neutrophil Migration Assay

Heparinized blood was collected from healthy human volunteers. Next, 10 ml of blood were mixed to 15 ml of PBS in a tube. Underneath the diluted blood, 10 ml of Ficoll (Pharmacy, LUMC) were added. The tube was spun at 1800 rpm for 20 minutes without brake. The supernatant was removed and 40 ml of erythrocyte lysis buffer (0.1 mM EDTA, 0.18 M NH4Cl, 10 mM KHCO3) were added to the pellet. This mixture was incubated at room temperature until erythrocyte lysis was evident. The tube was centrifuged at 1200 rpm for 10 minutes, the supernatant was discarded. The pellet was washed again with PBS the same way. The pellet was resuspended in RPMI 1640 medium and the cells were counted with a counting chamber. The cells were diluted to $2\times10^6$ cells/ml of RPMI 1640. The inserts with a 3.0 µm pore size in a 12-well plate (HTS transwell; Costar) were blocked with 400 µl of PBS with 0.1% w/v BSA for 10 minutes at room temperature after which the BSA solution was discarded. The $2\times10^6$ cells/ml suspension was diluted with RPMI to add 400 µl of a $2\times10^5$ cells/ml suspension to the inserts. Peptide solutions with concentrations ranging from 3.2 µM to 12.8 µM were made in RPMI 1640 as chemoattractant. In the lower compartment 1 ml of the chemoattractant was added. A positive control 10 nM fMLP (Sigma-Aldrich) in RPMI supplemented with 10% v/v heat inactivated fetal calf serum (FCSi; Gibco) and as a negative control 1 ml of RPMI were used. The plate was incubated for 90 minutes at 37° C. and 5% $CO_2$. After incubation 50 µl of 50 mM EDTA (Sigma) were added to the lower compartment. The cells that had migrated to the lower compartment were transferred to a FACS tube and enumerated on the Accuri flowcytometer C6 (BD). Results were expressed as the percentage of migrated neutrophils compared to the positive FMLP control, and corrected for the negative control.

LPS Neutralization by Peptides

Heparinized blood collected from healthy human volunteers was diluted five times in RPMI 1640. Next, 195 µl of diluted blood were pipetted in to the wells of a 96-well cell culture plate. In another 96-well polypropylene V-bottom plate, 15 µl of peptide solution with final concentrations of 1 nM to 1000 nM were mixed with 15 µl of 500 ng/ml lipopolysaccharide from E. coli J5 (LPS; Sigma) for 30 minutes at 37° C. and 200 rpm. After incubation the mixtures were diluted five times with 120 µl of RPMI. From the diluted mixtures 5 µl were transferred to the wells of the plate containing the 195 µl of blood. The plate was incubated for 20 hours at 37° C. and 5% $CO_2$. The plate was centrifuged for 5 minutes at 1200 rpm. The supernatants were stored as aliquots at −20° C. until analysis of the cytokine level by ELISA. The IL-12p40 sandwich ELISA from Invitrogen was used. ELISAs were performed according to manufacturer's instructions. Results were expressed as the concentration IL-12p40 in pg/ml.

Selective Killing of Melanoma Cells by Peptides

Normal melanocytes (up to 4 passages) and 4 melanoma cell lines (mel 11.11, mel 12.13, mel 05.18, mel 09.03) were cultured overnight 37° C. at a concentration of $2 \times 10^4$ cells/well in 100 μl of DMEM supplemented with 7.5% (v/v) fetal calf serum in a humidified 5% $CO_2$ atmosphere. The next day 75 μl of medium were removed and then 25 μl of double concentrated peptide (SP4 and SP27) solutions prepared in DMEM supplemented with 0.5% human serum were added. After an incubation for 4 hours in a humidified 5% $CO_2$ atmosphere at 37° C. the supernatant was removed for measurement of the LDH release using the Roche kit. The background LDH release by the cells, determined by exposing the cells to DMEM with 0.5% serum without peptide, was subtracted from the values for the peptide-exposed cells. Finally, the results ae expressed as the percentage LDH release using the values found for triton-exposed cells as 100%.

Statistical Analysis

The comparison of two samples was first made with a Kruskal-Wallis analysis. Next, a Mann-Whitney U test was used. The Samples were considered statistically significant for $P<0.05$.

Results

Screening of Snake Peptides for Bactericidal Activity and Toxic Effect

To select candidates for development as a novel agent for treatment for infections caused by multi-drug resistant (MDR) bacteria, 35 synthetic snake peptides were screened for their bactericidal activity on a MDR *S. aureus* and a MDR *P. aeruginosa* strain in 50% v/v human plasma. The experiment (Table 1) revealed that the peptides may be categorized into three groups. Group I comprises 7 of 35 peptides with a LC99.9 of ≤6.4 μM for both MRSA and *P. aeruginosa*; Group II comprises 19 out of 35 peptides with a LC99.9>6.4 μM for MRSA and ≤12.8 μM for *P. aeruginosa*; Group III comprises 9 out of 35 peptides with a LC99.9≥102.4 μM for MRSA and >12.8 μM for *P. aeruginosa*.

Most peptides were more effective against the MDR *P. aeruginosa* strain than the MDR *S. aureus* strain. The LC99.9 for the peptides against MDR *S. aureus* differed among the panel of snake peptides ranging from 3.2 μM (SP4) to more than 102.4 μM (multiple peptides). Interestingly, the LC99.9 for the peptides against MDR *P. aeruginosa* ranged from as low as 0.2 μM (SP23) to concentrations higher than 102.4 μM (multiple peptides).

The snake peptides killed the bacteria in a dose-dependent manner. For example, SP4 requires a submicromolar concentration of 0.4 μM to kill 99.9% of the *P. aeruginosa* bacteria (FIG. 1, Panel A) and 3.2 μM for *S. aureus* (FIG. 1, Panel B). SP27 needs slightly higher concentrations, i.e., 0.8 μM for *P. aeruginosa* and 6.4 μM for *S. aureus* (FIG. 1, Panels C and D).

To determine its active domain, shorter versions of SP4 were synthesized and tested for bactericidal activity. Results indicated that a couple shorter versions were equally effective as SP4 (Table 2).

The snake peptides were also tested for their toxic effect on human erythrocytes. All snake peptides displayed low toxicity against human erythrocytes, for 23 out of 35 peptides a concentration of 204.8 μM resulted in less than 5% lysis of the erythrocytes (Table 1). Snake peptides 4 and 27 showed promising results in their bactericidal activity and their toxicity and, therefore, are selected for further testing.

Resistance Development Against SP4 and SP27

Next, the ability of SP4 and SP27 to select for resistance in *S. aureus* LUH 14616, *A. baumannii* and *E. coli* was assessed. The MIC for both SP4 and SP27 remained constant for all 20 passages, whereas the MIC for imipenem and rifampicin started to increase after already a couple of passages. Together, the fold increase for SP4 and SP27 was considerable less than for the antibiotics.

Effect of Snake Peptides 4 and 27 on MDR Strains of the ESKAPE and Colistin-Resistant *E. coli*

Thereafter, it was determined that the activity of the two most promising peptides, i.e., SP4 and SP27, against multidrug resistant strains of the ESKAPE panel and an *E. coli* resistant for colistin, a last resort antibiotic. The results showed that SP4 and SP27 are extremely effective (submicromolar concentrations) against MDR *K. pneumoniae, A. baumannii, P. aeruginosa, E. cloacae* and *E. coli* in PBS with 50% plasma (FIG. 3). For *E. faecium* and *S. aureus* low micromolar concentrations of SP4 and SP27 were sufficient to kill 99.9% of the bacteria. Determination of the ability of these snake peptides to kill *E. coli* in 50% v/v urine revealed a LC99.9 of 0.8 μM with a range of 0.8-1.6 μM for both peptides. Together, SP27 requires a slightly higher concentration than SP4 to kill the different species, except for the MDR *E. cloacae* and *E. coli* strains.

Biofilm Breakdown by SP4 and SP27

Next, the ability of SP4 and SP27 to degrade an established biofilm was determined. The results revealed that SP4 and SP27 dose-dependently degraded a 24 hours biofilm of *A. baumannii* with complete elimination of the biofilms seen at 51.2 μM peptide (FIG. 4, Panels A and B). MRSA biofilms were not efficiently degraded by SP4 at concentrations up to 102.4 μM (FIG. 4, Panel C).

Prevention of Biofilm Formation by SP4 and SP27

As *A. baumannii* biofilms were effectively degraded by SP4 and SP27, the ability of these peptides to prevent the formation of biofilms was then determined. The results revealed that SP4 and SP27 both completely prevented the biofilm formation of *A. baumannii* at ≥6.4 μM peptide (FIG. 5). As a control, the ability of these peptides to kill *A. baumannii* in BM2 medium was assessed. The results revealed that SP4 and SP27 eliminate all bacteria at concentrations of 1.6 μM peptide and higher and with 0.8 μM peptide reduce the amount of viable bacteria with 2 log, indicating that the bacteria may still kill the bacteria in the BM2 medium.

Elimination of *S. aureus* from Ex Vivo Human Skin by SP4 and SP27

Figure 6:
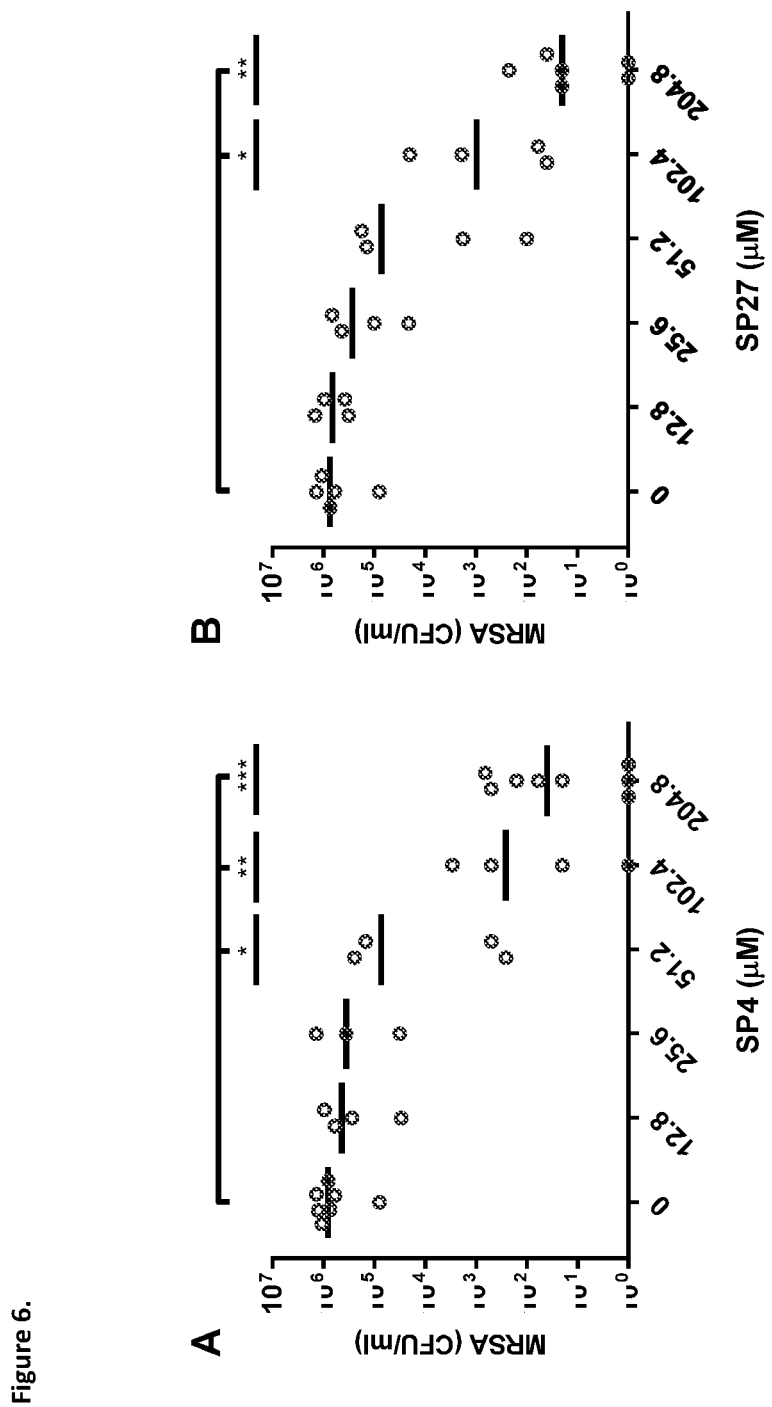
FIG. 6: Elimination of an MRSA infection on ex vivo human skin by SP4 and SP27. Ex vivo skin inoculated with MRSA treated for 1 hour with increasing concentrations SP4 (Panel A) and SP27 (Panel B). Significance compared to control (0 μM) was calculated with the Mann-Whitney U test (*P<0.05, P<0.01 and *P<0.001).

The ability of SP4 and SP27 to eliminate MRSA from ex vivo human skin was assessed. The results revealed that 10 μl of 102.4 μM SP4 was able to kill 99.9% of the MRSA (FIG. 6, Panel A). SP927 was slightly less effective in eliminating MRSA from the skin, with 99.9% elimination at 204.8 μM (FIG. 6, Panel B).

Effect of SP4 and SP27 on Neutrophil Migration

Figure 7:
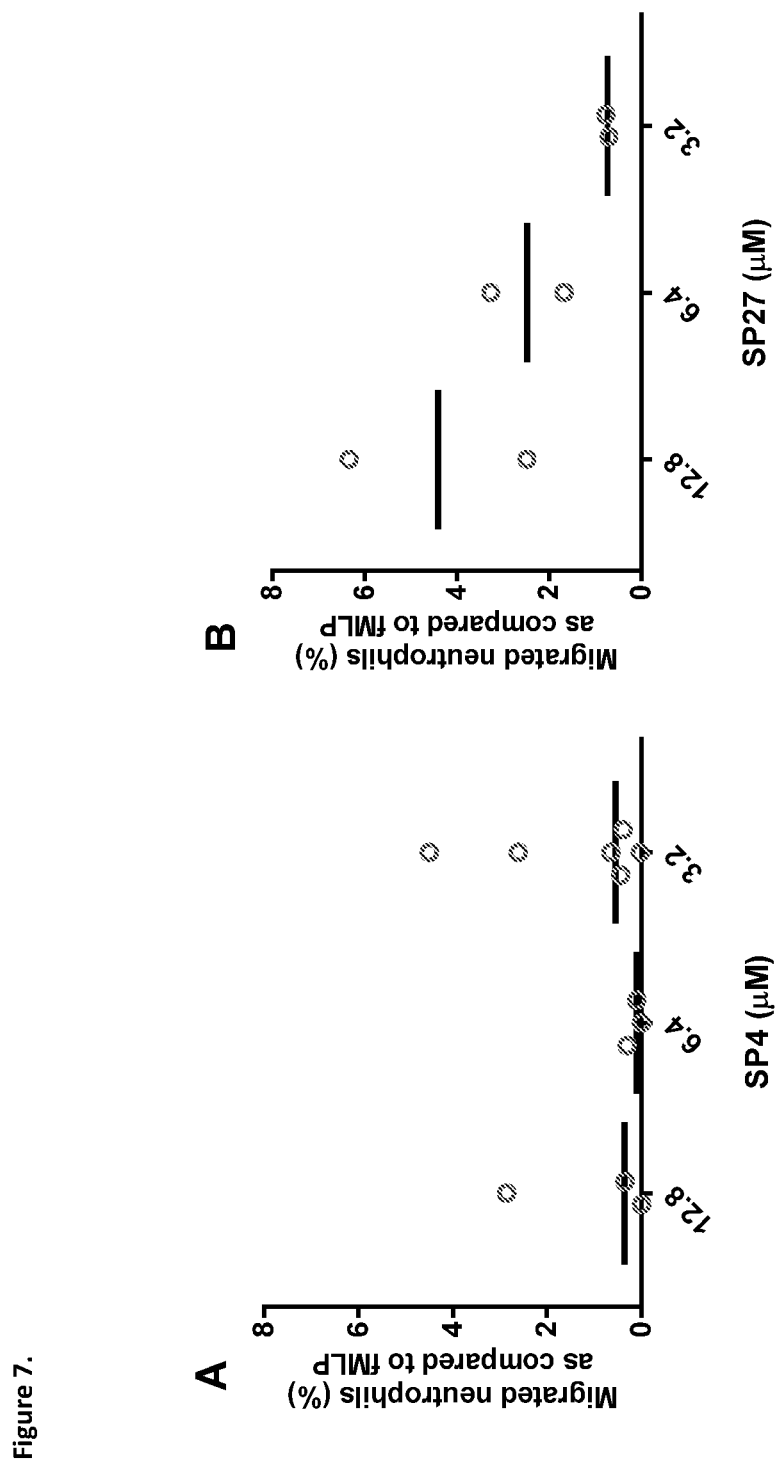
FIG. 7: Chemotactic effect of SP4 and SP27 on human neutrophils. Increasing concentrations of SP4 (Panel A) and SP27 (Panel B) were used as a chemoattractant to attract neutrophils from the upper compartment through an insert to the lower compartment during 90 minutes. Results are expressed as the percentage of migrated neutrophils compared to fMLP, the positive control (100%) and corrected for background migration (the negative control).

To obtain some information on the immunomodulatory abilities of the snake peptides, the chemotactic effects of SP4 and SP27 on human neutrophils were assessed. Results revealed that SP4 is poorly chemotactic at concentrations up to 12.8 μM (causes less than 1% of the neutrophils to migrate), compared to the positive control peptide fMLP (FIG. 7, Panel A). SP27 attracts the neutrophils in a dose-response, with 4.4% migrated neutrophils at 12.8 μM of peptide (FIG. 7, Panel B). LL-37 induces 5.6% of the neutrophils to migrate at a concentration of 3.2 μM peptide.

So SP4 has little effect as chemo-attractant, while for SP27 the amount of migrated neutrophils increases with the concentration peptide.

LPS Neutralizing Ability of SP4

Figure 8:
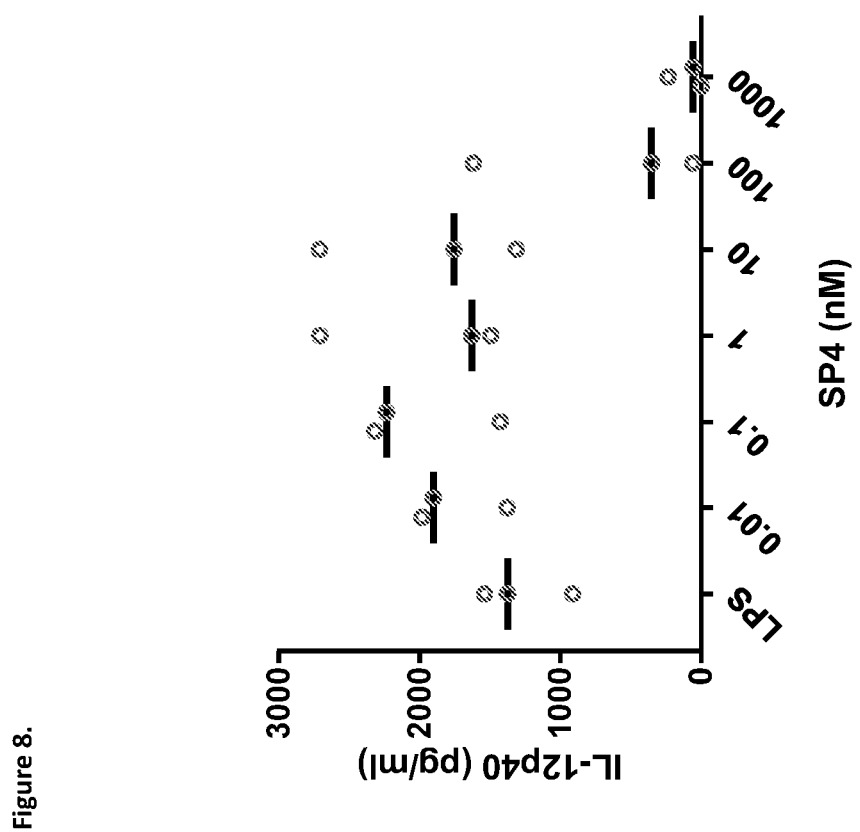
FIG. 8: LPS neutralization by SP4. In short, whole blood was incubated with 500 ng/ml LPS that had been pre-treated with increasing concentrations of SP4. After incubation for 20 hours, the concentration IL-12p40 in the supernatant was measured with an ELISA.

To obtain some information on the inflammatory process, the ability of SP4 to neutralize LPS using the whole blood assay and IL-12p40 production as read-out was measured. The results (FIG. 8) indicate that at a concentration of 100 nM SP4 neutralizes LPS by 74%, and at 1000 nM SP4 almost completely (96%) as compared to the LPS control.

Selective Killing of Cancer Cells by SP4 and SP27

To obtain some data on the selective carcinoma toxic activity of the snake-derived peptides, it was determined that the cytotoxic effects of increasing does of SP4 and SP27 on normal human melanocytes and 4 melanoma cell lines using the LDH release assay. The results indicate that at a dose of 51.2 µM SP4 and SP27 did not affect the viability of normal melanocytes, but exerted a significant toxic effect on the melanoma cells.

CONCLUSION

The threat of infections that cannot be effectively treated with antibiotics and the associated need for novel agents to combat such infections are widely acknowledged. For the development of such novel agents, two candidates were selected from a panel of 35 synthetic snake cathelicidins based on the following findings. First, the selected snake peptides (SP) 4 and 27 are highly efficient in killing a multidrug resistant (MDR) S. aureus and a MDR P. aeruginosa strain in vitro without being toxic to human erythrocytes. The selectivity index, i.e., the ratio between the highest non-toxic concentration of the peptide and the lowest concentration of the peptide resulting in 99.9% reduction of an inoculum of about 1 million bacteria (the lethal concentration 99.9 or LC99.9), amounted to 64 and 512 for SP4 and to 16 and 128 for SP27 for MDR S. aureus and P. aeruginosa, respectively. This data indicates an excellent therapeutic window. Second, in biologically relevant in vitro conditions, i.e., 50% v/v human plasma or urine, these snake peptides were highly effective against MDR strains of the ESKAPE panel and colistin resistant E. coli. Third, SP4 and SP27 induced limited resistance in S. aureus compared to the antibiotics ciprofloxacin and rifampicin.

As the biofilm is the main life-stage of many (MDR) bacteria and the majority of clinical infections are biofilm-associated infections, the preliminary observations made that a 2-hour exposure to SP4 and SP27 is effective in degrading MDR A. baumannii biofilms, but less effective against MRSA biofilms, are of clinical relevance. As SP4 and SP27 are effective in killing bacteria in BM2 medium, the finding that these peptides prevent biofilm formation may be attributed to the killing of the bacteria before they may form a biofilm. Another important aspect of the successful treatment of biofilms concerns activity against persisters, i.e., bacterial cells in a dormant state with a high tolerance to antibiotics. It was revealed that SP4 is highly effective against persisters originating from matured, antibiotic-exposed, MRSA biofilms. Furthermore, it was have found that SP4 in vitro may neutralize the bacterial endotoxin lipopolysaccharide (LPS), indicating that this peptide may affect the inflammatory reaction at the site of infection.

Most of the snake peptides were more effective against MDR P. aeruginosa than against MDR S. aureus. In agreement, the gram-negative bacteria within the ESKAPE panel were more susceptible to SP4 and SP27 than the gram-positive bacteria, confirming that snake peptides display selective efficacy to (MDR) gram negative bacteria. Of note, SP18 was not effective against S. aureus (LC99.9>102.4 while being highly effective against MDR P. aeruginosa (LC99.9 of 0.8 Unfortunately, an explanation for this difference in susceptibility to snake peptides between gram-negative and gram-positive bacteria cannot be provided. As cathelicidins with their positively charged face interact with negatively charged plasma membrane constituents differences in the plasma membrane and other cell wall components of gram-negative and gram-positive bacteria may play an important role. Biophysical experiments with artificial bacterial membranes and molecular dynamics may be instrumental in understanding why snake peptides selective affect gram-negative bacteria. Interestingly, gram-negative rods are overrepresented in the oral flora of (non-poisonous) snakes (Shek et al., 2009). Thus, it may be speculated that snakes produce peptides that are highly effective against the gram-negative bacteria to control bacterial growth in the oral cavities. Anyhow, the selectivity of the snake peptides may be advantageous for the treatment of infections with gram negative bacteria not responding to current antibiotics.

Several peptides in the snake peptide panel have been reported earlier by others. CATHPb1 and CATHPb3 found in Phyton bivittatus are identical to SP15 and SP16 (Cai et al., 2018). Comparison of the activities of SP15 and CATHPb1 revealed that they were significantly less effective against MRSA than against P. aeruginosa, while SP16 and CATPb3 both exerted no bactericidal effect against MRSA and P. aeruginosa. Whereas SP15 and SP16 showed no toxicity against erythrocytes (still safe around 800 µg/ml), CATHPb1 and CATHPb3 showed 6.63% and 9.14% hemolysis at 100 µg/ml, respectively. This difference in hemolytic activity may be attributed to the presence of 50% v/v human plasma in the experiments disclosed herein as opposed to PBS alone. Another peptide, i.e., SP13, is similar to OH-CATH30, a peptide from the king cobra only four amino acids shorter than SP13 (Zhao et al., 2018). SP13 shows a slightly higher bactericidal activity than OH-CATH30 against MRSA, i.e., an LC99.9 of 24.5 mg/ml (5.9 µM) for SP13 compared to a MIC90 of 32 mg/ml for OH-CATH30. The latter peptide seems to be more toxic than SP13 (70% hemolysis at 250 µg/ml for OH-CATH30 and <5% at 851 µg/ml for SP4). It would be interesting to see if this difference is related to the additional four amino acids in OH-CATH30. Furthermore, similar data on the bactericidal activity of SP2 (identical to crotalicidin) and SP3 (identical to bathroxicidin) have been reported by others (Falcao C. B. et al., 2014). Surprisingly, these authors reported the sequence of SP4 (identical to lutztcidin) and SP9 (identical to lachesicidin) without any functional activities.

The finding that snake peptides displayed low toxicity against human erythrocytes indicates that they may be considered for systemic application. Another important finding pertains to the ability of SP4 and SP27 to eliminate MRSA from ex vivo human skin. Preliminary experiments revealed that already, within a 1-hour exposure, these peptides eliminated the bacteria from intact human skin in a dose-dependent fashion with SP4 being slightly more effective than SP27.

Experiments will be performed to confirm the effects of the peptides disclosed herein on wounded ex vivo skin models colonized by gram-positive and gram-negative bacteria as well as wounded ex vivo human skin with a biofilm. Furthermore, multiple exposure durations will be performed. These models are useful to determine the effects of the peptides on the wound healing process. The peptides will be tested as an ointment for topical application on wounds.

Finally, Wang et al. have reported that the snake cathelicidin BF30 (identical to SP5) inhibits melanoma cells and other cancer cells in vitro and reduces the tumor load in melanoma-bearing mice. In this connection, it was found that SP4 and SP27 is toxic to melanoma cells at concentrations that are safe for primary human melanocytes, indicating that these peptides may be candidates for the treatment of melanomas and other cancers.

TABLE 1

Figure 10:
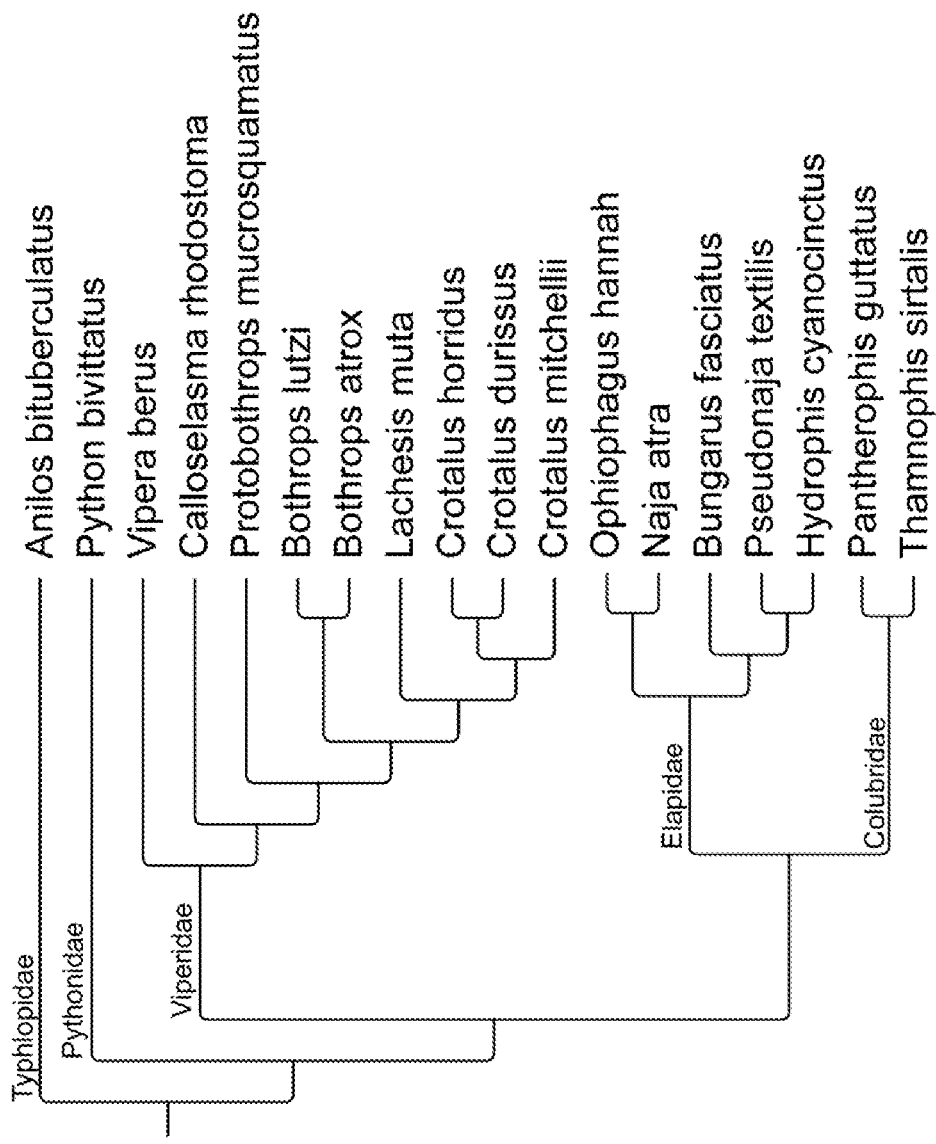
FIG. 10: Phylogenetic tree of the snake species described in examples.

Bactericidal effect on MDR *S. aureus* and *P. aeruginosa* and cytotoxic effect of snake peptides. The bactericidal activity of the snake peptides on MDR *S. aureus* (LUH 14616) and MDR *P. aeruginosa* (LUH 15103) was determined after a 2-hour treatment in the presence of 50% v/v human plasma. Bactericidal activity is expressed as the LC99.9, i.e., the lowest concentration of peptide that kills ≥99.9% of the bacteria. Results are medians (and range) of three to thirteen independent experiments, each in duplicate. If no range is shown the LC99.9 did not differ between the experiments or the peptide is tested once. Toxic effect of the peptides was assessed by exposing human erythrocytes to increasing peptide concentrations for 1 hour in the presence of human plasma. Results are expressed as the highest peptide concentration that resulted in <5% erythrocyte lysis as compared to the positive control triton-X. Snake species sorted by phylogenetic tree (FIG. 10).

| Species | Peptide | Alternative name in literature | LC99.9 (µM) MRSA in 50% plasma | LC99.9 (µM) MDR *P. aeruginosa* in 50% plasma | Hemolysis (µM) in 50% plasma |
|---|---|---|---|---|---|
| *Anilos bituberculatus* | SP27 | | 6.4 (3.2-6.4) | 0.8 (0.2-1.6) | 102.4 |
| *Python bivittatus* | SP15 | CATHPb1 | 12.8 | 0.8 | 204.8 |
| | SP16 | CATHPb3 | >102.4 | >102.4 | 204.8 |
| *Calloselasma rhodostoma* | SP14 | | 12.8 | 0.4 | 204.8 |
| | SP21 | | >102.4 | >102.4 | 204.8 |
| *Protobothrops mucrosquamatus* | SP23 | | 4.8 (3.2-6.4) | 0.2 | 204.8 |
| | SP33 | | >102.4 | >102.4 | 204.8 |
| *Bothrops lutzi* | SP4 | Lutzicidin | 3.2 (3.2-12.8) | 0.4 (0.2-16) | 204.8 |
| *Bothrops atrox* | SP3 | Batroxicidin | 3.2 | 0.8 | 204.8 |
| *Lachesis muta* | SP9 | Lachesicidin | 51.2 (25.6-51.2) | 1.6 | 204.8 |
| *Crotalus horridus* | SP34 | | >102.4 | >102.4 | 204.8 |
| *Crotalus durissus* | SP2 | Crotalicidin | 25.6 | 0.4 | 204.8 |
| | SP6 | | 57.6 (12.8-102.4) | 0.4 | 204.8 |
| | SP7 | | 38.4 (25.6-51.2) | 0.8 | 204.8 |
| *Crotalus mitchellii* | SP25 | | 12.8 | 0.4 | 102.4 |
| | SP26 | | >102.4 | 12.8 | 102.4 |
| *Ophiophagus hannah* | SP1 | | >102.4 | 3.2 | 51.2 |
| | SP13 | OH-CATH | 5.9 (1.6-12.8) | 0.4 | 204.8 |
| | SP17 | | >102.4 | >102.4 | 51.2 |
| | SP18 | | 102.4 | 0.8 | 204.8 |
| | SP19 | | >102.4 | 12.8 | 204.8 |
| | SP20 | | >102.4 | >102.4 | 204.8 |
| *Naja atra* | SP10 | | 16 (6.4-15.6) | 0.8 | 204.8 |
| *Bungarus fasciatus* | SP5 | Bf-CRAMP/BF-30 | 25.6 | 0.4 | 204.8 |
| *Pseudonaja textillis* | SP11 | | 3.2 | 0.4 | 204.8 |
| | SP12 | | 25.6 (12.8->102.4) | 3.2 | 51.2 |
| *Hydrophis cyanocinctus* | SP8 | | 25.6 | 1.6 | 102.4 |
| *Pantherophis guttatus* | SP28 | | 51.2 | 6.4 | 204.8 |
| | SP29 | | >102.4 | 51.2 | 102.4 |
| | SP30 | | 51.2 | 2.4 (1.6-3.2) | 204.8 |
| | SP35 | | 51.2 | 1.6 | 204.8 |
| *Thamnophis sirtalis* | SP22 | | 102.4 | 51.2 | 102.4 |
| | SP24 | | 6.4 | 1.6 | 102.4 |
| | SP31 | | 102.4 | 25.6 | 102.4 |
| | SP32 | | 25.6 | 12.8 | 102.4 |

TABLE 2

Bactericidal effect on MDR *S. aureus* by shortened versions of SP4. The peptide SP4 and its shortened versions from either the N-terminus or C-terminus were screened for bactericidal activity against MDR *S. aureus* in 50% v/v humane plasma. The results are expressed as the concentration that induced a 3 log reduction of viable bacteria compared to the control (0 μM).

| Peptide | Number of amino acids shortened at N terminus | Number of amino acids shortened at C terminus | LC99.9 (μM) |
|---|---|---|---|
| SP4 | 0 | 0 | 3.2 |
| SP4-1 | 0 | 1 | 3.2 |
| SP4-2 | 1 | 0 | 3.2 |
| SP4-3 | 0 | 2 | 3.2 |
| SP4-4 | 1 | 1 | 3.2 |
| SP4-5 | 2 | 0 | 6.4 |
| SP4-6 | 0 | 3 | 32 |
| SP4-7 | 1 | 2 | 4.8 |
| SP4-8 | 2 | 1 | 12.8 |
| SP4-9 | 3 | 0 | 25.6 |
| SP4-10 | 0 | 4 | 12.8 |
| SP4-11 | 1 | 3 | 38.4 |
| SP4-12 | 2 | 2 | 51.2 |
| SP4-13 | 3 | 1 | 76.8 |
| SP4-14 | 4 | 0 | 51.2 |
| SP4-15 | 0 | 5 | 102.4 |
| SP4-16 | 1 | 4 | 64 |
| SP4-17 | 2 | 3 | 51.2 |
| SP4-18 | 3 | 2 | 19.2 |
| SP4-19 | 4 | 1 | 38.4 |
| SP4-20 | 5 | 0 | 6.4 |
| SP4-21 | 0 | 6 | 12.8 |
| SP4-22 | 1 | 5 | 38.4 |
| SP4-23 | 2 | 4 | 19.2 |
| SP4-24 | 3 | 3 | >102.4 |
| SP4-25 | 4 | 2 | 38.4 |
| SP4-26 | 5 | 1 | 76.8 |
| SP4-27 | 6 | 0 | 38.4 |
| SP4-28 | 0 | 7 | 25.6 |
| SP4-29 | 1 | 6 | 12.8 |
| SP4-30 | 2 | 5 | 64 |
| SP4-31 | 3 | 4 | 102.4 |
| SP4-32 | 4 | 3 | 76.8 |
| SP4-33 | 5 | 2 | 19.2 |
| SP4-34 | 6 | 1 | 51.2 |
| SP4-35 | 7 | 0 | 32 |
| SP4-36 | 0 | 8 | 9.6 |
| SP4-37 | 1 | 7 | 12.8 |
| SP4-38 | 2 | 6 | 12.8 |
| SP4-39 | 3 | 5 | 76.8 |
| SP4-40 | 4 | 4 | >102.4 |
| SP4-41 | 5 | 3 | >102.4 |
| SP4-42 | 6 | 2 | >102.4 |
| SP4-43 | 7 | 1 | >102.4 |
| SP4-44 | 8 | 0 | 51.2 |
| SP4-45 | 0 | 9 | 19.2 |
| SP4-46 | 1 | 8 | 28.8 |
| SP4-47 | 2 | 7 | 19.2 |
| SP4-48 | 3 | 6 | 102.4 |
| SP4-49 | 4 | 5 | >102.4 |
| SP4-50 | 5 | 4 | >102.4 |
| SP4-51 | 6 | 3 | >102.4 |
| SP4-52 | 7 | 2 | >102.4 |
| SP4-53 | 8 | 1 | >102.4 |
| SP4-54 | 9 | 0 | 102.4 |
| SP4-55 | 0 | 10 | 19.2 |
| SP4-56 | 1 | 9 | 19.2 |
| SP4-57 | 2 | 8 | 25.6 |
| SP4-58 | 3 | 7 | 51.2 |
| SP4-59 | 4 | 6 | 38.4 |
| SP4-60 | 5 | 5 | 51.2 |
| SP4-61 | 6 | 4 | >102.4 |
| SP4-62 | 7 | 3 | >102.4 |
| SP4-63 | 8 | 2 | 102.4 |
| SP4-64 | 9 | 1 | >102.4 |
| SP4-65 | 10 | 0 | >102.4 |

Example 2—Alanine Scan

The amino acids of the SP27 peptide were substituted at various positions with Alanine. The substituted peptides were tested on *A. baumannii* and *E. coli* bacterial strains for having antimicrobial activity. Furthermore, the substituted peptides were tested for their hemolytic activity as an indicator for their toxicity.

TABLE 3

Alanine scan

LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. A. baumannii is the multidrug resistant strain Acinetobacter baumannii RUH875; E. coli is the drug-sensitive strain Escherichia coli LUH5108. Substituted alanines are underlined.

| Peptide | LC99.9 (uM) A. baumannii | LC99.9 (uM) E. coli | Toxicity (µM) | Sequence |
|---|---|---|---|---|
| SP27    | 0.8 | 1.6 | 102.4  | K R F K K F F R K V K K G V H R Y F K K N K F Y I A A T I P Y Y G |
| SP27-1  | 1.6 | 1.6 | 102.4  | A̲ R F K K F F R K V K K G V H R Y F K K N K F Y I A A T I P Y Y G |
| SP27-2  | 0.8 | 1.6 | 102.4  | K A̲ F K K F F R K V K K G V H R Y F K K N K F Y I A A T I P Y Y G |
| SP27-3  | 0.8 | 1.6 | ≥204.8 | K R A̲ K K F F R K V K K G V H R Y F K K N K F Y I A A T I P Y Y G |
| SP27-4  | 1.6 | 1.6 | ≥204.8 | K R F A̲ K F F R K V K K G V H R Y F K K N K F Y I A A T I P Y Y G |
| SP27-5  | 1.6 | 3.2 | 102.4  | K R F K A̲ F F R K V K K G V H R Y F K K N K F Y I A A T I P Y Y G |
| SP27-6  | 0.4 | 1.6 | ≥204.8 | K R F K K A̲ F R K V K K G V H R Y F K K N K F Y I A A T I P Y Y G |
| SP27-7  | 0.4 | 1.6 | ≥204.8 | K R F K K F A̲ R K V K K G V H R Y F K K N K F Y I A A T I P Y Y G |
| SP27-8  | 0.8 | 1.6 | 102.4  | K R F K K F F A̲ K V K K G V H R Y F K K N K F Y I A A T I P Y Y G |
| SP27-9  | 1.6 | 1.6 | ≥204.8 | K R F K K F F R A̲ V K K G V H R Y F K K N K F Y I A A T I P Y Y G |
| SP27-10 | 0.4 | 1.6 | ≥204.8 | K R F K K F F R K A̲ K K G V H R Y F K K N K F Y I A A T I P Y Y G |
| SP27-11 | 1.6 | 1.6 | 102.4  | K R F K K F F R K V A̲ K G V H R Y F K K N K F Y I A A T I P Y Y G |
| SP27-12 | 0.8 | 1.6 | 102.4  | K R F K K F F R K V K A̲ G V H R Y F K K N K F Y I A A T I P Y Y G |
| SP27-13 | 1.6 | 3.2 | ≥204.8 | K R F K K F F R K V K K A̲ V H R Y F K K N K F Y I A A T I P Y Y G |
| SP27-14 | 0.8 | 1.6 | ≥204.8 | K R F K K F F R K V K K G A̲ H R Y F K K N K F Y I A A T I P Y Y G |
| SP27-15 | 3.2 | 3.2 | ≥204.8 | K R F K K F F R K V K K G V A̲ R Y F K K N K F Y I A A T I P Y Y G |
| SP27-16 | 0.8 | 1.6 | 102.4  | K R F K K F F R K V K K G V H A̲ Y F K K N K F Y I A A T I P Y Y G |
| SP27-17 | 0.8 | 1.6 | ≥204.8 | K R F K K F F R K V K K G V H R A̲ F K K N K F Y I A A T I P Y Y G |
| SP27-18 | 0.8 | 1.6 | ≥204.8 | K R F K K F F R K V K K G V H R Y A̲ K K N K F Y I A A T I P Y Y G |
| SP27-19 | 0.8 | 1.6 | 102.4  | K R F K K F F R K V K K G V H R Y F A̲ K N K F Y I A A T I P Y Y G |
| SP27-20 | 0.8 | 1.6 | 102.4  | K R F K K F F R K V K K G V H R Y F K A̲ N K F Y I A A T I P Y Y G |

TABLE 3-continued

Alanine scan

LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. A. baumannii is the multidrug resistant strain Acinetobacter baumannii RUH875, E. coli is the drug-sensitive strain Escherichia coli LUH15108. Substituted alanines are underlined.

| Peptide | LC99.9 (uM) A. baumannii | LC99.9 (uM) E. coli | Toxicity (μM) | Sequence |
|---|---|---|---|---|
| SP27-21 | 0.8 | 1.6 | 51.2 | K R F K K F F R K V K K G V H R Y F K K <u>A</u> K F Y I A A T I P Y Y G |
| SP27-22 | 1.6 | 1.6 | ≥204.8 | K R F K K F F R K V K K G V H R Y F K K N <u>A</u> F Y I A A T I P Y Y G |
| SP27-23 | 0.4 | 1.6 | ≥204.8 | K R F K K F F R K V K K G V H R Y F K K N K <u>A</u> Y I A A T I P Y Y G |
| SP27-24 | 0.8 | 0.8 | ≥204.8 | K R F K K F F R K V K K G V H R Y F K K N K F <u>A</u> I A A T I P Y Y G |
| SP27-25 | 1.6 | 1.6 | ≥204.8 | K R F K K F F R K V K K G V H R Y F K K N K F Y <u>A</u> A A T I P Y Y G |
| SP27-26 | 0.8 | 1.6 | 102.4 | K R F K K F F R K V K K G V H R Y F K K N K F Y I <u>A</u> A T I P Y Y G |
| SP27-27 | 0.8 | 1.6 | ≥204.8 | K R F K K F F R K V K K G V H R Y F K K N K F Y I A A <u>A</u> I P Y Y G |
| SP27-28 | 0.8 | 0.8 | 25.6 | K R F K K F F R K V K K G V H R Y F K K N K F Y I A A T <u>A</u> P Y Y G |
| SP27-29 | 1.6 | 1.6 | ≥204.8 | K R F K K F F R K V K K G V H R Y F K K N K F Y I A A T I <u>A</u> Y Y G |
| SP27-30 | 0.8 | 1.6 | ≥204.8 | K R F K K F F R K V K K G V H R Y F K K N K F Y I A A T I P Y <u>A</u> G |
| SP27-31 | 0.8 | 1.6 | ≥204.8 | K R F K K F F R K V K K G V H R Y F K K N K F Y I A A T I P Y Y <u>A</u> |

Example 3—D-Amino Acid Substitutions

The amino acids of the SP27 peptide were substituted at various positions with the corresponding D-amino acid. In addition, a peptide containing all D-amino acids and a retro-inverse of SP27 were synthesized. The substituted peptides were tested on an *A. baumannii* bacterial strain for having antimicrobial activity. Furthermore, the substituted peptides were tested for their hemolytic activity as an indicator for their toxicity. The results for antimicrobial activity and toxicity of the modified peptides are shown in Table 4.

TABLE 4

D-amino acid substitutions
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. *A. baumannii* is the multidrug resistant strain *Acinetobacter baumannii* RUH875. L-amino acids in capital letters and D-amino acids in small letters and underlined.

| Peptide | LC99.9 (µM) A. baumannii | Toxicity (µM) | Sequence |
|---|---|---|---|
| SP27 | 0.8 | 102.4 | K R F K K F F R K V K K G V H R Y F K K N K F Y I A A T I P Y Y G |
| SP27-RI | 6.4 | 51.2 | G *y y p i t a a i y f k n k k f y r h v g k k v k r f f k k f r k* |
| SP27-D | 1.6 | 51.2 | *k r f k k f f r k v k k g v h r y f k k n k f y i a a t i p y y g* |
| SP27-32 | 0.8 | 51.2 | *k* R F K K F F R K V K K G V H R Y F K K N K F Y I A A T I P Y Y G |
| SP27-33 | 0.8 | 102.4 | K *r* F K K F F R K V K K G V H R Y F K K N K F Y I A A T I P Y Y G |
| SP27-34 | 0.8 | 102.4 | K R *f* K K F F R K V K K G V H R Y F K K N K F Y I A A T I P Y Y G |
| SP27-35 | 1.6 | 102.4 | K R F *k* K F F R K V K K G V H R Y F K K N K F Y I A A T I P Y Y G |
| SP27-36 | 0.8 | ≥204.8 | K R F K *k* F F R K V K K G V H R Y F K K N K F Y I A A T I P Y Y G |
| SP27-37 | 0.8 | ≥204.8 | K R F K K *f* F R K V K K G V H R Y F K K N K F Y I A A T I P Y Y G |
| SP27-38 | 0.8 | 102.4 | K R F K K F *f* R K V K K G V H R Y F K K N K F Y I A A T I P Y Y G |
| SP27-39 | 0.8 | 102.4 | K R F K K F F *r* K V K K G V H R Y F K K N K F Y I A A T I P Y Y G |
| SP27-40 | 0.4 | ≥204.8 | K R F K K F F R *k* V K K G V H R Y F K K N K F Y I A A T I P Y Y G |
| SP27-41 | 0.8 | ≥204.8 | K R F K K F F R K *v* K K G V H R Y F K K N K F Y I A A T I P Y Y G |
| SP27-42 | 0.8 | ≥204.8 | K R F K K F F R K V *k* K G V H R Y F K K N K F Y I A A T I P Y Y G |
| SP27-43 | 0.8 | 51.2 | K R F K K F F R K V K *k* G V H R Y F K K N K F Y I A A T I P Y Y G |
| SP27-44 | 1.6 | ≥204.8 | K R F K K F F R K V K K G *v* H R Y F K K N K F Y I A A T I P Y Y G |
| SP27-45 | 0.8 | 102.4 | K R F K K F F R K V K K G V *h* R Y F K K N K F Y I A A T I P Y Y G |
| SP27-46 | 1.6 | 51.2 | K R F K K F F R K V K K G V H *r* Y F K K N K F Y I A A T I P Y Y G |
| SP27-47 | 1.6 | 51.2 | K R F K K F F R K V K K G V H R *y* F K K N K F Y I A A T I P Y Y G |
| SP27-48 | 1.6 | ≥204.8 | K R F K K F F R K V K K G V H R Y *f* K K N K F Y I A A T I P Y Y G |
| SP27-49 | 0.8 | ≥204.8 | K R F K K F F R K V K K G V H R Y F *k* K N K F Y I A A T I P Y Y G |
| SP27-50 | 0.8 | 102.4 | K R F K K F F R K V K K G V H R Y F K *k* N K F Y I A A T I P Y Y G |
| SP27-51 | 0.8 | 102.4 | K R F K K F F R K V K K G V H R Y F K K *n* K F Y I A A T I P Y Y G |
| SP27-52 | 0.4 | ≥204.8 | K R F K K F F R K V K K G V H R Y F K K N *k* F Y I A A T I P Y Y G |
| SP27-53 | 0.4 | ≥204.8 | K R F K K F F R K V K K G V H R Y F K K N K *f* Y I A A T I P Y Y G |
| SP27-54 | 0.4 | 51.2 | K R F K K F F R K V K K G V H R Y F K K N K F *y* I A A T I P Y Y G |
| SP27-55 | 0.8 | 51.2 | K R F K K F F R K V K K G V H R Y F K K N K F Y *i* A A T I P Y Y G |
| SP27-56 | 0.4 | 51.2 | K R F K K F F R K V K K G V H R Y F K K N K F Y I *a* A T I P Y Y G |
| SP27-57 | 0.8 | 51.2 | K R F K K F F R K V K K G V H R Y F K K N K F Y I A *a* T I P Y Y G |
| SP27-58 | 0.8 | ≥204.8 | K R F K K F F R K V K K G V H R Y F K K N K F Y I A A *t* I P Y Y G |
| SP27-59 | 0.8 | 51.2 | K R F K K F F R K V K K G V H R Y F K K N K F Y I A A T *i* P Y Y G |

TABLE 4-continued

D-amino acid substitutions
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. A. baumannii is the multidrug resistant strain Acinetobacter baumannii RUH875. L-amino acids in capital letters and D-amino acids in small letters and underlined.

| Peptide | LC99.9 (µM) A. baumannii | Toxicity (µM) | Sequence |
|---|---|---|---|
| SP27-60 | 0.8 | 51.2 | K R F K K F F R K V K K G V H R Y F K K N K F Y I A A T I <u>p</u> Y Y G |
| SP27-61 | 1.6 | 51.2 | K R F K K F F R K V K K G V H R Y F K K N K F Y I A A T I P <u>y</u> Y G |
| SP27-62 | 0.8 | 51.2 | K R F K K F F R K V K K G V H R Y F K K N K F Y I A A T I P Y <u>y</u> G |

Example 4—Length Variations

Shorter variants of the SP27 peptide were tested for their antimicrobial activity on an *A. baumannii* bacterial strain. In this test, both N-terminally and C-terminally amino acids of the SP27 peptide were deleted. Furthermore, the substituted peptides were tested for their hemolytic activity as an indicator for their toxicity.

TABLE 5 length variations
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses lesst han 5% of the human erythrocytes in human plasma within 1 hour. A. baumannii is the multidrug resistant strain Acinetobacter baumannii RUH875.

| Peptide | LC99.9 (µM) A. baumannii | Toxicity (µM) | Sequence |
|---|---|---|---|
| SP27 | 0.8 | 102.4 | K R F K K F F R K V K K G V H R Y F K K N K F Y I A A T I P Y Y G |
| SP27-63 | 0.4 | ≥409.6 | K R F K K F F R K V K K G V H R Y F K K N K F Y |
| SP27-64 | 0.8 | 204.8 | R F K K F F R K V K K G V H R Y F K K N K F Y I |
| SP27-65 | 1.6 | 204.8 | F K K F F R K V K K G V H R Y F K K N K F Y I A |
| SP27-66 | 1.6 | ≥409.6 | K K F F R K V K K G V H R Y F K K N K F Y I A A |
| SP27-67 | 3.2 | ≥409.6 | K F F R K V K K G V H R Y F K K N K F Y I A A T |
| SP27-68 | 12.8 | 204.8 | F F R K V K K G V H R Y F K K N K F Y I A A T I |
| SP27-69 | 25.6 | ≥409.6 | F R K V K K G V H R Y F K K N K F Y I A A T I P |
| SP27-70 | 12.8 | ≥409.6 | R K V K K G V H R Y F K K N K F Y I A A T I P Y |
| SP27-71 | 12.8 | 204.8 | K V K K G V H R Y F K K N K F Y I A A T I P Y Y |
| SP27-72 | 25.6 | 204.8 | V K K G V H R Y F K K N K F Y I A A T I P Y Y G |

Example 5—Peptides that are N-Terminally or C-Terminally Modified with a Polyethylene Glycol (PEG) Group The SP27 peptide was coupled to a Polyethylene glycol (PEG) on either the N-terminal or C-terminal of the peptide. Modified amino acid molecules were used to couple the PEG-groups to the peptides. These modified amino acids contain an amine (—NH2) and carboxyl (—COOH) functional group. The amine functional group is protected with an Fmoc-group, which is removed after coupling the PEG-group to the peptide. For this experiment, the following PEG polymer chains were used: PEG2, PEG3, PEGS, PEG11, and PEG27.

Fmoc-NH-(PEG)2-COOH (Merck, CAS 867062-95-1)
Fmoc-NH-(PEG)3-COOH (Merck, CAS 557756-85-1)
Fmoc-NH-(PEG)5-COOH (Merck, CAS 882847-34-9)
Fmoc-NH-(PEG)11-COOH (Polypure, CAS 756526-01-9)
Fmoc-NH-(PEG)27-COOH (Polypure)

The substituted peptides were tested on an *A. baumannii* bacterial strain for having antimicrobial activity. Furthermore, the substituted peptides were tested for their hemolytic activity as an indicator for their toxicity.

TABLE 6

Peptides that are N-terminally or C-terminally modified with a PEG group
LC99.9 is the lowest concentration of the peptide that kills 99.9% of an inoculum of about one million
bacteria in the presence of 50% (v/v) human plasma within 2 hours. Toxicity is expressed as the highest
concentration of the peptide that lyses less than 5% of the human erythrocytes in human plasma within 1
hour. A. baumannii is the multidrug resistant strain Acinetobacter baumannii RUH875. X = PEG is
polyethyleneglycol; B = amide

| Peptide | LC99.9 (µM) A. baumannii | Toxicity (µM) | Sequence |
| --- | --- | --- | --- |
| SP27 | 0.8 | 102.4 | K R F K K F F R K V K K G V H R Y F K K N K F Y I A A T I P Y Y G |
| SP27-PEG2 | 3.2 | 204.8 | K R F K K F F R K V K K G V H R Y F K K N K F Y I A A T I P Y Y G X B |
| SP27-PEG3 | 1.6 | 102.4 | K R F K K F F R K V K K G V H R Y F K K N K F Y I A A T I P Y Y G X B |
| SP27-PEG5 | 1.6 | 102.4 | K R F K K F F R K V K K G V H R Y F K K N K F Y I A A T I P Y Y G X B |
| SP27-PEG11 | 1.6 | 204.8 | K R F K K F F R K V K K G V H R Y F K K N K F Y I A A T I P Y Y G X B |
| SP27-PEG27 | 0.8 | ≥409.6 | K R F K K F F R K V K K G V H R Y F K K N K F Y I A A T I P Y Y G X B |
| PEG2-SP27 | 0.8 | 102.4 | X K R F K K F F R K V K K G V H R Y F K K N K F Y I A A T I P Y Y G |
| PEG3-SP27 | 0.8 | 102.4 | X K R F K K F F R K V K K G V H R Y F K K N K F Y I A A T I P Y Y G |
| PEG5-SP27 | 0.8 | 102.4 | X K R F K K F F R K V K K G V H R Y F K K N K F Y I A A T I P Y Y G |
| PEG11-SP27 | 0.8 | 102.4 | X K R F K K F F R K V K K G V H R Y F K K N K F Y I A A T I P Y Y G |
| PEG27-SP27 | 0.8 | 102.4 | X K R F K K F F R K V K K G V H R Y F K K N K F Y I A A T I P Y Y G |
| SP27-63 | 0.4 | ≥409.6 | K R F K K F F R K V K K G V H R Y F K K N K F Y |
| SP27-63-PEG2 | 0.8 | ≥409.6 | K R F K K F F R K V K K G V H R Y F K K N K F Y X B |
| SP27-63-PEG3 | 0.8 | ≥409.6 | K R F K K F F R K V K K G V H R Y F K K N K F Y X B |
| SP27-63-PEG5 | 1.6 | ≥409.6 | K R F K K F F R K V K K G V H R Y F K K N K F Y X B |
| SP27-63-PEG11 | 3.2 | ≥409.6 | K R F K K F F R K V K K G V H R Y F K K N K F Y X B |
| SP27-63-PEG27 | 12.8 | ≥409.6 | K R F K K F F R K V K K G V H R Y F K K N K F Y X B |
| PEG2-SP27-63 | 0.4 | ≥409.6 | X K R F K K F F R K V K K G V H R Y F K K N K F Y |
| PEG3-SP27-63 | 0.4 | ≥409.6 | X K R F K K F F R K V K K G V H R Y F K K N K F Y |
| PEG5-SP27-63 | 0.4 | ≥409.6 | X K R F K K F F R K V K K G V H R Y F K K N K F Y |
| PEG11-SP27-63 | 0.8 | ≥409.6 | X K R F K K F F R K V K K G V H R Y F K K N K F Y |
| PEG27-SP27-63 | 1.6 | ≥409.6 | X K R F K K F F R K V K K G V H R Y F K K N K F Y |

Example 6—Non-Natural Substitutions

The amino acids of the SP27 peptide were substituted at various positions with non-natural amino acids. The substituted peptides were tested on an *A. baumannii* bacterial strain for having antimicrobial activity. Furthermore, the substituted peptides were tested for their hemolytic activity as an indicator for their toxicity.

TABLE 7 non-natural substitutions

LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. A. baumannii is the multidrug resistant strain Acinetobacter baumannii RUH875.

| Peptide | LC99.9 (µM) A. baumannii | Toxicity (µM) | Sequence | X |
|---|---|---|---|---|
| SP27 | 0.8 | 102.4 | K R F K K F F R K V K K G V H R Y F K K N K F Y I A A T I P Y Y G | |
| SP27-73 | 0.8 | 51.2 | X R F K K F F R K V K K G V H R Y F K K N K F Y I A A T I P Y Y G | Homolysine (hLys) ε-Methyl lysine |
| SP27-74 | 0.8 | 102.4 | X R F K K F F R K V K K G V H R Y F K K N K F Y I A A T I P Y Y G | (Lys(Me)) ε, ε-Dimethyl lysine |
| SP27-75 | 0.8 | 102.4 | X R F K K F F R K V K K G V H R Y F K K N K F Y I A A T I P Y Y G | (Lys(Me)$_2$) ε, ε, ε-Trimethyl |
| SP27-76 | 0.8 | 102.4 | X R F K K F F R K V K K G V H R Y F K K N K F Y I A A T I P Y Y G | lysine (Lys(Me)$_3$) |
| SP27-77 | 0.8 | 102.4 | X R F K K F F R K V K K G V H R Y F K K N K F Y I A A T I P Y Y G | Ornithine (Orn) |
| SP27-78 | 0.8 | 102.4 | X R F K K F F R K V K K G V H R Y F K K N K F Y I A A T I P Y Y G | 2,3-Diaminopropanoic acid (Dap) |
| SP27-79 | 0.8 | 102.4 | X R F K K F F R K V K K G V H R Y F K K N K F Y I A A T I P Y Y G | 2,4-Diaminobutanoic acid (Dab) |
| SP27-80 | 0.8 | 102.4 | K X F K K F F R K V K K G V H R Y F K K N K F Y I A A T I P Y Y G | Homoarginine (hArg) |
| SP27-81 | 0.8 | 102.4 | K X F K K F F R K V K K G V H R Y F K K N K F Y I A A T I P Y Y G | Methylarginine (Arg(Me)) |
| SP27-82 | 0.8 | 102.4 | K X F K K F F R K V K K G V H R Y F K K N K F Y I A A T I P Y Y G | Asym. dimethylarginine (ADMA) |
| SP27-83 | 0.8 | 51.2 | K X F K K F F R K V K K G V H R Y F K K N K F Y I A A T I P Y Y G | Shortend Arg (Agb) |
| SP27-84 | 0.8 | 102.4 | K X F K K F F R K V K K G V H R Y F K K N K F Y I A A T I P Y Y G | Citrulline (Git) |
| SP27-85 | 0.8 | 51.2 | K R X K K F F R K V K K G V H R Y F K K N K F Y I A A T I P Y Y G | Homophenylalanine (hPhe) |
| SP27-86 | 0.8 | 102.4 | K R X K K F F R K V K K G V H R Y F K K N K F Y I A A T I P Y Y G | Homotyrosine (hTyr) |
| SP27-87 | 0.82 | 204.8 | K R X K K F F R K V K K G V H R Y F K K N K F Y I A A T I P Y Y G | Phenylglycine (Phg) |
| SP27-88 | 0.82 | 204.8 | K R X K K F F R K V K K G V H R Y F K K N K F Y I A A T I P Y Y G | 4-Fluorophenylalanine (Phe(4-F)) |

TABLE 7-continued

LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. A. baumannii is the multidrug resistant strain Acinetobacter baumannii RUH875.

| Peptide | LC99.9 (µM) A. baumannii | Toxicity (µM) | Sequence | non-natural substitutions X |
|---|---|---|---|---|
| SP27-89 | 1.6 | 102.4 | K R X K K F F R R K V K K G V H R Y F K K N K F Y I A A T I P Y Y G | 4-Chlorophenylalanine (Phe(4-Cl)) |
| SP27-90 | 0.8 | 102.4 | K R X K K F F R R K V K K G V H R Y F K K N K F Y I A A T I P Y Y G | 4-Cyanophenylalanine (Phe(4-CN)) |
| SP27-91 | 0.8 | 102.4 | K R X K K F F R R K V K K G V H R Y F K K N K F Y I A A T I P Y Y G | 4-Nitrophenylalanine (Phe(4-NO₂)) |
| SP27-92 | 1.6 | 102.4 | K R X K K F F R R K V K K G V H R Y F K K N K F Y I A A T I P Y Y G | Cyclohexylalanine (Cha) |
| SP27-93 | 0.82 | 204.8 | K R F K K F F R R K X K K G V H R Y F K K N K F Y I A A T I P Y Y G | Norvaline (Nva) |
| SP27-94 | 1.6 | 51.2 | K R F K K F F R R K X K K G V H R Y F K K N K F Y I A A T I P Y Y G | homoleucine (hLeu) |
| SP27-95 | 0.8 | 102.4 | K R F K K F F R R K X K K G V H R Y F K K N K F Y I A A T I P Y Y G | Norleucine (Nle) |
| SP27-96 | 0.8 | 51.2 | K R F K K F F R R K X K K G V H R Y F K K N K F Y I A A T I P Y Y G | 2-Aminobutyric acid (Abu) |
| SP27-97 | 0.8 | 51.2 | K R F K K F F R R K V K K G V X R Y F K K N K F Y I A A T I P Y Y G | 1-Methylhistidine (His(1-Me)) |
| SP27-98 | 0.8 | 51.2 | K R F K K F F R R K V K K G V X R Y F K K N K F Y I A A T I P Y Y G | 3-Methylhistidine (His(3-Me)) |
| SP27-99 | 0.82 | 204.8 | K R F K K F F R R K V K K G V H R X F K K N K F Y I A A T I P Y Y G | O-Methyltyrosine (Tyr(OMe)) |
| SP27-100 | 1.62 | 204.8 | K R F K K F F R R K V K K G V H R X F K K N K F Y I A A T I P Y Y G | Homotyrosine (hTyr) |
| SP27-101 | 1.62 | 204.8 | K R F K K F F R R K V K K G V H R X F K K N K F Y I A A T I P Y Y G | Homophenylalanine (hPhe) |
| SP27-102 | 0.82 | 204.8 | K R F K K F F R R K V K K G V H R X F K K N K F Y I A A T I P Y Y G | 4-Fluorophenylalanine (Phe(4-F)) |
| SP27-103 | 0.8 | 51.2 | K R F K K F F R R K V K K G V H R X F K K N K F Y I A A T I P Y Y G | 4-Chlorophenylalanine (Phe(4-Cl)) |
| SP27-104 | 0.8 | 102.4 | K R F K K F F R R K V K K G V H R X F K K N K F Y I A A T I P Y Y G | 4-Cyanophenylalanine (Phe(4-CN)) |

TABLE 7-continued

LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. A. baumannii is the multidrug resistant strain Acinetobacter baumannii RUH875.

non-natural substitutions

| Peptide | LC99.9 (µM) A. baumannii | Toxicity (µM) | Sequence | X |
|---|---|---|---|---|
| SP27-105 | 0.8 | 102.4 | K R F K K F F R K V K K G V H R X F K K N K F Y I A A T I P Y Y G | 4-Nitrophenylalanine (Phe (4-NO$_2$)) |
| SP27-106 | 0.82 | 204.8 | K R F K K F F R K V K K G V H R X F K K N K F Y I A A T I P Y Y G | Dihydroxyphenylalanine (DOPA) |
| SP27-107 | 0.8 | 51.2 | K R F K K F F R K V K K G V H R Y F K K N K F Y I X A A T I P Y Y G | Norvaline (Nva) |
| SP27-108 | 0.8 | 51.2 | K R F K K F F R K V K K G V H R Y F K K N K F Y I X A A T I P Y Y G | Homoleucine (hLeu) |
| SP27-109 | 0.8 | 51.2 | K R F K K F F R K V K K G V H R Y F K K N K F Y I X A A T I P Y Y G | Norleucine (Nle) |
| SP27-110 | 0.82 | 204.8 | K R F K K F F R K V K K G V H R Y F K K N K F Y I X A A T I P Y Y G | 2-Aminobutyric acid (Abu) |
| SP27-111 | 0.8 | 51.2 | K R F K K F F R K V K K G V H R Y F K K N K F Y I A A T I X Y Y G | Hydroxyproline (Hyp) |
| SP27-112 | 0.4 | 51.2 | K R F K K F F R K V K K G V H R Y F K K N K F Y I A A T I X Y Y G | Isonipecotic acid (Isn) |
| SP27-113 | 0.8 | 102.4 | K R F K K F F R K V K K G V H R Y F K K N K F Y I A A T I X Y Y G | Thiaproline (Thz) |

The invention claimed is:

1. An isolated, synthetic or recombinant peptide having antimicrobial activity and between 20-200 amino acids, said peptide comprising:
   a) at least 20 consecutive amino acids of a retro-inverso sequence of the amino acid sequence of SEQ ID NO:25, the amino acid sequence comprising at least the amino acid sequence of SEQ ID NO:34; or
   b) a functional variant of the amino acid sequence of SEQ ID NO:25, the amino acid sequence comprising at least the amino acid sequence of SEQ ID NO:34, wherein the variant: has one or more substitutions of an amino acid by a corresponding non-natural amino acid, wherein the corresponding non-natural amino acid is a corresponding β-amino acid, or wherein the substitution of an amino acid by a corresponding non-natural amino acid is selected from the group consisting of: alanine is substituted by beta-alanine, t-butylalanine, 2-napthylalanine, L-3-(2-naphthyl)alanine, or 2-aminoisobutyric acid; arginine is substituted by homoarginine, ornithine, N5-carbamoylornithine, 3-amino-propionic acid, methylarginine, asymmetric dimethylarginine, shortened arginine, or citrulline; asparagine is substituted by N-ethylasparagine; glycine is substituted by N-methylglycine, t-butylglycine, or D-allylglycine; histidine is substituted by 3-(3-methyl-4-nitrobenzyl)-L-histidine methyl ester, 1-methylhistidine, or 3-methylhistidine; isoleucine is substituted by isodesmosine, N-methylisoleucine, allo-isoleucine, norvaline, homoleucine, norleucine, or 2-aminobutyric acid; lysine is substituted by 6-N-methyllysine, 2-aminoheptanoic acid, N-acetyl lysine, hydroxylysine, allo-hydroxylysine, homolysine, ε-methyl lysine, ε,ε-dimethyl lysine, ε,ε,ε-trimethyl lysine, ornithine, 2,3-diaminopropanoic acid, or 2,4-diaminobutanoic acid; phenylalanine is substituted by p-amino-L-phenylalanine, 3-benzothienyl alanine p-bromophenylalanine, p-acyl-L-phenylalanine, 2-fluorophenylalanine, 3-fluorophen0ylalanine, 4-fluorophenylalanine, homophenylalanine, homotyrosine, phenylglycine, 4-chlorophenylalanine, 4-cyanophenylalanine, 4-nitrophenylalanine, or cyclohexylalanine; proline is substituted by 3-hydroxyproline, 4-hydroxyproline, isonipecotic acid, thiaproline; threonine is substituted by D-thyroxine or allo-threonine; tyrosine is substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine; valine is substituted by norvaline, N-methylvaline, 3-fluorovaline, homoleucine, norleucine, or 2-aminobutyric acid;

has one or more substitutions of an amino acid by a corresponding D-amino acid; and/or has up to 5 amino acid substitutions.

2. The isolated, synthetic or recombinant peptide according to claim 1, wherein said peptide is N-terminally and/or C-terminally modified.

3. An antimicrobial composition comprising an isolated, synthetic or recombinant peptide having antimicrobial activity and between 20-200 amino acids, the peptide comprising:

a) at least 20 consecutive amino acids of a retro-inverso sequence of SEQ ID NO:25; or b) a functional variant of a), wherein the variant has antimicrobial activity and:

has one or more substitutions of an amino acid by a corresponding non-natural amino acid, wherein the corresponding non-natural amino acid is a corresponding β-amino acid, or wherein the substitution of an amino acid by a corresponding non-natural amino acid is selected from the group consisting of: alanine is substituted by beta-alanine, t-butylalanine, 2-napthylalanine, L-3-(2-naphthyl)alanine, or 2-aminoisobutyric acid; arginine is substituted by homoarginine, ornithine, N5-carbamoylornithine, 3-amino-propionic acid, methylarginine, asymmetric dimethylarginine, shortened arginine, or citrulline; asparagine is substituted by N-ethylasparagine; glycine is substituted by N-methylglycine, t-butylglycine, or D-allylglycine; histidine is substituted by 3-(3-methyl-4-nitrobenzyl)-L-histidine methyl ester, 1-methylhistidine, or 3-methylhistidine; isoleucine is substituted by isodesmosine, N-methylisoleucine, allo-isoleucine, norvaline, homoleucine, norleucine, or 2-aminobutyric acid; lysine is substituted by 6-N-methyllysine, 2-aminoheptanoic acid, N-acetyl lysine, hydroxylysine, allo-hydroxylysine, homolysine, ε-methyl lysine, ε,ε-dimethyl lysine, ε,ε,ε-trimethyl lysine, ornithine, 2,3-diaminopropanoic acid, or 2,4-diaminobutanoic acid; phenylalanine is substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine, homophenylalanine, homotyrosine, phenylglycine, 4-chlorophenylalanine, 4-cyanophenylalanine, 4-nitrophenylalanine, or cyclohexylalanine; proline is substituted by 3-hydroxyproline, 4-hydroxyproline, isonipecotic acid, or thiaproline; threonine is substituted by D-thyroxine or allo-threonine; tyrosine is substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine; valine is substituted by norvaline, N-methylvaline, 3-fluorovaline, homoleucine, norleucine, or 2-aminobutyric acid;

has one or more substitutions of an amino acid by a corresponding D-amino acid; and/or has up to 5 amino acid substitutions; or c) a functional variant of SEQ ID NO:25, the functional variant of SEQ ID NO:25 comprising at least the amino acid sequence of SEQ ID NO:34, wherein the functional variant of SEQ ID NO:25:

has one or more substitutions of an amino acid by a corresponding non-natural amino acid, wherein the corresponding non-natural amino acid is a corresponding (β-amino acid, or wherein the substitution of an amino acid by a corresponding non-natural amino acid is selected from the group consisting of: alanine is substituted by beta-alanine, t-butylalanine, 2-napthylalanine, L-3-(2-naphthyl)alanine, or 2-aminoisobutyric acid; arginine is substituted by homoarginine, ornithine, N5-carbamoylornithine, 3-amino-propionic acid, methylarginine, asymmetric dimethylarginine, shortened arginine, or citrulline; asparagine is substituted by N-ethylasparagine; glycine is substituted by N-methylglycine, t-butylglycine, or D-allylglycine; histidine is substituted by 3-(3-methyl-4-nitrobenzyl)-L-histidine methyl ester, 1-methylhistidine, or 3-methylhistidine; isoleucine is substituted by isodesmosine, N-methylisoleucine, allo-isoleucine, norvaline, homoleucine, norleucine, or 2-aminobutyric acid; lysine is substituted by 6-N-methyllysine, 2-aminoheptanoic acid, N-acetyl lysine, hydroxylysine, allo-hydroxylysine, homolysine, ε-methyl lysine, ε,ε-dimethyl lysine, ε,ε,ε-trimethyl lysine, ornithine, 2,3-diaminopropanoic acid, or 2,4-diaminobutanoic acid; phenylalanine is substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine, homophenylalanine, homotyrosine, phenylglycine, 4-chlorophenylalanine, 4-cyanophenylalanine, 4-nitrophenylalanine, or cyclohexylalanine; proline issubstituted by 3-hydroxyproline, 4-hydroxyproline, isonipecotic acid, thiaproline; threonine is substituted by D-thyroxine or allo-threonine; tyrosine is substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine; valine is substituted by norvaline, N-methylvaline, 3-fluorovaline, homoleucine, norleucine, or 2-aminobutyric acid;

has one or more substitutions of an amino acid by a corresponding D-amino acid; and/or has up to 5 amino acid substitutions;

wherein the composition is selected from the group consisting of a pharmaceutical composition comprising at least one pharmaceutically acceptable carrier, diluent and/or excipient; a cosmetic product; a food product; an oral care product; a cleaning product; and an ophthalmic product.

4. An article coated with an isolated, synthetic or recombinant peptide having antimicrobial activity and between 20-200 amino acids, the peptide comprising:

a) at least 20 consecutive amino acids of a retro-inverso sequence of SEQ ID NO:25; or b) a functional variant of a), wherein the variant has antimicrobial activity and:

has one or more substitutions of an amino acid by a corresponding non-natural amino acid, wherein the corresponding non-natural amino acid is a corresponding β-amino acid, or wherein the substitution of an amino acid by a corresponding non-natural amino acid is selected from the group consisting of: alanine is substituted by beta-alanine, t-butylalanine, 2-napthylalanine, L-3-(2-naphthyl)alanine, or 2-aminoisobutyric acid; arginine is substituted by homoarginine, ornithine, N5-carbamoylornithine, 3-amino-propionic acid, methylarginine, asymmetric dimethylarginine, shortened arginine, or citrulline; asparagine is substituted by N-ethylasparagine; glycine is substituted by N-methylglycine, t-butylglycine, or D-allylglycine; histidine is substituted by 3-(3-methyl-4-nitrobenzyl)-L-histidine methyl ester, 1-methylhistidine, or 3-methylhistidine; isoleucine is substituted by isodesmosine, N-methylisoleucine, allo-isoleucine, norvaline, homoleucine, norleucine, or 2-aminobutyric acid; lysine is substituted by 6-N-methyllysine, 2-aminoheptanoic acid, N-acetyl lysine, hydroxylysine, allo-hydroxylysine, homolysine, ε-methyl lysine, ε,ε-dimethyl lysine, ε,ε,ε-trimethyl lysine, ornithine, 2,3-diaminopropanoic acid, or 2,4-diaminobutanoic acid; phenylalanine is substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine, homophenylalanine, homotyrosine, phenylglycine, 4-chlorophenylalanine, 4-cyanophenylalanine, 4-nitrophenylalanine, or cyclohexylalanine; proline is substituted by 3-hydroxyproline, 4-hydroxyproline, isonipecotic acid, or thiaproline; threonine is substituted by D-thyroxine or allo-threonine; tyrosine is substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine; valine is substituted by norvaline, N-methylvaline, 3-fluorovaline, homoleucine, norleucine, or 2-aminobutyric acid;

has one or more substitutions of an amino acid by a corresponding D-amino acid; and/or has up to 5 amino acid substitutions; or c) a functional variant of SEQ ID NO:25, the functional variant of SEQ ID NO:25 comprising at least the amino acid sequence of SEQ ID NO:34, wherein the functional variant of SEQ ID NO:25:

has one or more substitutions of an amino acid by a corresponding non-natural amino acid, wherein the corresponding non-natural amino acid is a corresponding (3-amino acid, or wherein the substitution of an amino acid by a corresponding non-natural amino acid is selected from the group consisting of: alanine is substituted by beta-alanine, t-butylalanine, 2-napthylalanine, L-3-(2-naphthyl)alanine, or 2-aminoisobutyric acid; arginine is substituted by homoarginine, ornithine, N5-carbamoylornithine, 3-amino-propionic acid, methylarginine, asymmetric dimethylarginine, shortened arginine, or citrulline; asparagine is substituted by N-ethylasparagine; glycine is substituted by N-methylglycine, t-butylglycine, or D-allylglycine; histidine is substituted by 3-(3-methyl-4-nitrobenzyl)-L-histidine methyl ester, 1-methylhistidine, or 3-methylhistidine; isoleucine is substituted by isodesmosine, N-methylisoleucine, allo-isoleucine, norvaline, homoleucine, norleucine, or 2-aminobutyric acid; lysine is substituted by 6-N-methyllysine, 2-aminoheptanoic acid, N-acetyl lysine, hydroxylysine, allo-hydroxylysine, homolysine, ε-methyl lysine, ε,ε-dimethyl lysine, ε,ε,ε-trimethyl lysine, ornithine, 2,3-diaminopropanoic acid, or 2,4-diaminobutanoic acid; phenylalanine is substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine, homophenylalanine, homotyrosine, phenylglycine, 4-chlorophenylalanine, 4-cyanophenylalanine, 4-nitrophenylalanine, or cyclohexylalanine; proline is substituted by 3-hydroxyproline, 4-hydroxyproline, isonipecotic acid, thiaproline; threonine is substituted by D-thyroxine or allo-threonine; tyrosine is substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine; valine is substituted by norvaline, N-methylvaline, 3-fluorovaline, homoleucine, norleucine, or 2-aminobutyric acid;

has one or more substitutions of an amino acid by a corresponding D-amino acid; and/or has up to 5 amino acid substitutions.

5. The isolated, synthetic or recombinant peptide according to claim 1, together with at least one pharmaceutically acceptable carrier, diluent, and/or excipient.

6. The isolated, synthetic or recombinant peptide of claim 2, wherein the N-terminal and/or C-terminal modification comprises an N-terminal and/or C-terminal polyethylene glycol (PEG), polysaccharide, and/or lipid.

7. A method of using the isolated, synthetic or recombinant peptide according to claim 1 for therapy of a subject, wherein the therapy is for the treatment of a bacterial, fungal, viral and/or parasitic infection, an inflammatory condition, or a cancer; or in the treatment of a condition resulting from bacterial, fungal, viral and/or parasitic infection, biofilm formation, an inflammatory condition, or a cancer, wherein the method comprises administering the peptide to the subject.

8. A method of utilizing the isolated, synthetic or recombinant peptide according to claim 1 to inhibit biofilm formation or to degrade biofilms as an anti-bacterial agent, anti-fungal agent, anti-viral agent, anti-parasitic agent, as a diagnostic, crop protectant, disinfectant, preservative anti-inflammatory agent, immune-modulating agent and/or anti-cancer agent, wherein the method comprises applying the peptide so as to inhibit biofilm formation or to degrade a biofilm.

9. The method according to claim 7, wherein the treatment is of a bacterial infection, wherein the bacteria is antibiotic-resistant bacteria, antibiotic-tolerant bacteria, persistent bacteria and/or a biofilm.

* * * * *